(12) United States Patent
Voss et al.

(10) Patent No.: US 10,881,748 B2
(45) Date of Patent: *Jan. 5, 2021

(54) NITROXIDE CONTAINING AMYLOID BINDING AGENTS FOR IMAGING AND THERAPEUTIC USES

(71) Applicant: THE REGENTS OF THE UNIVERSITY OF CALIFORNIA, Oakland, CA (US)

(72) Inventors: John Voss, Woodland, CA (US); Ruiwu Liu, Sacramento, CA (US)

(73) Assignee: The Regents Of The University Of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/595,178

(22) Filed: Oct. 7, 2019

(65) Prior Publication Data

US 2020/0246492 A1    Aug. 6, 2020

Related U.S. Application Data

(63) Continuation of application No. 15/748,556, filed as application No. PCT/US2016/047414 on Aug. 17, 2016, now Pat. No. 10,478,513.

(60) Provisional application No. 62/206,706, filed on Aug. 18, 2015.

(51) Int. Cl.

| | | |
|---|---|---|
| *A61K 49/20* | (2006.01) | |
| *A61K 31/4709* | (2006.01) | |
| *A61K 31/41* | (2006.01) | |
| *C07D 207/273* | (2006.01) | |
| *A61K 31/05* | (2006.01) | |
| *A61K 31/4015* | (2006.01) | |
| *C07D 207/20* | (2006.01) | |
| *A61K 31/4178* | (2006.01) | |
| *C07D 491/052* | (2006.01) | |
| *C07D 207/14* | (2006.01) | |
| *A61K 31/015* | (2006.01) | |
| *A61K 31/353* | (2006.01) | |
| *A61K 31/4184* | (2006.01) | |
| *A61K 31/423* | (2006.01) | |
| *A61K 31/428* | (2006.01) | |
| *A61K 31/4439* | (2006.01) | |
| *A61K 31/53* | (2006.01) | |

(52) U.S. Cl.
CPC .......... *A61K 49/20* (2013.01); *A61K 31/015* (2013.01); *A61K 31/05* (2013.01); *A61K 31/353* (2013.01); *A61K 31/4015* (2013.01); *A61K 31/4178* (2013.01); *A61K 31/4184* (2013.01); *A61K 31/423* (2013.01); *A61K 31/428* (2013.01); *A61K 31/4439* (2013.01); *A61K 31/4709* (2013.01); *A61K 31/53* (2013.01); *C07D 207/14* (2013.01); *C07D 207/20* (2013.01); *C07D 207/273* (2013.01); *C07D 491/052* (2013.01)

(58) Field of Classification Search
CPC ........ A61K 49/20; A61K 31/05; A61K 31/41; A61K 31/4709
See application file for complete search history.

(56) References Cited

U.S. PATENT DOCUMENTS

| | | |
|---|---|---|
| 2009/0123369 A1 | 5/2009 | Kung et al. |
| 2009/0162283 A1 | 6/2009 | Bando et al. |
| 2011/0071301 A1 | 3/2011 | Jin et al. |

OTHER PUBLICATIONS

Fumiya Mito et al. Monitoring the aggregation processes of amyloid-beta using a spin-labeled, fluorescent nitroxyl radical, Chem Commun, 47, 5070-5072. (Year: 2011).*
International Searching Authority at the United States Patent and Trademark Office, International Search Report and Written Opinion for International Patent Application No. PCT/US2016/047414, dated Dec. 30, 2016, 14 pages.
Grimladi et al., "Membrane charge dependent states of the <2>-amyloid fragment A<> (1635) with differently charged micelle agregates", Biochimica et Biophysica Acta, Mar. 1, 2010, pp. 660-671, vol. 1798. No. 3.
Li et al., "Binding Mechanism and Magnetic Properties of a Multifunctional Spin Label for Targeted EPR Imaging of Amyloid Proteins: Insight from Atomistic Simulations and First-Principles Calculations", Journal of Chemical Theory and Computation, Oct. 23, 2012, pp. 4766-4774, vol. 8, No. 11.
Mito et al. "Monitoring the aggregation processes of amyloid-[beta] using a spin-labeled, flourescent nitroxyl radical", Chemical Comunications, Jan. 1, 2011, pp. 5070-5070, vol. 47, No. 7.
Ono et al., "Synthesis and biological evaluation of (e)-3-styrylpyridine derivatives as amyloid imaging agents for Alzheimer's disease", Nuclear Medicine and Biol, Elsevier, NY, US, May 1, 2005, pp. 329-335, vol. 32, No. 4.
Pubchem, Substance Record for SID 77909074, Create date: Jun. 12, 2009, retrieved on Sep. 20, 2016 from <https://pubchem.ncbi.nlm.nih.gov/substance/79909074.
Pubchem, Substance Record for SID 211536141, Create date: Oct. 14, 2014, retrieved on Sep. 20, 2016 from <https://pubchem.ncbi.nlm.nih.gov/substance/211536141.
Qu et al., "Novel Styrylpyridines as Probes for SPECT Imaging of Amyloid Plaques", Journal of Medicinal Chemistry, May 1, 2017, pp. 2157-2165, vol. 50, No. 9.
Petrlova et al. "The Influence of Spin-Labeled Fluorene Compounds on the Assembly and Toxicity of the Aβ Peptide," PLoS one, 7(4), e35443, pp. 1-10 (Apr. 2012).

* cited by examiner

*Primary Examiner* — Michael G. Hartley
*Assistant Examiner* — Jagadishwar R Samala
(74) *Attorney, Agent, or Firm* — Mintz Levin Cohn Ferris Glovsky and Popeo, P.C.

(57) ABSTRACT

The present invention provides methods of using nitroxide spin-labeled amyloid beta-binding compounds to image amyloid. The present invention also provides nitroxide spin-labeled amyloid beta-binding compounds.

8 Claims, 9 Drawing Sheets

Figure 5

| Exp | 5xFAD + vehicle | 5xFAD + SLF | wt + SLF |
|---|---|---|---|
| T2-weighted | | | |
| A | 2.7 ± 0.2 | 1.7 ± 0.3 | 2.6 ± 0.2 |
| B | 2.5 ± 0.2 | 1.3 ± 0.2 | 2.6 ± 0.2 |
| C | 2.6 ± 0.2 | 1.7 ± 0.3 | 2.7 ± 0.2 |
| **T2\*-weighted** | | | |
| A | 2.0 ± 0.2 | 1.5 ± 0.2 | 2.0 ± 0.2 |
| B | 2.4 ± 0.1 | 1.0 ± 0.1 | 1.9 ± 0.2 |
| C | 2.4 ± 0.2 | 1.6 ± 0.2 | 2.8 ± 0.2 |

Figure 15A & B

NITROXIDE CONTAINING AMYLOID BINDING AGENTS FOR IMAGING AND THERAPEUTIC USES

CROSS-REFERENCES TO RELATED APPLICATIONS

This application is a continuation of U.S. application Ser. No. 15/748,556, filed Jan. 29, 2018, which is the U.S. National Stage under § 371 of International Application No. PCT/US2016/047414, filed Aug. 17, 2016, which claims the benefit of U.S. Provisional Application No. 62/206,706, filed Aug. 18, 2015, each of which is incorporated in its entirety herein for all purposes.

STATEMENT AS TO RIGHTS TO INVENTIONS MADE UNDER FEDERALLY SPONSORED RESEARCH AND DEVELOPMENT

This work was supported by Grant No. P30 AG010129 from the National Institute of Health. The Federal Government has certain rights in this invention.

BACKGROUND OF THE INVENTION

Alzheimer's disease (AD) currently affects over 5 million people in the United States, with this number expected to rise dramatically (Hebert et al. (2013) *Neurology* 80:1778). AD is a progressive, insidious neurodegenerative disease of aging resulting in a gradual decline of cognitive function. AD progresses with a complex, multifactorial etiology, however there are two pathological entities present in AD that present targets for both diagnostic and therapeutic endeavors. These targets are insoluble extracellular amyloid beta (AB) plaques, and intracellular neurofibrillary tangles resulting from aggregates of hyperphosphorylated tau, a microtubule-associated protein. While the insoluble deposits of AB plaques serve as a marker for AD, multiple genetic and biochemical lines of evidence support the hypothesis that the Alzheimer's causative agent is the soluble, oligomeric form of the AB peptide (Viola and Klein (2015) *Acta Neuropathol.* 129:183). AB plaques are generated from the aggregation of soluble AB peptides formed when γ and β secretases (proteases) cleave the amyloid precursor protein (APP), a protein constitutively expressed on the plasma membrane of neurons (Zhang et al. (2011) *Mol. Brain* 4:3). Because considerable brain damage due to amyloid plaque deposition typically occurs 10-20 years before a definitive diagnosis of dementia can be made (Sperling et al. (2011) *Alzheimers Dement.* 7:280 and Bateman et al. (2012) *N. Eng. J. Med.* 367:795), it is imperative to develop methods capable of detecting the Alzheimer's disease process at the earliest possible stage. Currently the only definitive diagnostic of AD is applied post mortem, and clinical diagnosis tools are largely limited to memory testing and PET imaging. An alternative accessible and non-invasive method capable of the early detection of AB levels in the brain could be useful in identifying disease risk, facilitating clinical trials, tracking disease progression, and guiding therapies.

Imaging techniques utilizing radiolabeled positron emission tomography (PET) or single photon emission computed tomography (SPECT) that bind to AB peptides in amyloid plaques have the potential to directly assess amyloid burden (Klunk et al. (2004) *Ann. Neurol.* 55:306), but suffer from limited availability, high cost, and a reliance on short-lived radioisotopes. In this regard, a detection method based on Magnetic Resonance Imaging (MRI) for AD risk is highly desirable. MRI can provide advantages over PET and SPECT that include the use of non-radio-active probes, an increased resolution, and the ability to define anatomic details that can be used to quantify the amyloid plaque (Huddleston and Small (2005) *Nat. Clin. Pract. Neurol.* 1:96).

MRI can detect deposits of amyloid plaques when a sufficient amount of endogenous iron is associated with the plaques (Vanhoutte et al. (2005) *Magn. Reson. Med.* 53:607). The presence of metals, in particular the iron in the plaques, generates an accelerated $T2^*$ relaxation rate and negative contrast at regions high in iron-rich AB (Vanhoette et al. (2005) and Jack et al. (2007) *Neuroscientist* 13:38). However, a method dependent on endogenous iron is hindered since $T2^*$ contrast might originate from different sources, such as heme iron present in red blood cells or non-heme iron present in cerebral tissue (Jack et al. (2007) and Gelman et al. (2001) *J. Neurochem.* 45:71). In addition, some regions of the brain contain iron-poor AB depositions (Vanhoutte et al. (2005) and Ghribi et al. (2006) *J. Neurochem.* 99:438), making accurate evaluation of total AB load by iron-induced contrast difficult.

While iron-rich amyloid plaque provides some negative contrast in MRI (Jack et al. (2007) and Wadghiri et al. (2012) *Methods Mol. Biol.* 849:435), the lack of signal from iron-poor amyloid limits the significance of the approach for a general assessment of AB levels in the brain (Adlard et al. (2014) *Front Neurosci.* 8:327). Towards the goal to diagnose AD using MRI, various agents that target AB to generate enhanced contrast in MRI have been created. For example, magnetic nanostructures doped with superparamagnetic iron have been tethered to antibodies directed against the oligomeric form of AB to generate contrast in the brains of AD mice (Viola et al. (2015) *Nat. Nanotechnol.* 10:91). In addition, several Gd(III)-based approaches have explored conjugating a metal chelator to either AB itself (Wadghiri et al. (2012) and Poduslo et al. (2002) *Neurobiol. Dis.* 11:315), or to an antigen-binding fragment directed against AB (Ramakrishnan et al. (2008) *Pharm. Res.* 25:1861). Small molecules with affinity for AB assemblies have also been combined with Gd(III) chelators to produce contrast at AB, however addition of the chelated Gd(III) to the targeting molecule diminishes amyloid binding and blood-brain barrier permeability (Bort et al. (2014) *Eur. J. Med. Chem.* 87:843). While metal-containing and/or antibody-directed probes show promise, concerns and limitations drive the need for alternative small molecule agents. For example antibody-directed agents may increase inflammatory cascades (Fuller et al. (2015) 130:699), and use of immunoglobin-conjugated Gd(III) agents have low transport in the parenchyma of the brain (Wadghiri et al. (2012)). In addition, use of chelated Gd(III) is contraindicated in many patients with kidney or liver disease (Khawaj a et al. (2015) *Insights Imaging* 6: 553). More importantly, the recent evidence that gadolinium is sequestered in the brain many years after contrast-enhanced MRI (Karabulut (2015) *Diagn. Interv. Radiol.* 21:269) provides an impetus to explore gadolinium-free imaging options for both immunoglobulin—as well as small molecule-based amyloid specific ligands.

One option for creating such ligands is through the attachment of a spin label such as nitroxide. Spin labeled compounds have been shown to interact with AB peptide oligomers and to demonstrate potential therapeutic value (Altman et al. (2015) *Biochim. Biophys. Acta* 2854:1860; Petrlova et al. (2012) *PLoS One* 7:e35443; and Hong et al. (2010) *Neurobiol. Aging* 31:1690). Other work has demonstrated the use of labeled thioflavin compounds to study fibril redox state changes with fluorescence and electron spin resonance (Mito et al.(2011) *Chem. Commun.* 47:5070). However, the use of nitroxide spin labels in MRI applications has been limited due to a demonstrated weakness in relaxivity (Maliakal et al. (2003) *J. Phys. Chem. A* 107:8467; Winalski et al. (2008) *Osteoarthritis Cartilage* 16:815; and Rajca et al. (2012) *J. Am. Chem. Soc.* 134:15724). In addressing this limitation, the present invention surprisingly meets the need for accessible and non-invasive methods of amyloid imaging as well as other needs.

BRIEF SUMMARY OF THE INVENTION

In one embodiment, the present invention provides a method of imaging amyloid, the method including administering to a subject an effective amount of a compound having the structure of formula I:

$$X—(Y)_n \qquad (I)$$

such that the compound binds to the amyloid. X of formula I is an amyloid beta binding compound. Y of formula I is a nitroxide. Subscript n can be an integer from 1 to 3. The method further includes detecting the compound bound to the amyloid, thereby imaging the amyloid.

In a second embodiment, the present invention provides compounds having the structure of formula II:

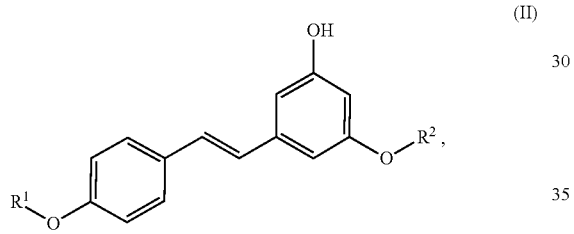

wherein $R^1$ and $R^2$ of formula I can each independently be H or a nitroxide. The nitroxide can be:

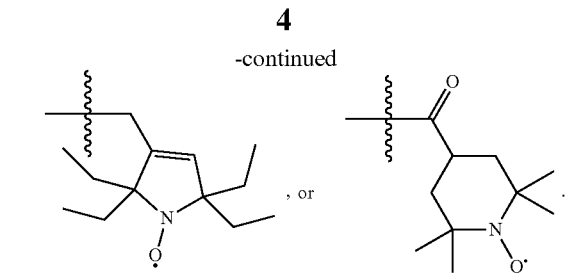

At least one of $R^1$ and $R^2$ is a nitroxide.

In a third embodiment, the present invention provides compounds having the structure of formula III:

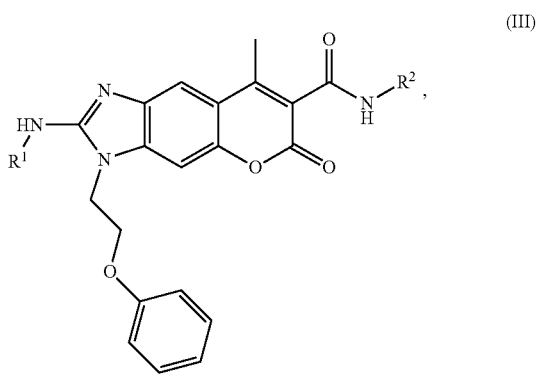

or formula IV:

wherein $R^1$ and $R^2$ of formulas III and IV can each independently be H,

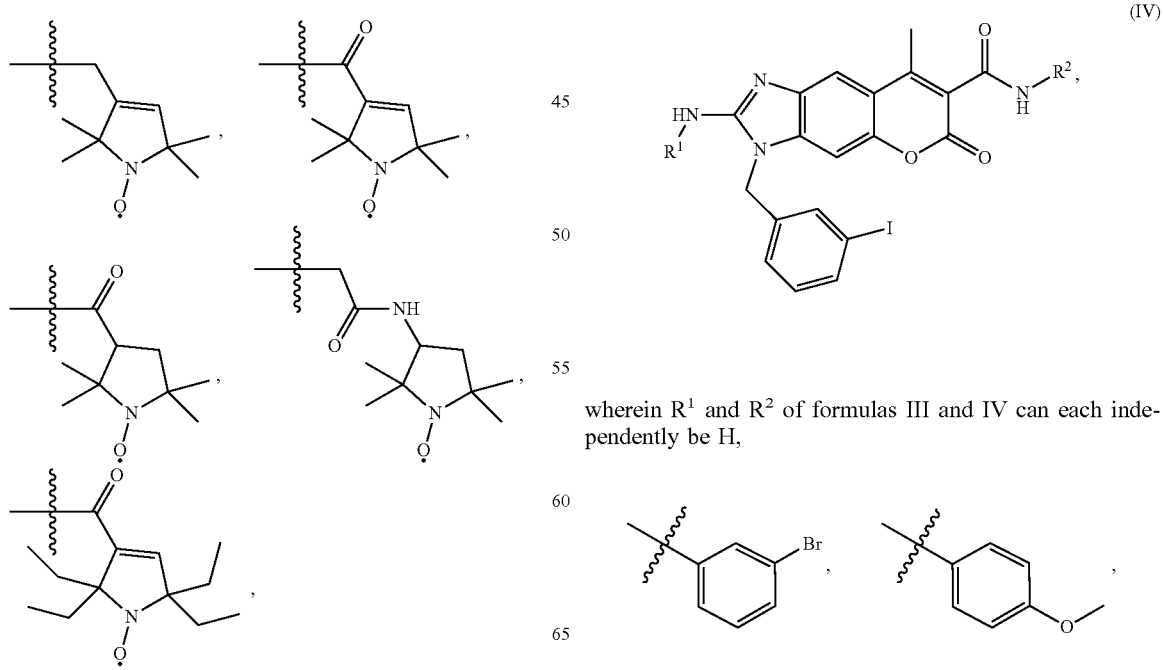

or a nitroxide. The nitroxide can be
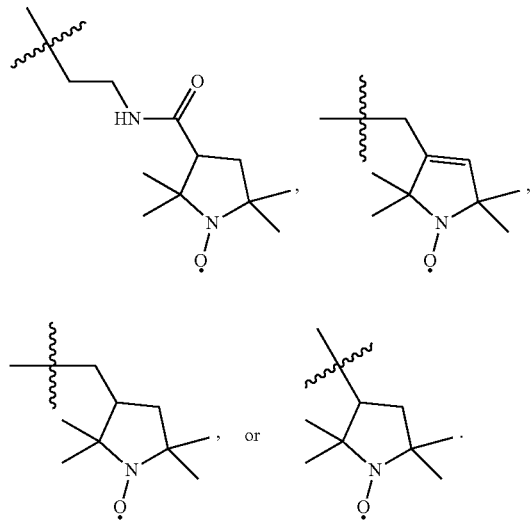
At least one of $R^1$ and $R^2$ is a nitroxide.
In a fourth embodiment, the present invention provides compounds having the structure of formula V:
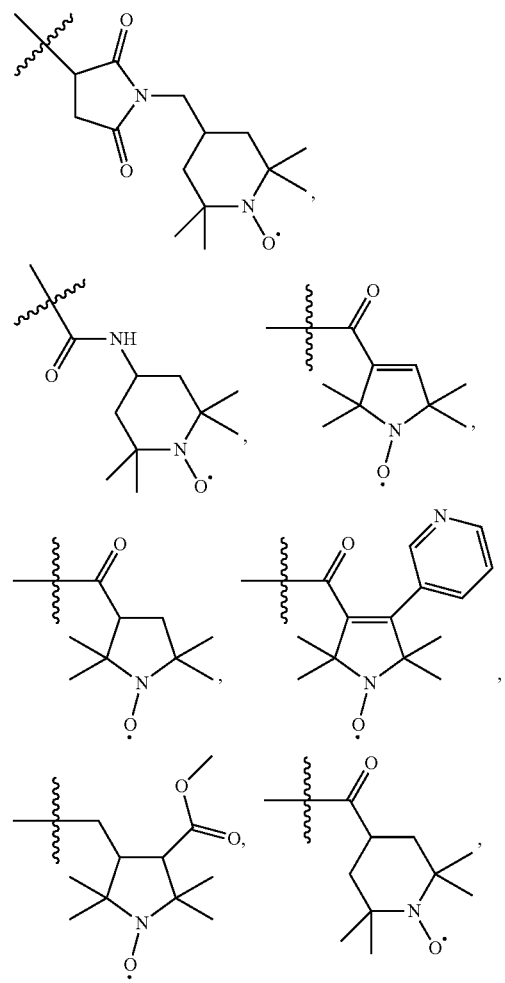
(V)
wherein $R^1$ can be
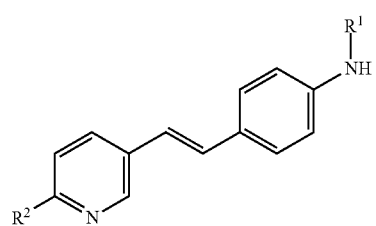
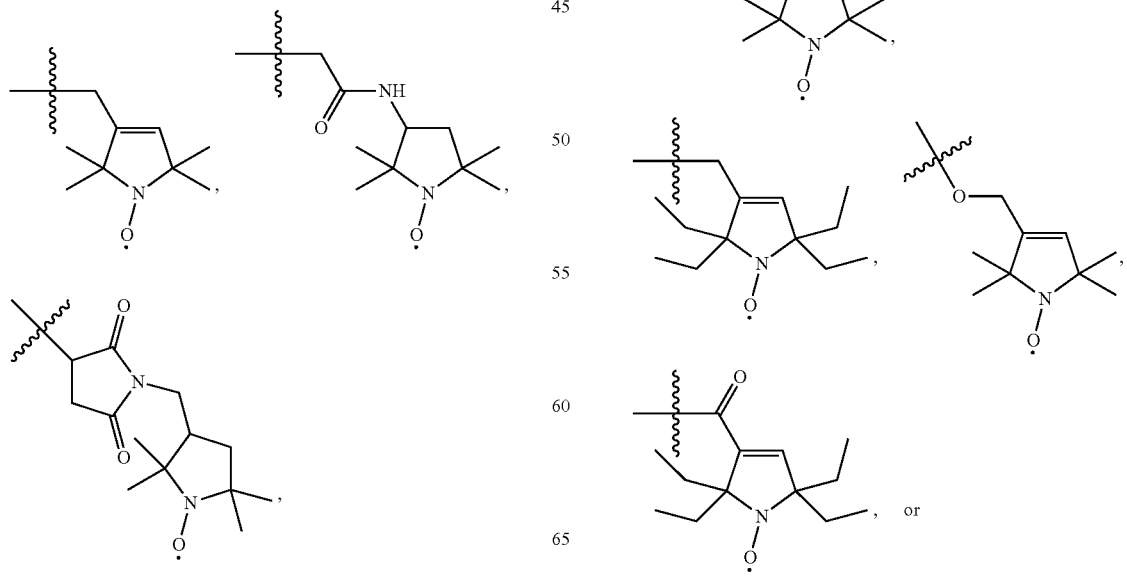
, or

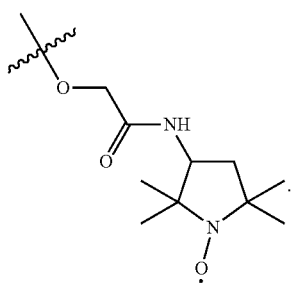
$R^2$ can be OH, OCH$_3$, OCH$_2$CH$_3$, OCH$_2$CH$_2$F, CH$_3$, or (OCH$_2$CH$_2$)$_3$F.
In a fifth embodiment, the present invention provides compounds having the structure of formula VI:
(VI)
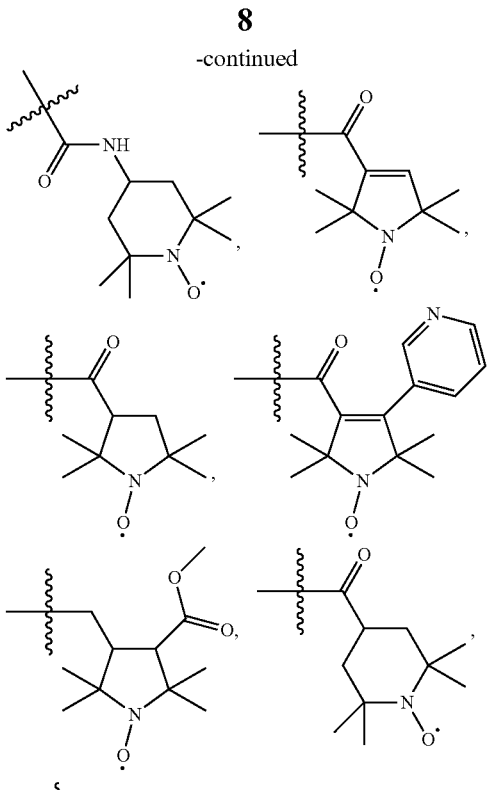
wherein $R^1$ can be
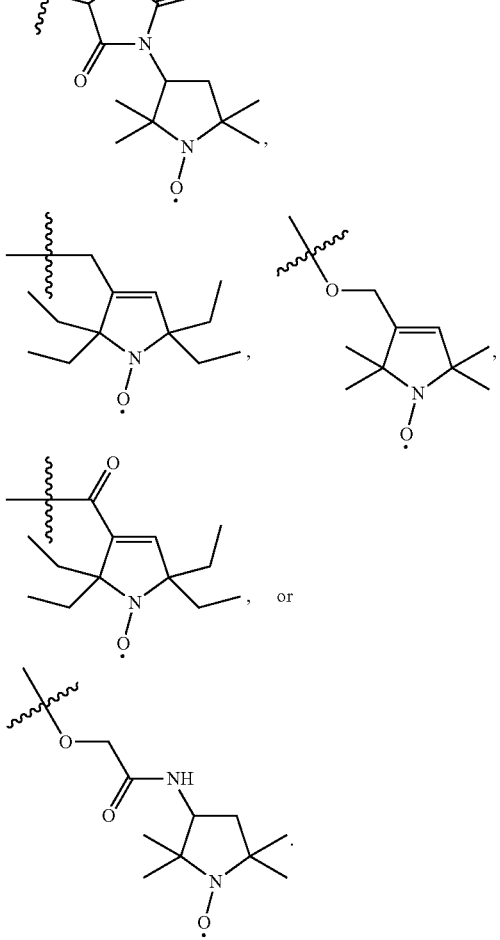

$R^2$ can be OH, $OCH_3$, $OCH_2CH_3$, $OCH_2CH_2F$, $CH_3$, or $(OCH_2CH_2)_3F$.

In a sixth embodiment, the present invention provides a diagnostic composition for imaging amyloid, comprising a compound of formula I:

$$X—(Y)_n \quad (I)$$

wherein X of formula I is an amyloid beta binding compound, Y of formula I is a nitroxide, and subscript n can be an integer from 1 to 3.

In a seventh embodiment, the present invention provides a method of treating a disorder, the method including administering to a subject in need of such a treatment, a therapeutically effective amount of a compound of any of formulas (II)-(VI).

BRIEF DESCRIPTION OF THE DRAWINGS

FIG. 5 shows negative contrast generated by HO-4160 nitroxide spin-labeled fluorine (SLF) in magnetic resonance images of mouse brain specimens from the 5xFAD Alzheimer's mouse model, which produces elevated amyloid beta levels in the brain (Oakley et al. (2006) *J. Neuorsci.* 26:10129). Three independent experiments were carried out (A, B, C) on specimens from 5xFAD and wild type (WT) mice. The sample source and treatment conditions for each column are indicated in the figure header. Each row represents an independent experiment showing images from same coordinates selected from the position providing the most intense slice image under T2 (upper panel) or T2* (lower panel) weighting. Numbers under each box represent intensity values (x $10^5$) of the brain region absent air or anatomical artifact. In each experiment, the two 5xFAD images are distinct slices from the same animal.

FIGS. 15A and B show LRL1-2 and RES1-3 antioxidant activity by spin trapping. FIG. 15A shows EPR detection of BMPO adduct with hydroxyl radical (Eur J Med Chem, 2014, 77, 343-50). The black trace shows the spectrum of BMPO-OH in the absence of added ROS scavenger. The red trace shows the composite EPR spectrum of BMPO-OH+ nitroxide for the LRL1 sample. Reduction in BMPO-OH signal correlates with ROS scavenging. Scavenging activity was measured as a decrease in the amplitude of the second BMPO-OH line (red arrow) compared to the no addition BMPO-OH signal (black arrow). Relative activity is plotted in FIG. 15B.

DETAILED DESCRIPTION OF THE INVENTION

I. General

Figure 1:
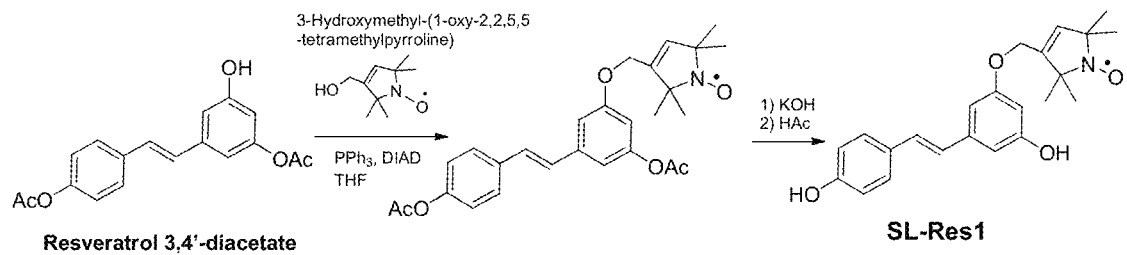
FIG. 1 shows a scheme for the synthesis of the nitroxide spin-labeled compound SL-Res 1.

The present invention provides methods of imaging amyloid by administering a nitroxide spin-labeled amyloid beta binding compound to a subject and detecting the compound bound to amyloid. The present invention also provides nitroxide spin-labeled compounds capable of binding amyloid.

II. Definitions

The abbreviations used herein have their conventional meaning within the chemical and biological arts.

"Imaging" refers to using a device outside of the subject to determine the location of an imaging agent, such as a compound of the present invention. Examples of imaging tools include, but are not limited to, positron emission tomography (PET), magnetic resonance imaging (MRI), electron paramagnetic resonance (EPR), electron spin resonance microscopy (ESRM), ultrasound, single photon emission computed tomography (SPECT) and x-ray computed tomography (CT).

"Amyloid" refers to an aggregate of proteins. The proteins of an amyloid can be misfolded such that their misfolded shapes promote aggregation. The amyloids can comprise, for example, proteins such as amyloid beta (AB), amylin, alpha-synuclein, huntingtin, calcitonin, atrial natriuretic peptide, apolipoprotein Al, serum amyloid A, medin, prolactin, transthyretin, lysozyme, beta-2-microglobulin, gelsolin, keratoepithelin, cystatin, or immunoglobulin light chain AL. Amyloid within a subject can be present in the form of oligomers, plaques, or fibrils. The presence of amyloid in a subject can disrupt healthy physiological function of tissues and organs within the subject. The presence of amyloid in a subject can be associated with an increased risk or occurrence of a disease. The disease associated with the presence of amyloid can be, for example, Alzheimer's disease, diabetes, Parkinson's disease, spongiform encephalopathy, Huntington's disease, thyroid carcinoma, atrial amyloidosis, atherosclerosis, arthritis, prolactinomas, polyneuropathy, corneal dystrophy, or cerebral amyloid angiopathy. The presence of amyloid in a subject can be associated with an increased risk or occurrence of Alzheimer's disease.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to animals such as mammals, including, but not limited to, primates (e.g., humans), cows, sheep, goats, horses, dogs, cats, rabbits, rats, mice and the like. In certain embodiments, the subject is a human.

"Nitroxide" refers to a stable aminoxyl radical compound or group having the structure $R_2N$—O● in which a nitrogen atom is single bonded to an oxygen atom. The R groups of the nitroxide can be the same or different. The R groups can form a fused ring.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference. Pharmaceutically acceptable salts of the acidic compounds of the present invention are salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

Similarly acid addition salts, such as of mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compounds of the present invention possess asymmetric carbon atoms (optical centers) or double bonds; the racemates, diastereomers, geometric isomers and individual isomers are all intended to be encompassed within the scope of the present invention.

"Hydrate" refers to a compound that is complexed to at least one water molecule. The compounds of the present invention can be complexed with from 1 to 10 water molecules.

"Nanoparticle" refers to a defined particle of typically 5 to 500 atoms. Typical dimensions of the nanoparticles of the present invention are on the scale of a few nanometers, and can be tens of nanometers. The nanoparticles of the present invention typically have dimensions of less than 100 nanometers.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and deleterious to the recipient thereof "Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

"Therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of*

Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom. The treatment or amelioration of symptoms can be based on any objective or subjective parameter; including, e.g., the result of a physical examination.

III. Methods of Imaging Amyloid

The present invention provides several methods of imaging amyloid. The methods include administering to a subject an effective amount of a compound having the structure:

X—(Y)$_n$ (I)

wherein X of formula I is an amyloid beta binding protein, Y is a nitroxide, and n is an integer from 1 to 3. The administering is such that the compound binds to the amyloid. The method further includes detecting the compound bound to the amyloid, thereby imaging the amyloid. In some embodiments, n of formula I is 1. In some embodiments, n is 2. In some embodiments, n is 3.

The detecting of the amyloid-bound compound can occur at least 10 minutes, at least 20 minutes, at least 30 minutes, at least 40 minutes, at least 50 minutes, at least 60 minutes, at least 70 minutes, at least 80 minutes, at least 90 minutes, at least 2 hours, at least 3 hours, at least 4 hours, at least 5 hours, at least 6 hours, at least 7 hours, at least 8 hours, at least 9 hours, or at least 10 hours subsequent to the administering of the compound to the subject. In some embodiments, the detecting occurs at least 60 minutes subsequent to the administering.

The detecting can include the use of one or more medical imaging technologies. In some embodiments, the detecting comprises magnetic resonance imaging (MRI), imaging or spectroscopic modalities of electron paramagnetic resonance (EPR, also known as electron spin resonance (ESR)), positron emission tomography (PET), or electron spin resonance microscopy (ESRM). In some embodiments, the detecting comprises MRI. In some embodiments, the detecting comprises both MRI and PET.

EPR is a magnetic resonance technique that is based on the spin acquired by unpaired electrons when placed within an external magnetic field. This spin can be oriented such that it is either opposed to or aligned with the external magnetic field. Unpaired electrons will transition between energy levels in response to a photon having an energy amount equal to the difference in unpaired electron energy levels. By quantifying the energies absorbed in this way by a material with unpaired electrons, an EPR spectra for the material can be obtained. Because few naturally occurring materials have unpaired electrons, EPR is most commonly used to study the interactions of stable radicals, such as nitroxides, with these naturally occurring materials, and not to image the naturally occurring material itself MRI is an alternative magnetic resonance technique that is based on the spin acquired by nuclear protons when placed in an external magnetic field. The magnetic field used for MRI is typically in the form of a field gradient. This magnetic gradient results in a resonance frequency gradient, as the resonance frequency is directly proportional to the magnetic field. By mapping energy absorption intensities at different resonance frequencies, the numbers and positions of protons in a material can then both be determined. Many naturally-occurring materials can be imaged in this way. For example, the amount and location of water present in soft tissue can be detected by probing the magnetic resonance associated with protons of the water. In this way, MRI can be used to not only image a compound, such as a nitroxide spin-labeled compound, administered to a subject, but also the anatomical features of the subject in proximity to the probe.

PET is a radiation detection technique used to observe metabolic processes in a subject. In this technique, positrons emitted from an administered radioactive tracer compound interact with electrons, producing gamma ray pairs traveling in approximately opposite directions. These gamma rays are detected by scintillators of a scanning device situated about the subject. Data associated with these detection events are then used to construct a map or image of the locations of tissues in which the tracer compound is concentrated.

In some embodiments, the detecting and imaging is done with T1-weighted MRI. In some embodiments, the detecting and imaging is done with T2*-weighted MRI. The T2*-weighted MRI can provide a greater imaging contrast for nitroxide spin-labeled compounds in some circumstances.

In some embodiments, the amyloid comprises amyloid aggregates. In some embodiments, the amyloid comprises amyloid beta. The amyloid can be in the form of soluble amyloid or amyloid beta oligomers, or insoluble plaques or fibers. The amyloid can be in the brain of a subject. In some embodiments, the subject is at risk of or currently diagnosed with Alzheimer's disease. In some embodiments, the subject is not receiving the compound for therapeutic purposes. In some embodiments, the compound penetrates the intact blood-brain barrier to bind to cerebral amyloid beta aggregates.

The amyloid beta-binding compound can be any compound that targets amyloid beta with sufficient specificity and affinity. In some embodiments, the amyloid beta-binding compound of formula I can be:

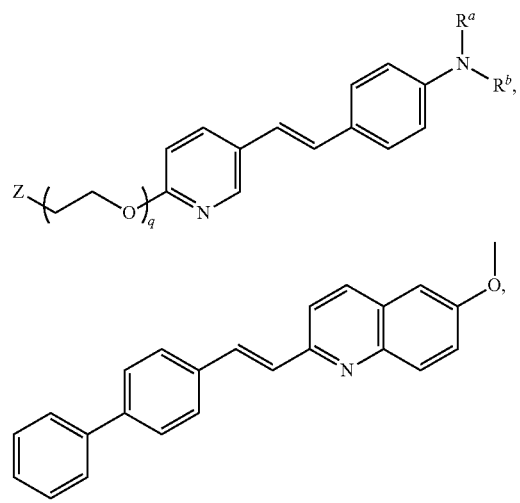

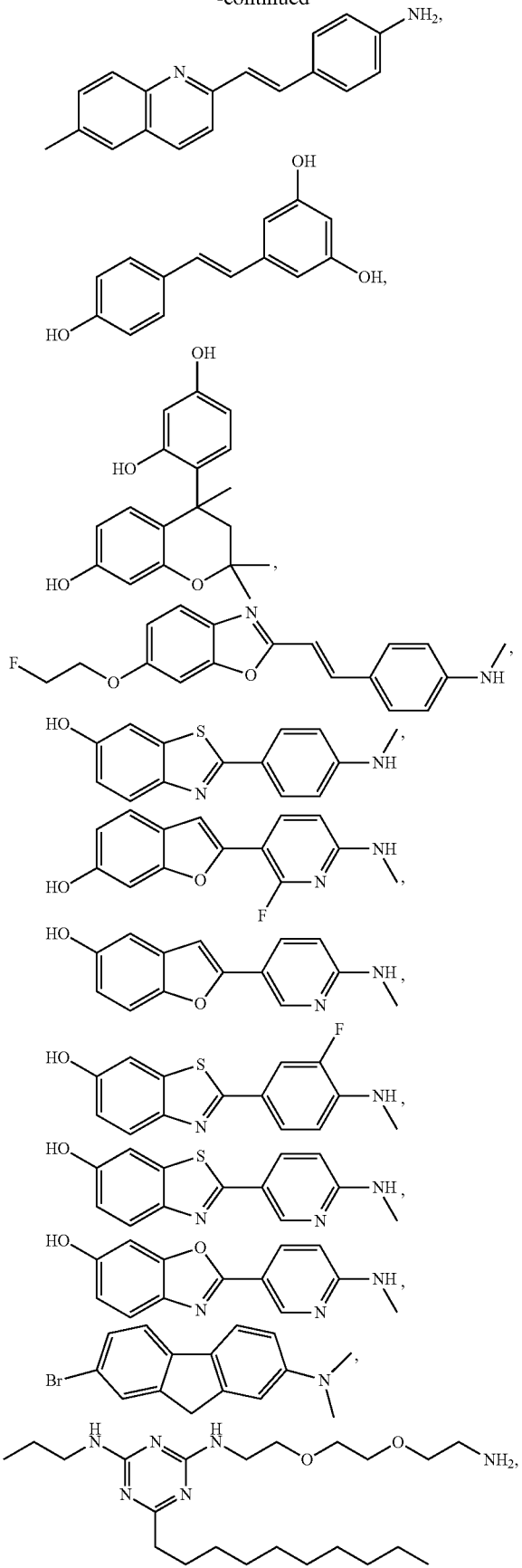
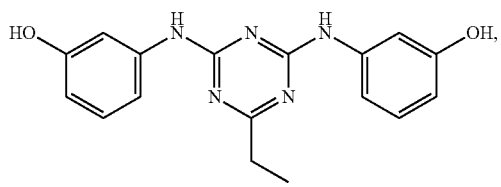
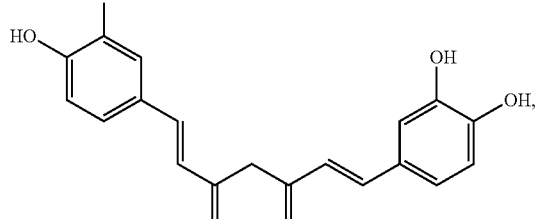
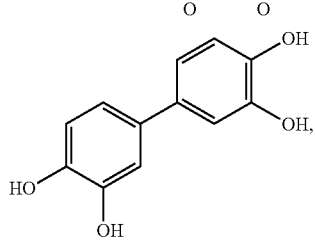
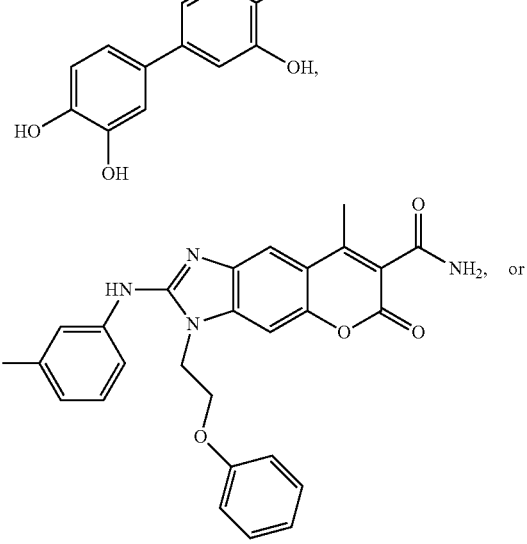
wherein $R^a$ and $R^b$ can each independently be H or $C_{1-4}$ alkyl; Z can be I, $^{123}$I, $^{125}$I, $^{131}$I, Br, $^{76}$Br, $^{77}$Br, F, $^{18}$F, or —O-tosyl; and q can be an integer from 2 to 5.
In some embodiments, the amyloid beta-binding compound can be:
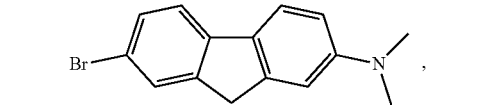

-continued
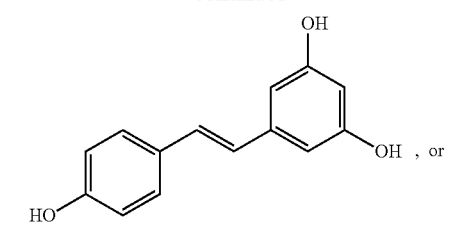, or
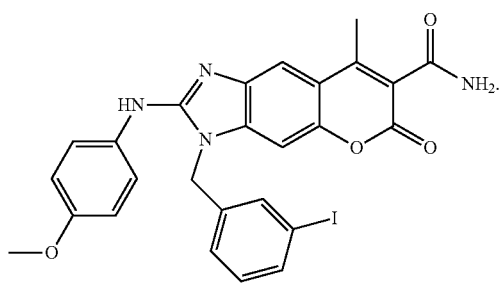 [SMILES: COc1ccc(Nc2nc3cc4c(C)c(C(N)=O)c(=O)oc4cc3n2Cc2cccc(I)c2)cc1]
In some embodiments, the nitroxide of formula I can be:
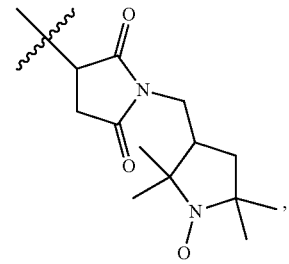
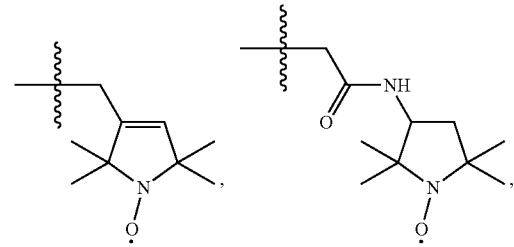
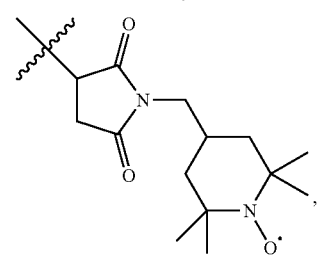
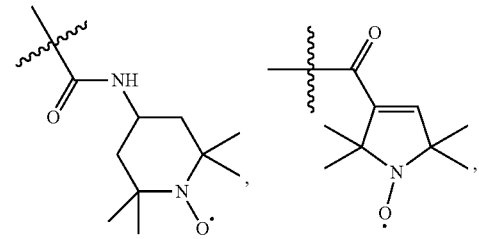
-continued
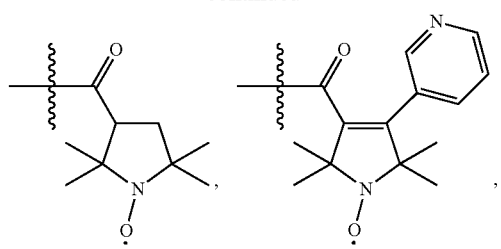
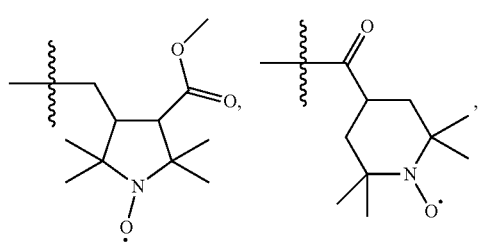
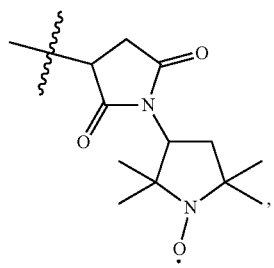
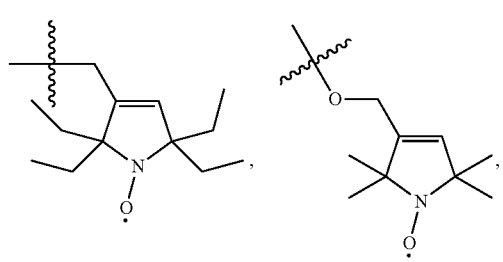
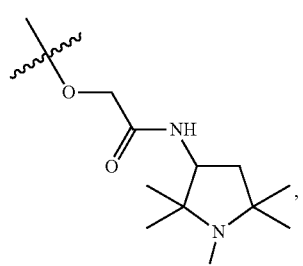
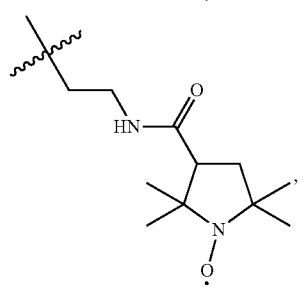

-continued
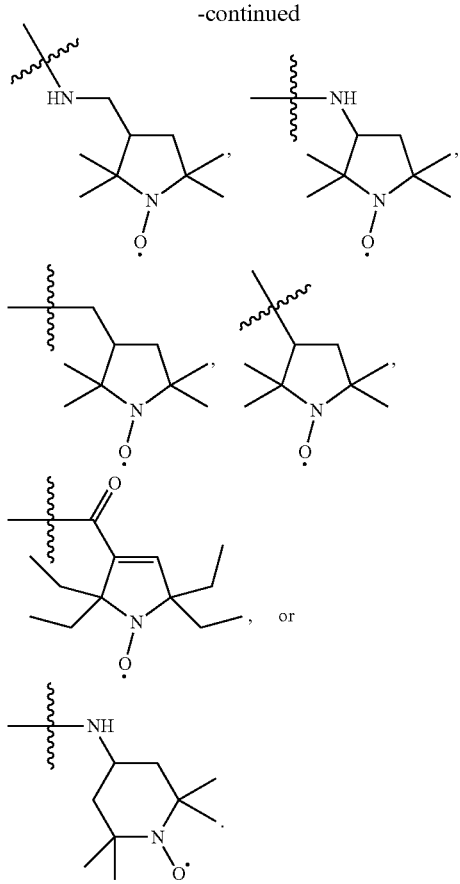
In some embodiments, the nitroxide can be:
In some embodiments, the compound of formula I can be:
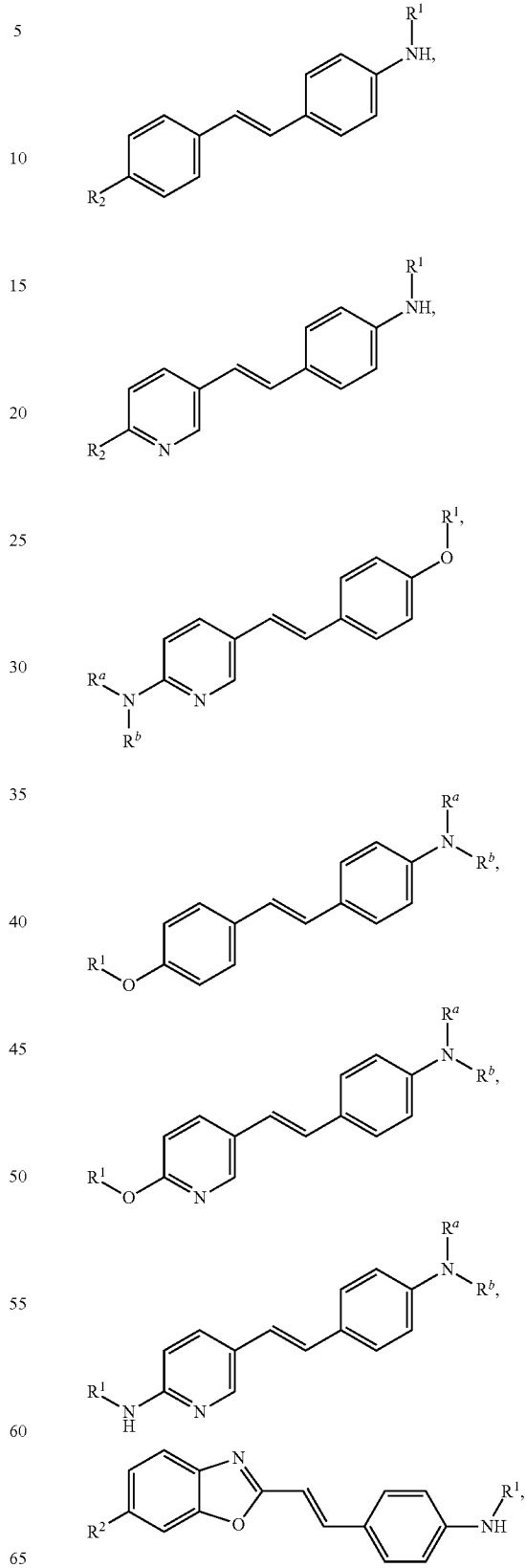

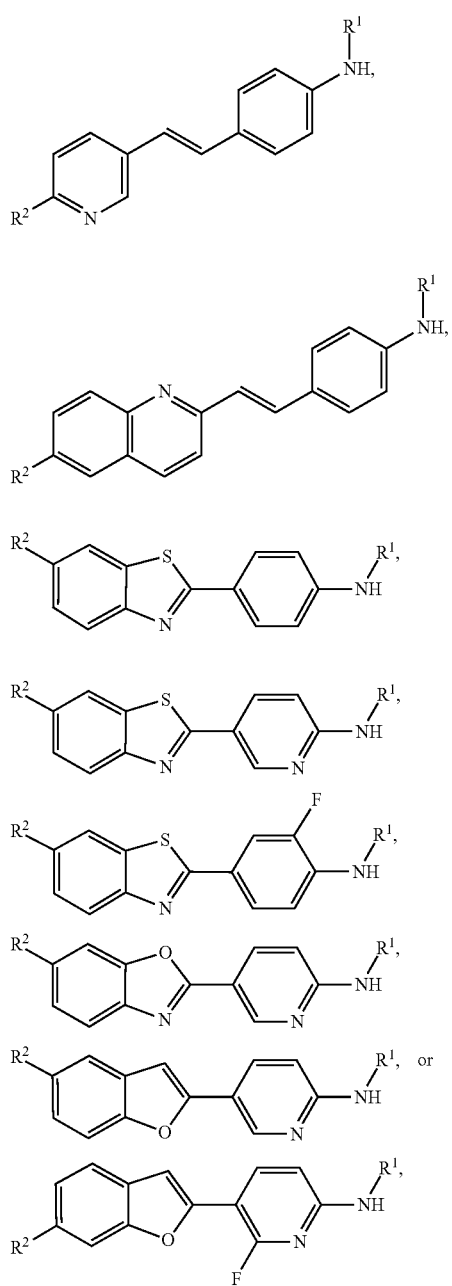
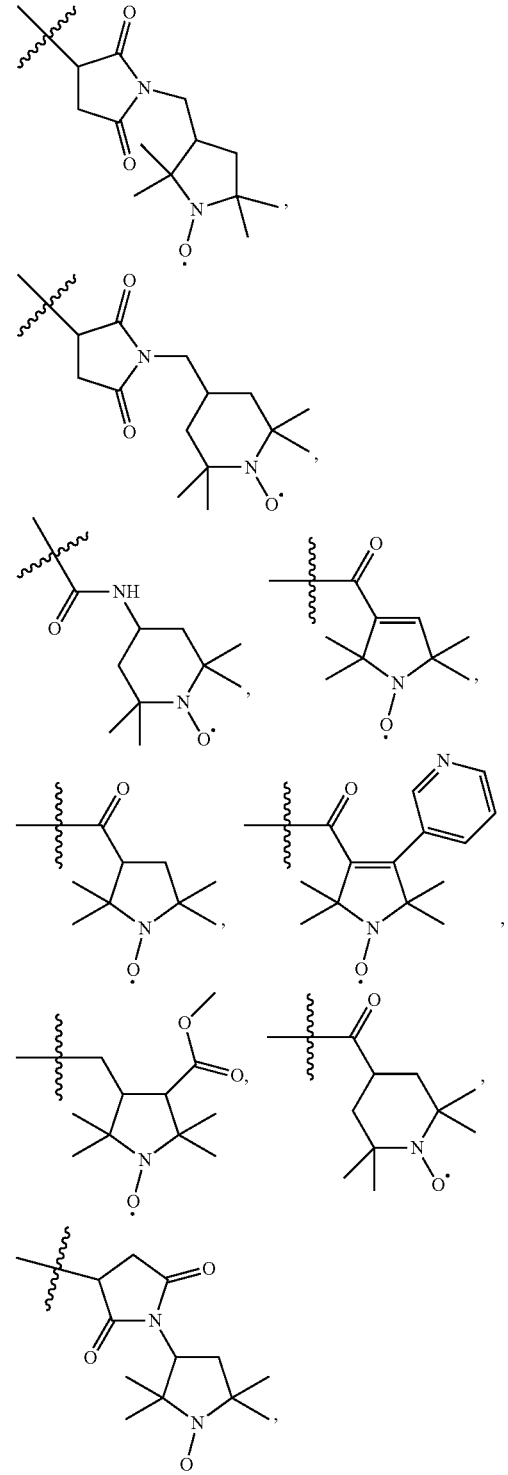
wherein $R^a$ and $R^b$ can each independently be H or $C_{1-4}$ alky. $R^1$ can be:
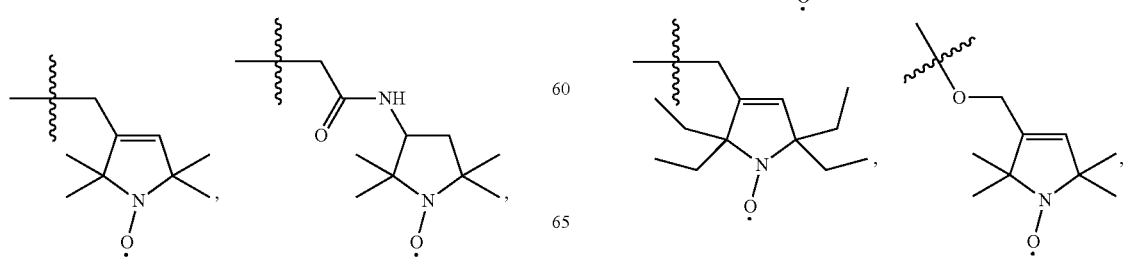

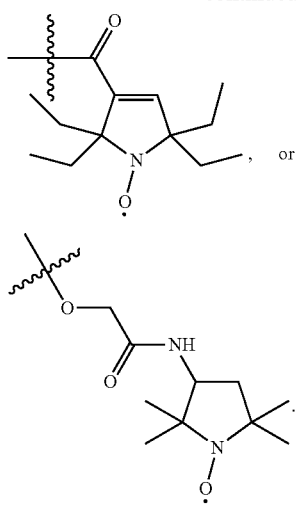
, or
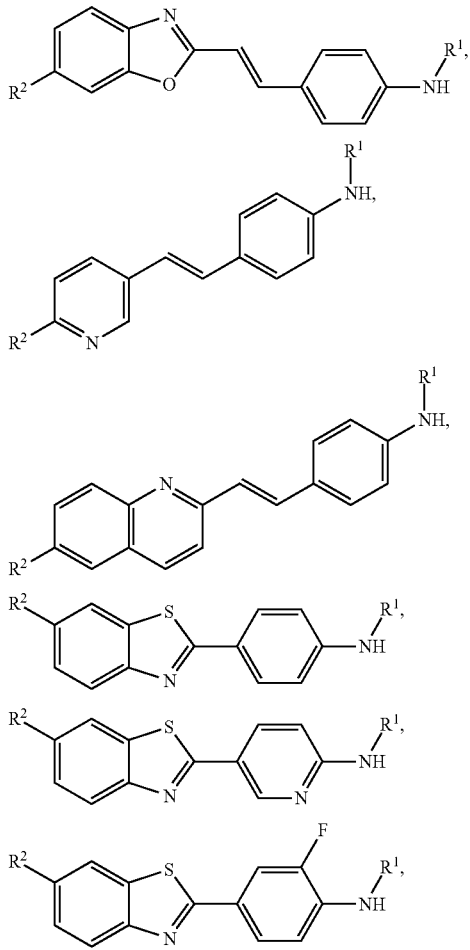
R² can be OH, alkyl, alkoxy, or haloalkoxy. In some embodiments, R² can be OH, OCH₃, OCH₂CH₃, OCH₂CH₂F, CH₃, or (OCH₂CH₂)₃F.
In some embodiments, the compound of formula I can be:
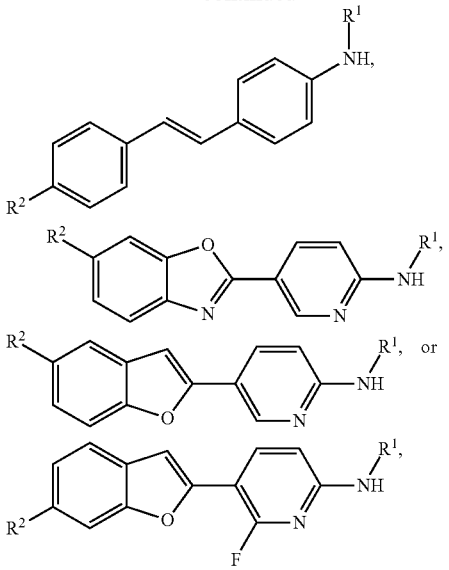
wherein R¹ can be:
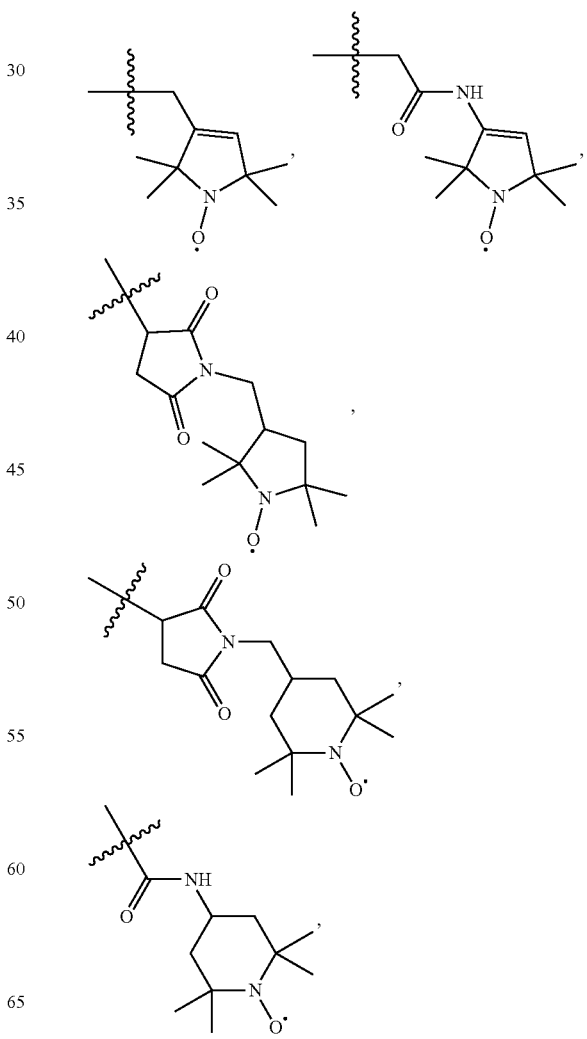

-continued
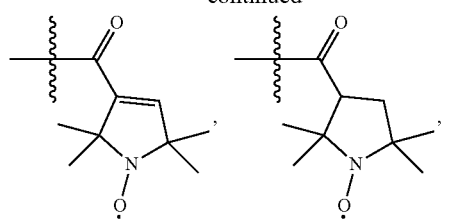
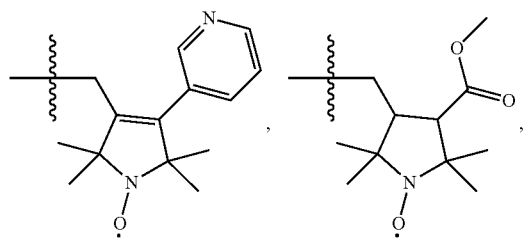
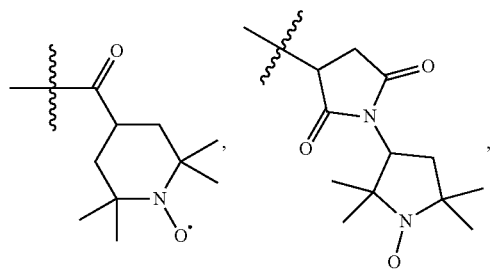
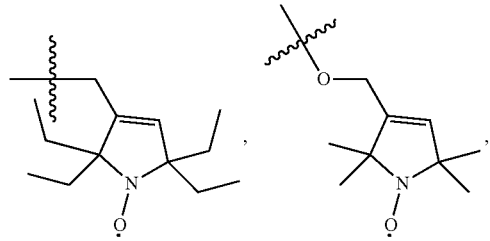
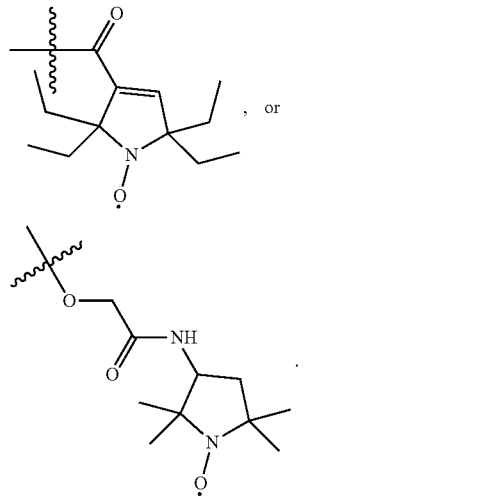
, or
$R^2$ can be OH, alkyl, alkoxy, or haloalkoxy. In some embodiments, $R^2$ can be OH, OCH$_3$, OCH$_2$CH$_3$, OCH$_2$CH$_2$F, CH$_3$, or (OCH$_2$CH$_2$)$_3$F.
In some embodiments, the compound of formula I has the structure:
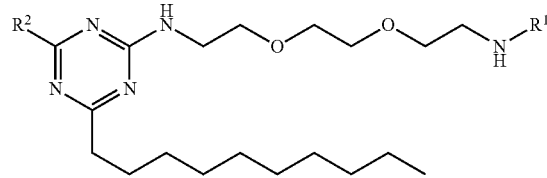
wherein $R^1$ is methyl or a nitroxide. The $R^1$ nitroxide can be:
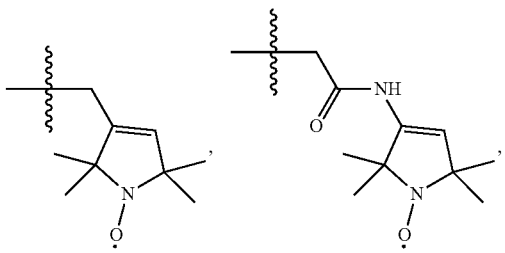
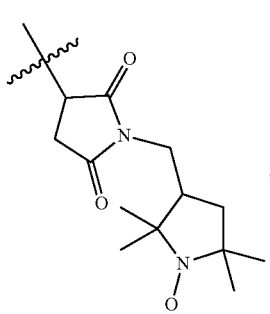
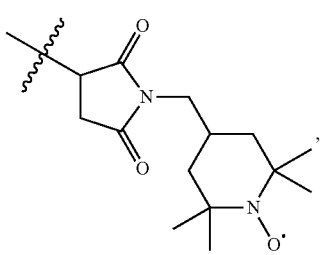
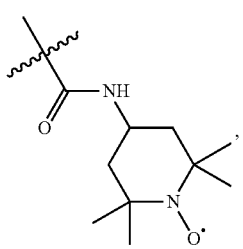
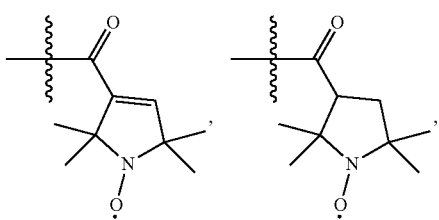

-continued
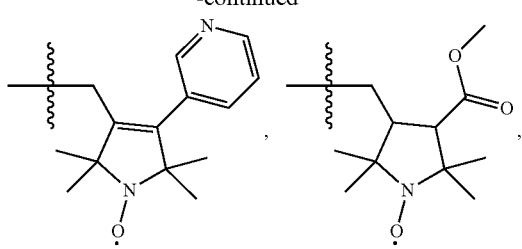
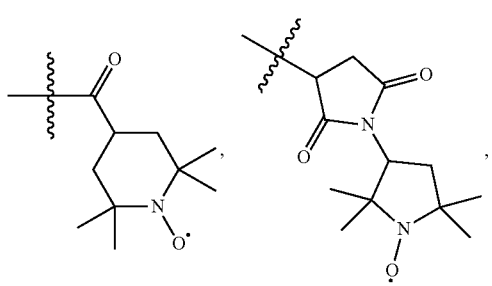
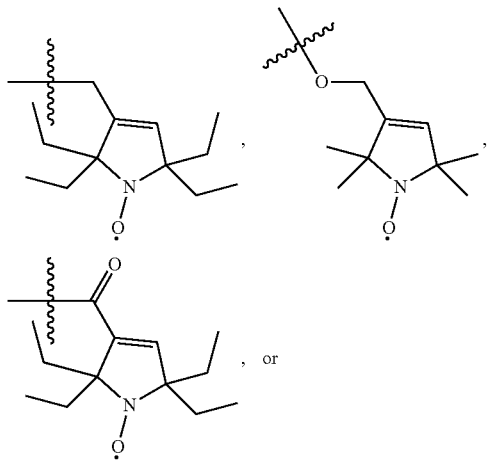
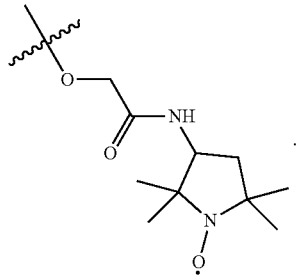
$R^2$ can be propylamine or a nitroxide. The $R^2$ nitroxide can be:
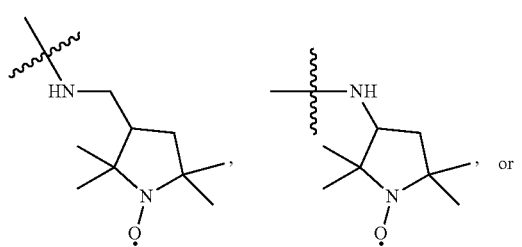
-continued
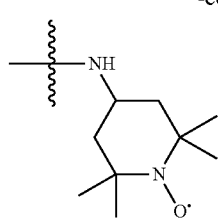
At least one of $R^1$ and $R^2$ is a nitroxide.
In some embodiments, the compound of formula I can be:
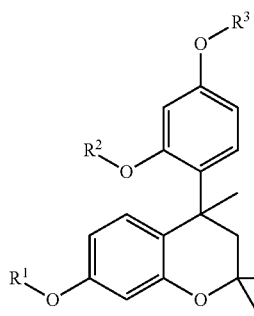
or
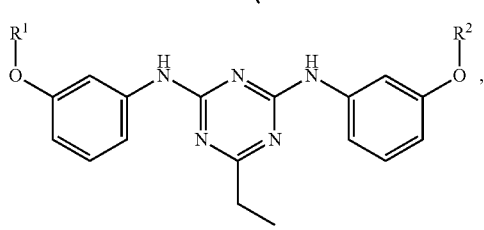
wherein $R^1$, $R^2$, and $R^3$ can each independently be:
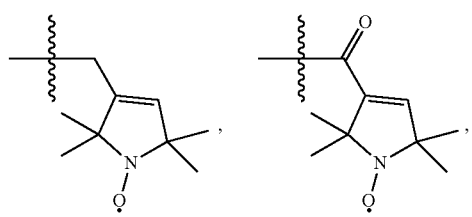
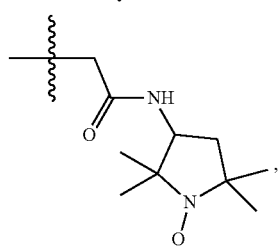
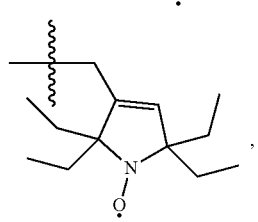

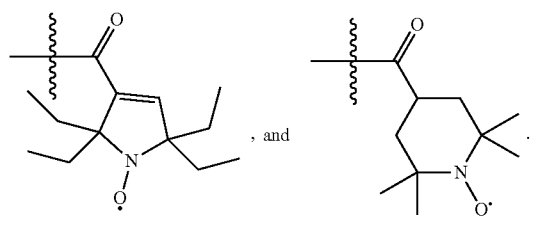, and 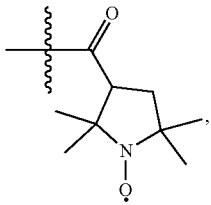.

In some embodiments, the compound of formula I can be:

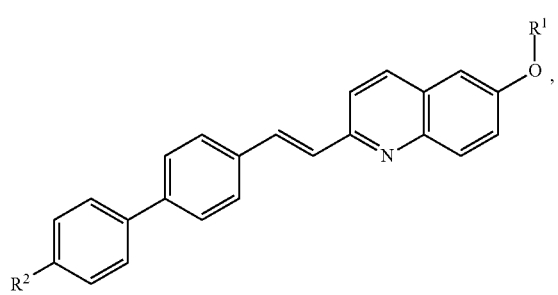,

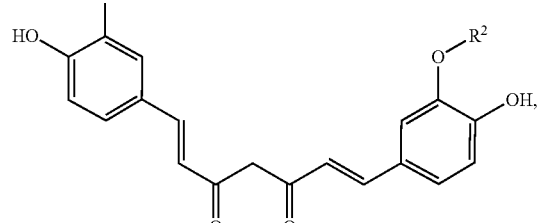,

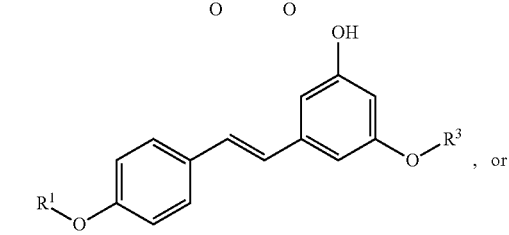, wherein $R^1$ and $R^2$ can each independently be H or a nitroxide. The nitroxide can be:

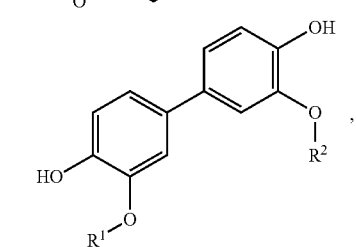,

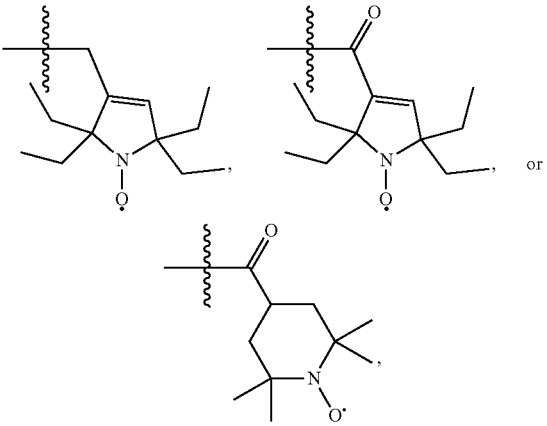

At least one of $R^1$ and $R^2$ is a nitroxide. In some embodiments, the compound of formula I is

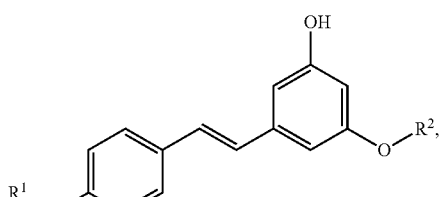

wherein $R^1$ and $R^2$ can each independently be H or a nitroxide. The nitroxide can be:

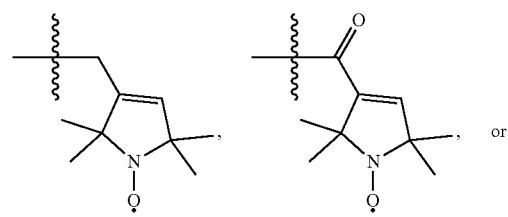,

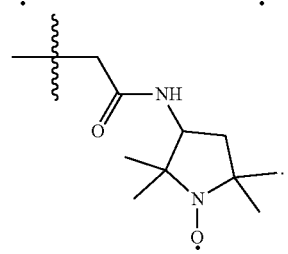.

At least one of $R^1$ and $R^2$ is a nitroxide. In some embodiments, the compound of formula I can be:

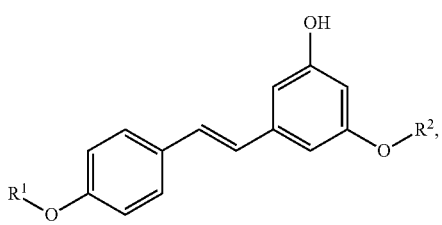
wherein $R^1$ is H and $R^2$ is a nitroxide. The $R^2$ nitroxide can be:
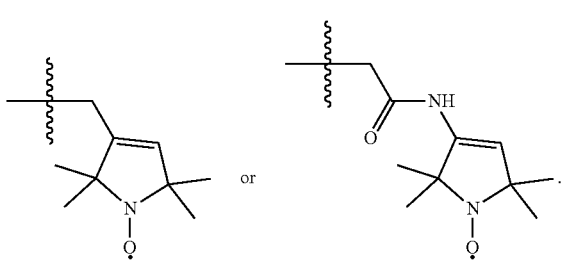
In some embodiments, the compound of formula I can be:
The nitroxide can be:
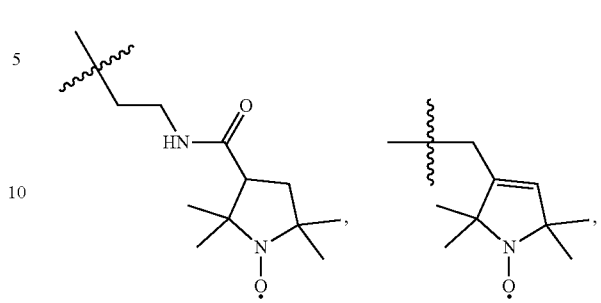
At least one of $R^1$ and $R^2$ is a nitroxide.
In some embodiments, the compound of formula I can be:
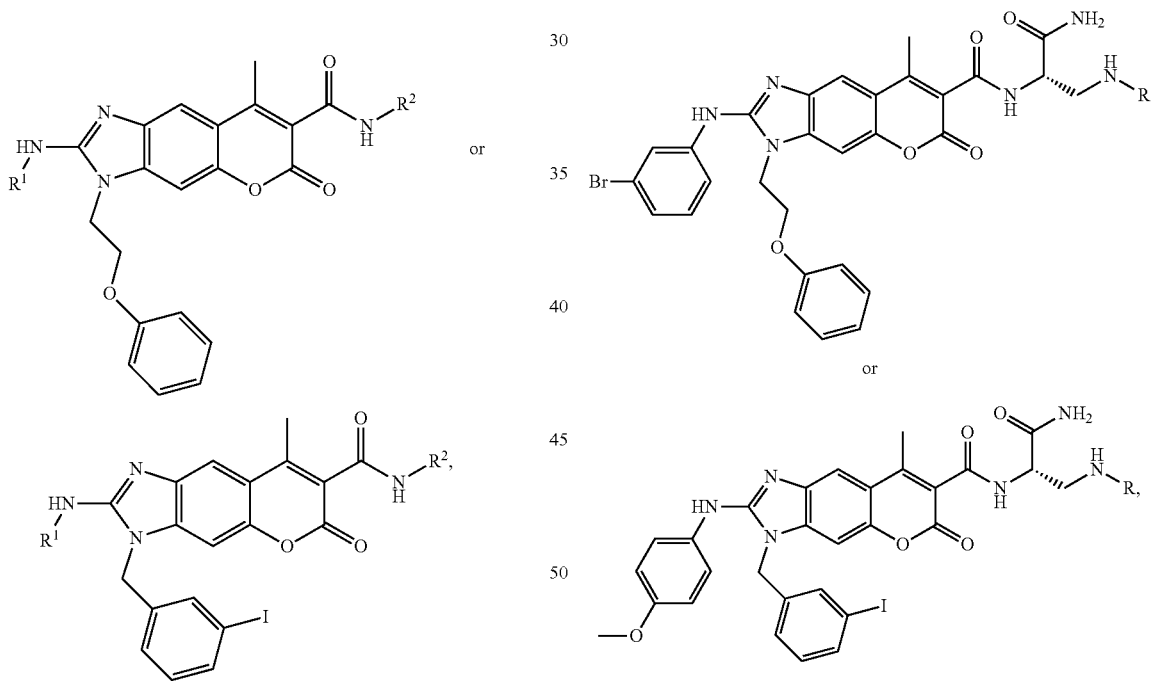
wherein $R^1$ and $R^2$ can each independently be H,
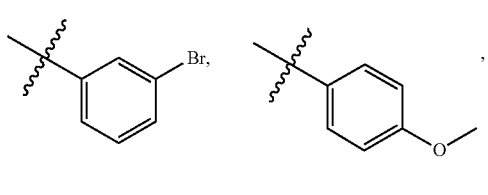
or a nitroxide.
wherein R can be
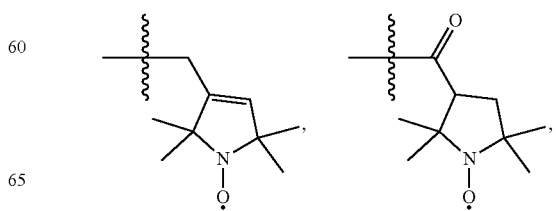

-continued

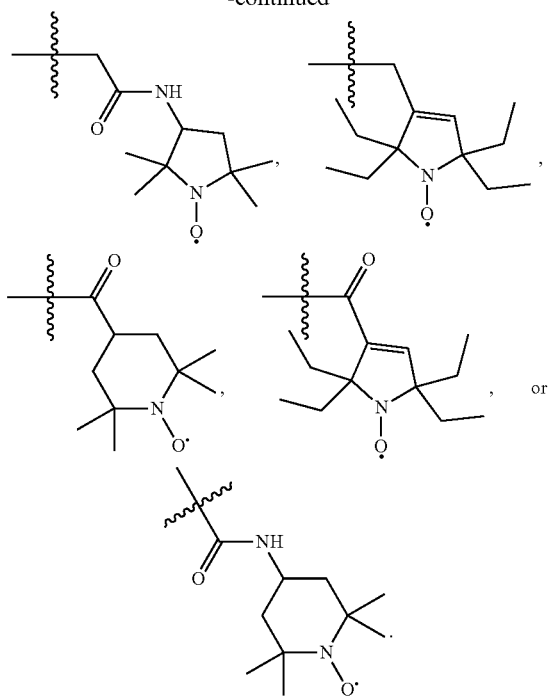

In some embodiments, the compound of formula I has the structure:

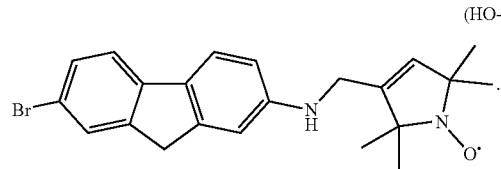
(HO-4160)

In some embodiments, the compound of formula I can be:

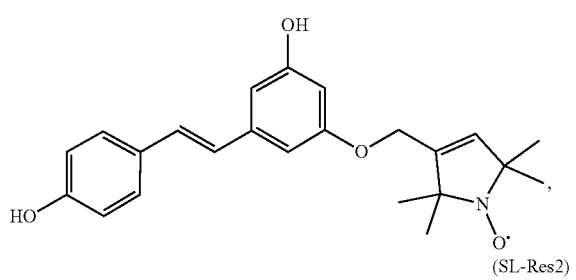
(SL-Res1)

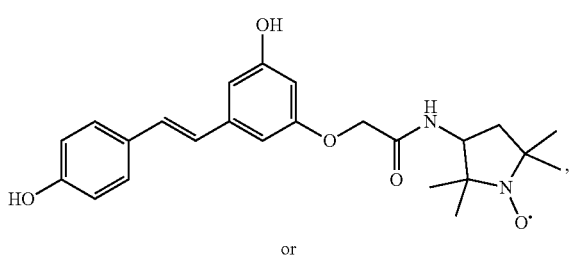
(SL-Res2)

or

-continued

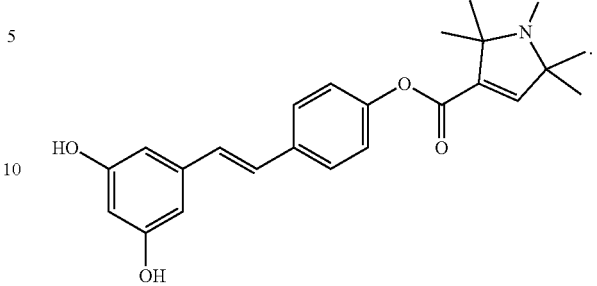
(SL-Res3)

In some embodiments, the compound of formula I can be:

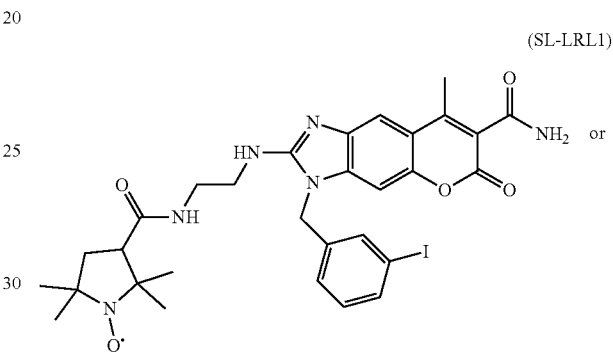
(SL-LRL1)

or

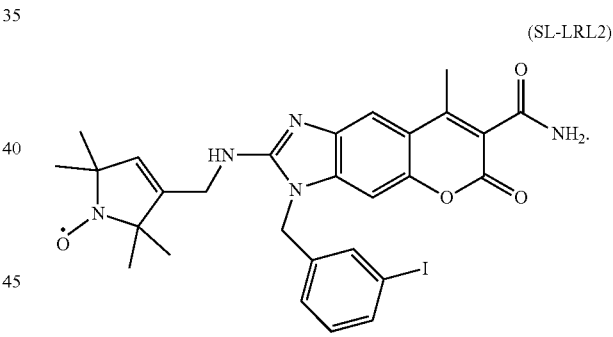
(SL-LRL2)

In some embodiments, the compound of formula I binds to extracellular amyloid. In some embodiments, the compound binds to intraneuronal amyloid. The compounds of formula I can be designed to be resistant to chemical reduction. For example, the nitroxide group of the compound can comprise tetraethyl ring substitutions in place of tetramethyl substitutions. The tetraethyl substitutions can decrease the rate at which the N-O moiety of the nitroxide group reacts with intracellular reductants subsequent to administering the compound.

IV. Compounds

In some embodiments, the present invention provides several nitroxide spin labeled amyloid binding compounds. In some embodiments, the present invention provides compounds having the structure

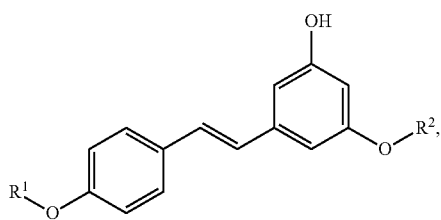

(II)

wherein $R^1$ and $R^2$ of formula II can each independently be H or a nitroxide. The nitroxide can be

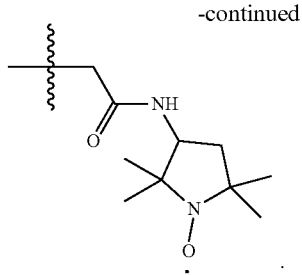

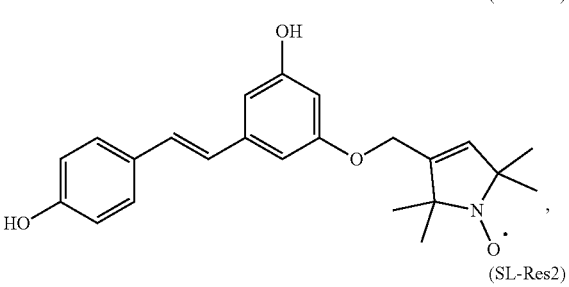

At least one of $R^1$ and $R^2$ is a nitroxide.

In some embodiments $R^1$ and $R^2$ of formula II are each independently a nitroxide. In some embodiments, $R^1$ is H and $R^2$ is a nitroxide. In some embodiments, $R^1$ is a nitroxide and $R^2$ is H.

In some embodiments, $R^1$ and $R^2$ of formula II can each independently be H or a nitroxide. The nitroxide can be

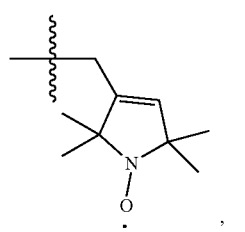

In some embodiments, the compound of formula II can be:

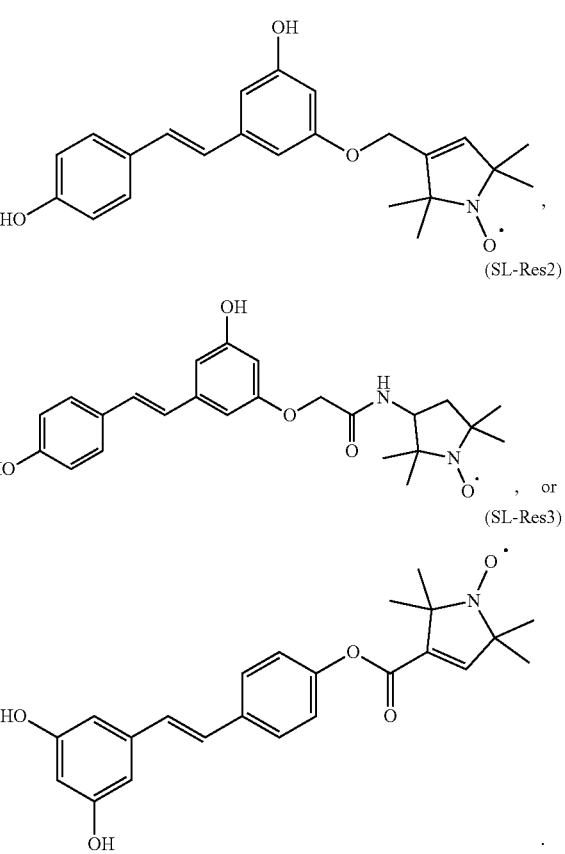

In some embodiments, the compound of formula II can be:

(SL-Res1)

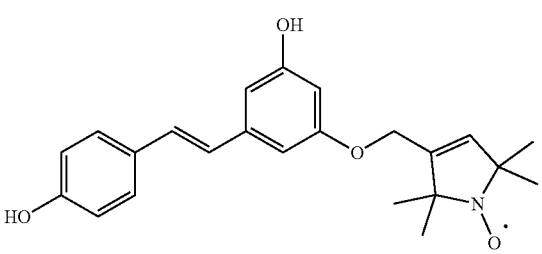

In some embodiments, the compound of formula II can be:

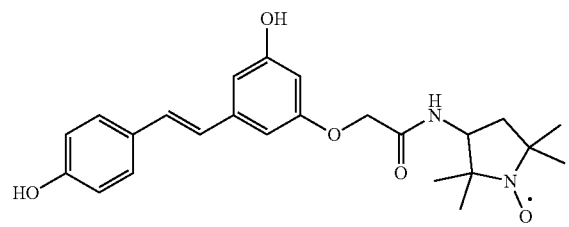

(SL-Res2)

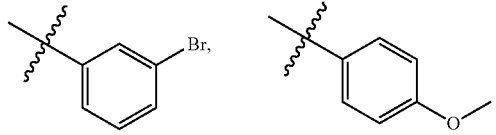

or a nitroxide. The nitroxide can be

In some embodiments, the compound of formula II can be:

(SL-Res3)

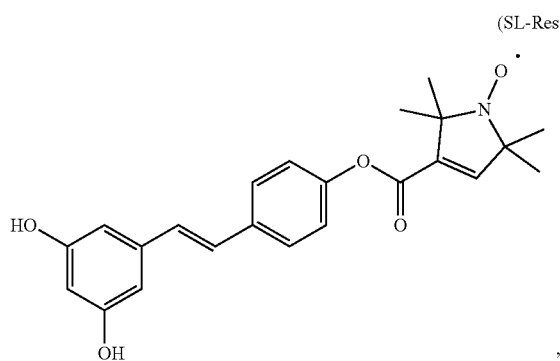

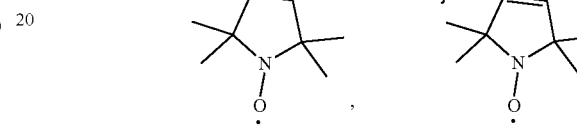

In some embodiments, the present invention provides compounds having the structure

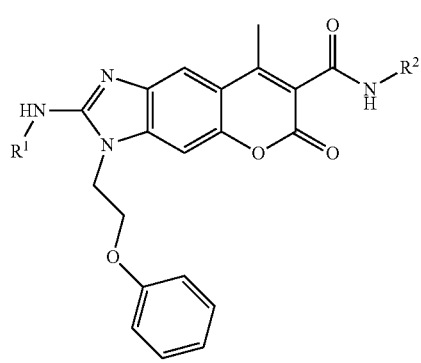

(III)

At least one of $R^1$ and $R^2$ is a nitroxide.

In some embodiments $R^1$ and $R^2$ of formula III and IV are each independently a nitroxide. In some embodiments, $R^1$ is H

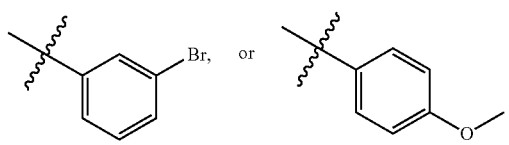

or (IV)

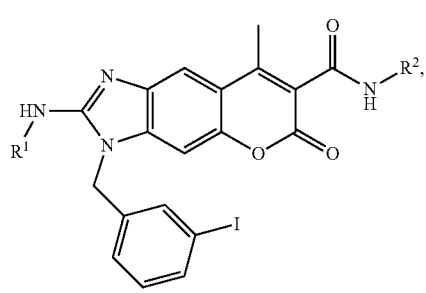

and $R^2$ is a nitroxide.

In some embodiments, $R^1$ is a nitroxide and $R^2$ is H,

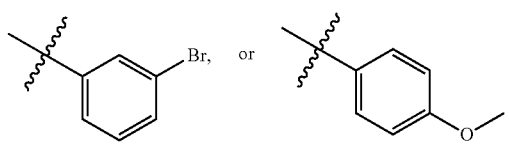

wherein $R^1$ and $R^2$ of formulas III and IV can each independently be H,

In some embodiments, $R^1$ and $R^2$ of formulas III and IV can each independently be H,

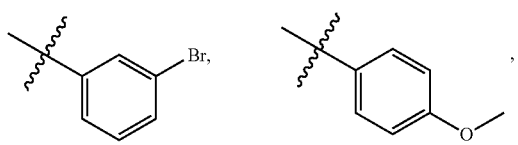

or a nitroxide. The nitroxide can be

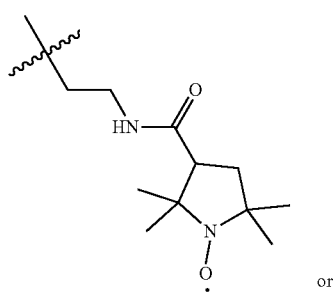

or

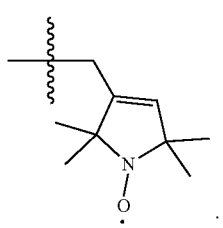

At least one of $R^1$ and $R^2$ is a nitroxide.

In some embodiments, the compound of formula IV can be:

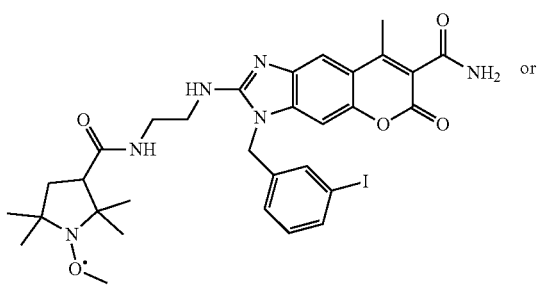
(SL-LRL1)

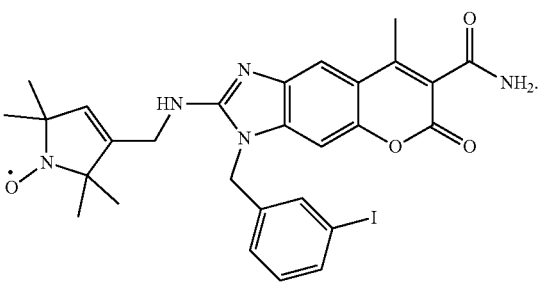
(SL-LRL2)

In some embodiments, the compound of formula IV can be:

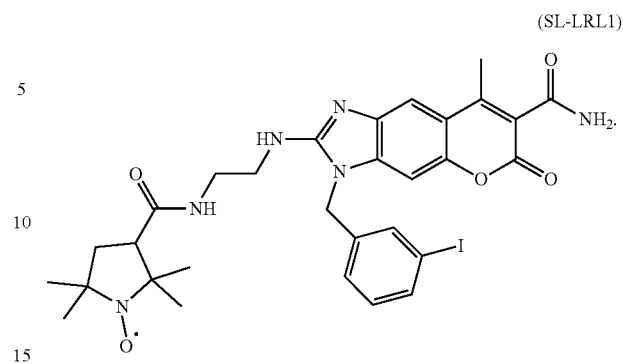
(SL-LRL1)

In some embodiments, the compound of formula IV can be:

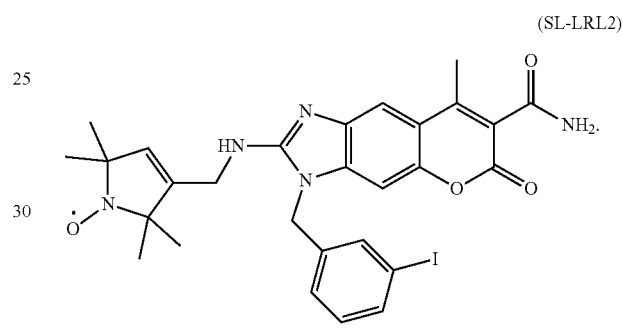
(SL-LRL2)

In some embodiments, the present invention provides compounds having the structure

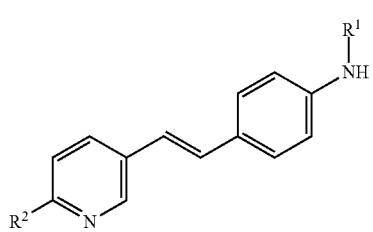
(V)

wherein $R^1$ can be

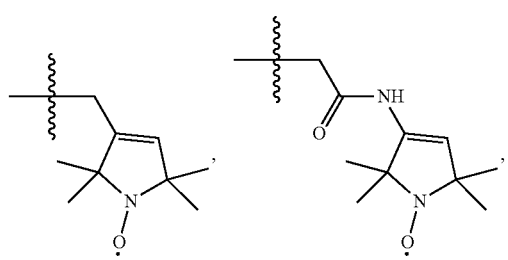

-continued
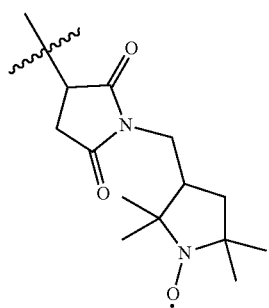
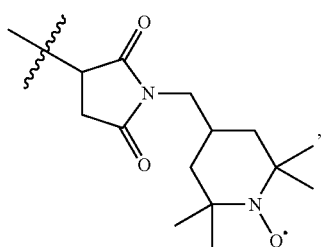
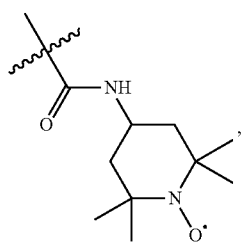
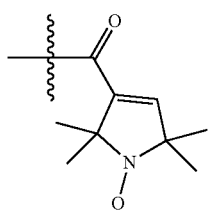
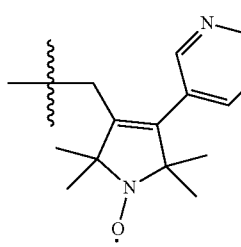
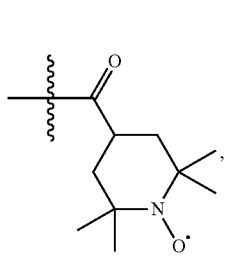 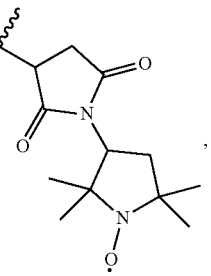
-continued
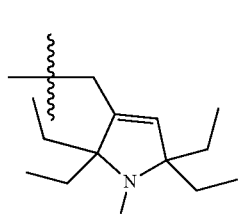 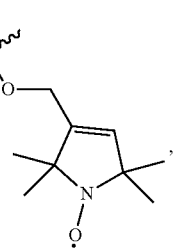
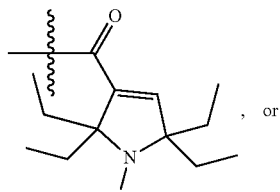, or
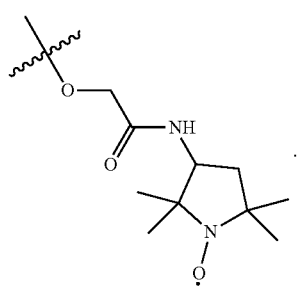
$R^2$ can be OH, $OCH_3$, $OCH_2CH_3$, $OCH_2CH_2F$, $CH_3$, or $(OCH_2CH_2)_3F$.
In some embodiments, the present invention provides compounds having the structure
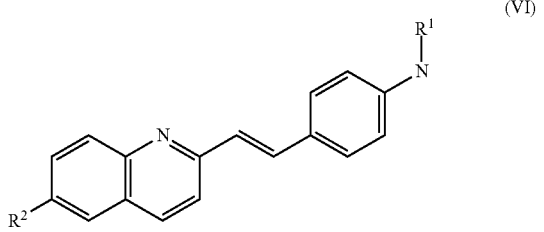
(VI)
wherein $R^1$ can be
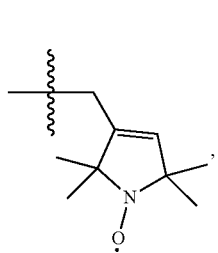 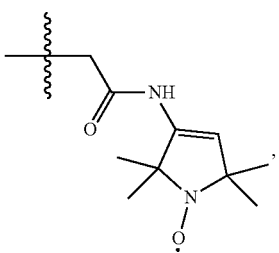

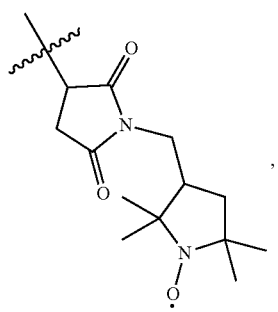
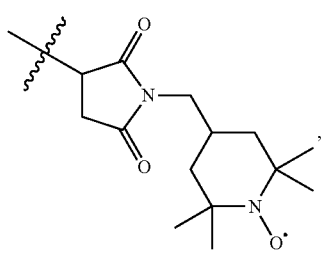
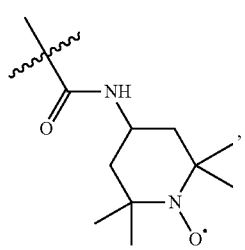
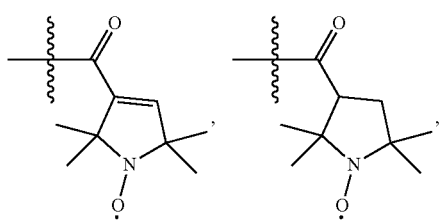
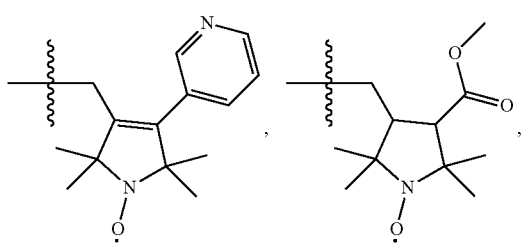
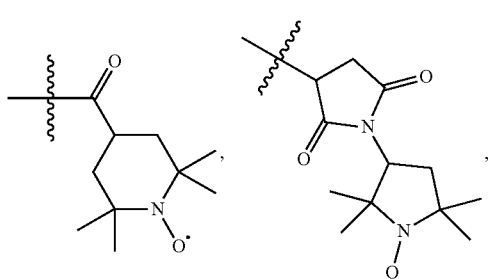
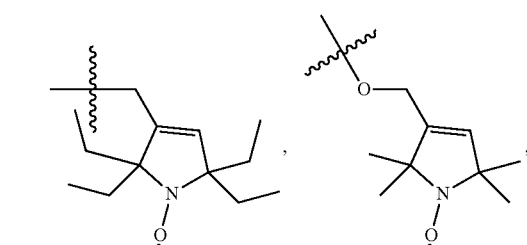
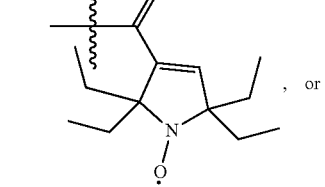
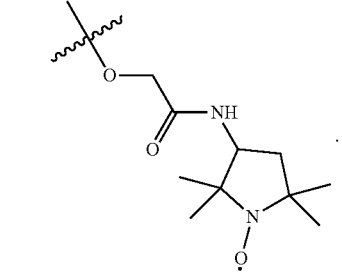
$R^2$ can be OH, OCH$_3$, OCH$_2$CH$_3$, OCH$_2$CH$_2$F, CH$_3$, or (OCH$_2$CH$_2$)$_3$F. In other embodiments, $R^2$ can be OH, Me, OCH$_3$, OCH$_2$CH$_3$, OCH$_2$CH$_2$F, CH$_3$, or (OCH$_2$CH$_2$)$_3$F.
In some embodiments, the present invention provides compounds having the structure
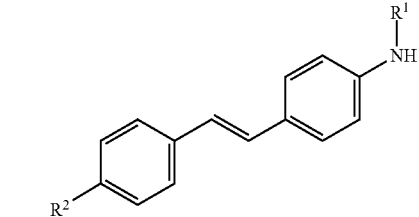
(VII)
wherein $R^1$ can be
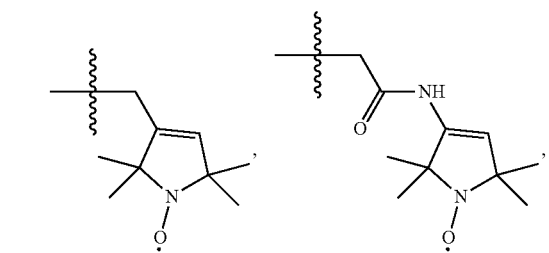

-continued
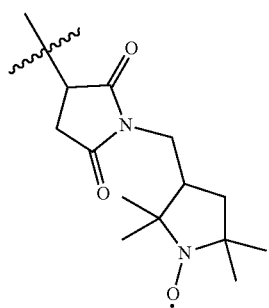
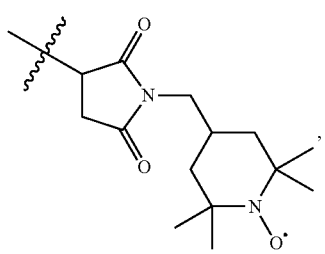
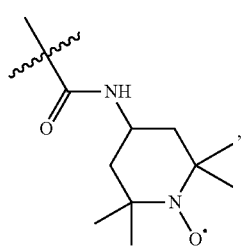
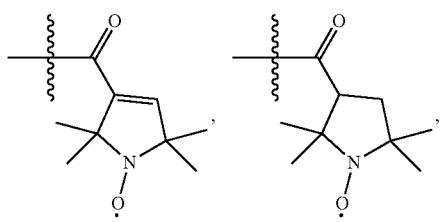
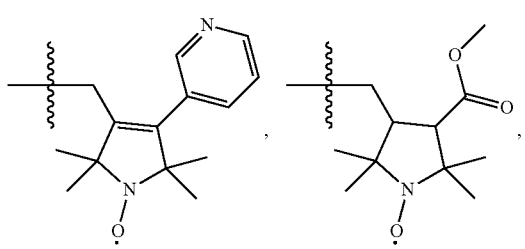
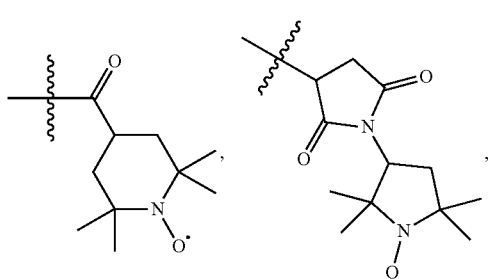
-continued
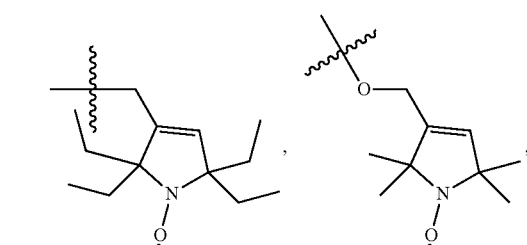
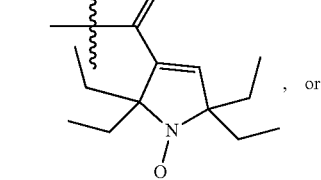
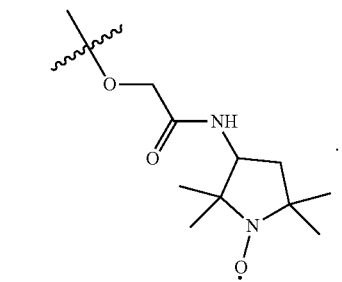
$R^2$ can be OH, $OCH_3$, $OCH_2CH_3$, $OCH_2CH_2F$, $CH_3$, or $(OCH_2CH_2)_3F$. In other embodiments, $R^2$ can be OH, Me, $OCH_3$, $OCH_2CH_3$, $OCH_2CH_2F$, $CH_3$, or $(OCH_2CH_2)_3F$.
In some embodiments, the present invention provides compounds having the structure
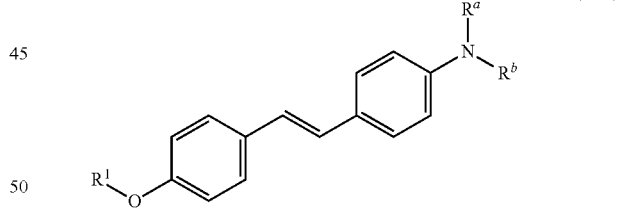
(VIII)
wherein $R^1$ can be
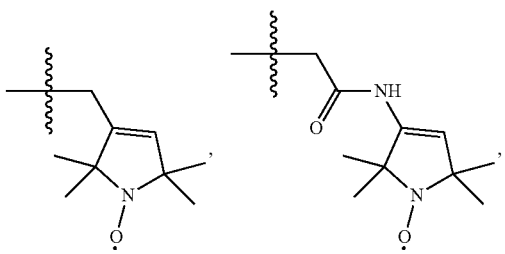

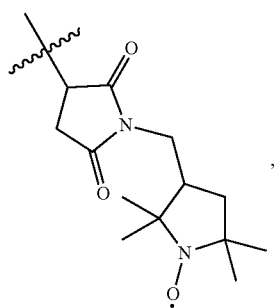
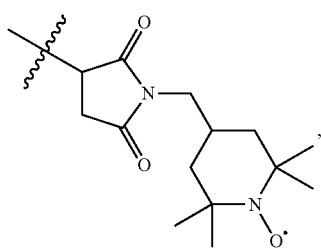
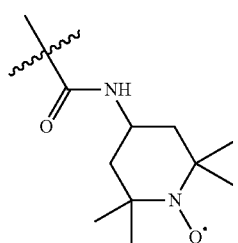
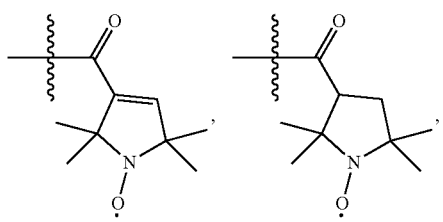
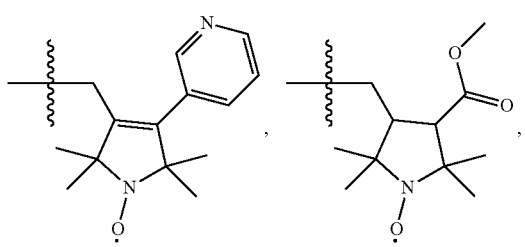
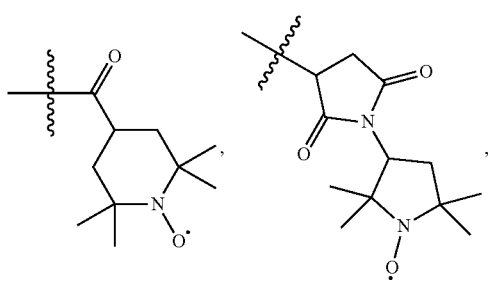
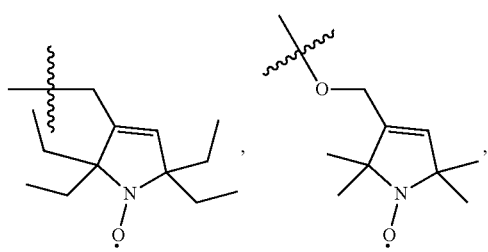
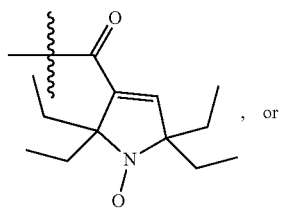
, or
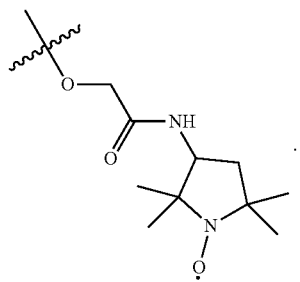
$R^a$ and $R^b$ can each independently be H and $C_{1-4}$ alkyl.
In some embodiments, the present invention provides compounds having the structure
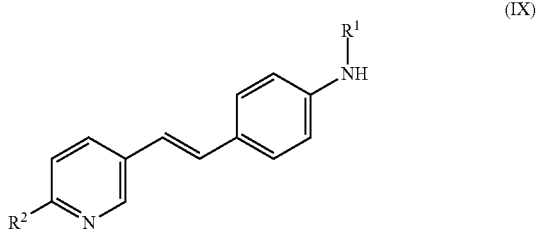
(IX)
wherein $R^1$ can be
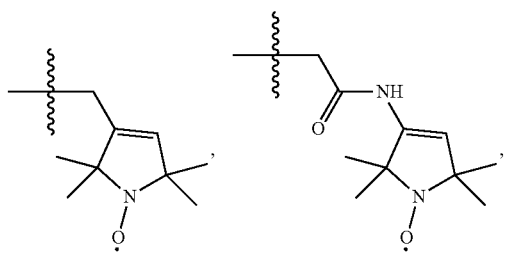

-continued
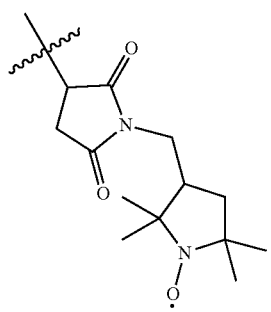
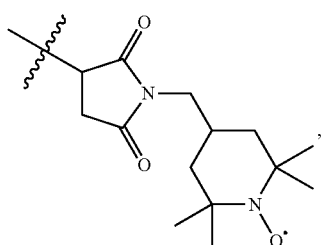
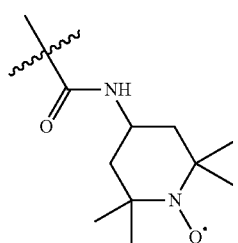
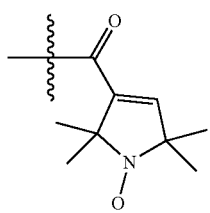
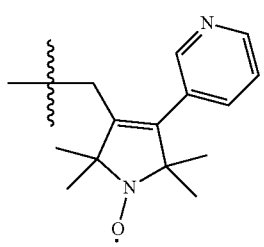
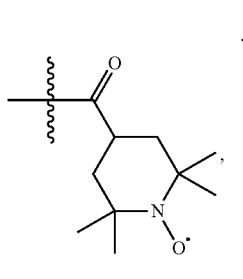
-continued
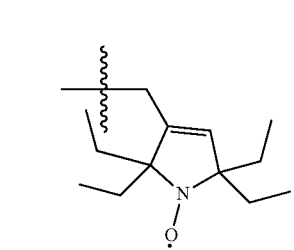
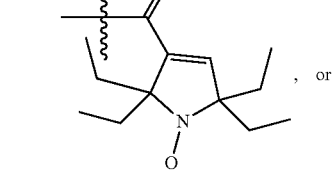
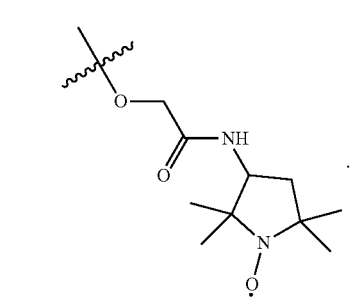
$R^2$ can be OH, OCH$_3$, OCH$_2$CH$_3$, OCH$_2$CH$_2$F, CH$_3$, or (OCH$_2$CH$_2$)$_3$F. In other embodiments, $R^2$ can be OH, Me, OCH$_3$, OCH$_2$CH$_3$, OCH$_2$CH$_2$F, CH$_3$, or (OCH$_2$CH$_2$)$_3$F.
In some embodiments, the compound can be
(SL-G8)
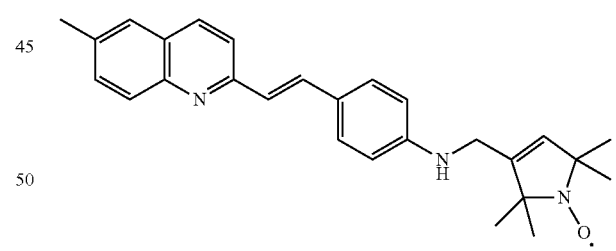
(SL-Sb1)
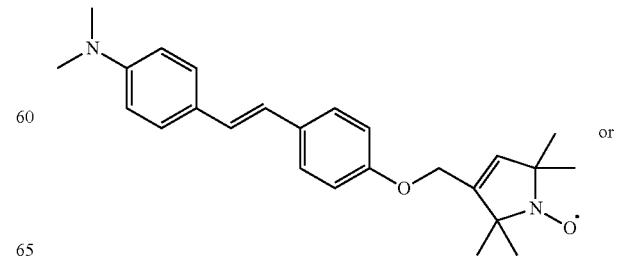

-continued (SL-Sb2)

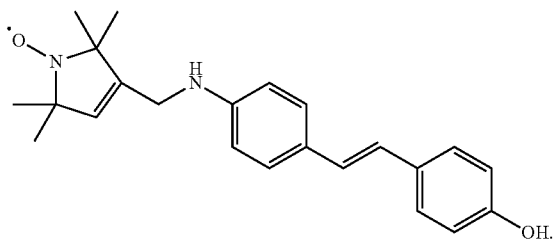

In some embodiments, the compound can be

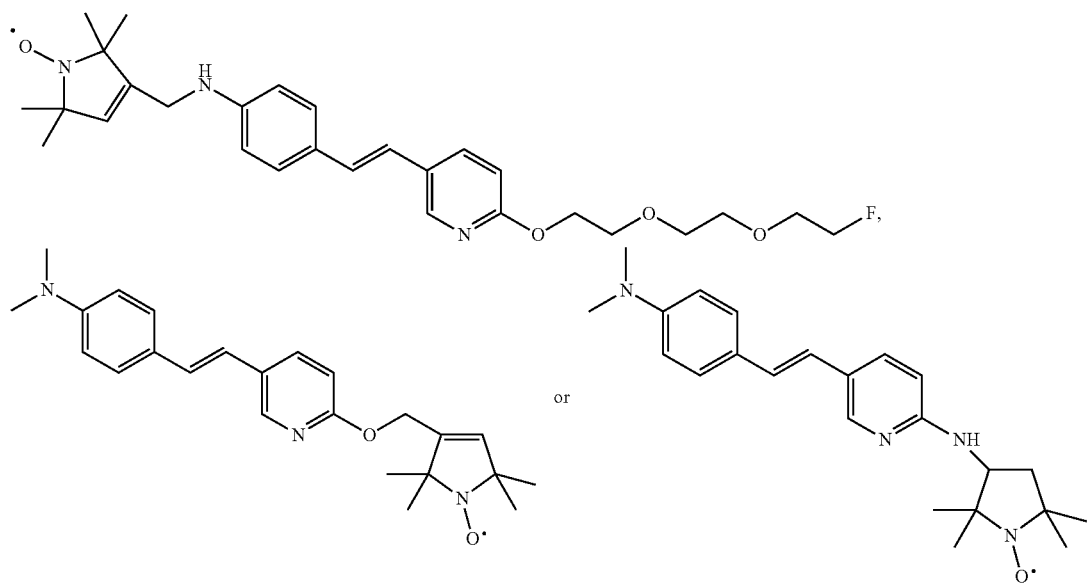

The compounds of the present invention can also be the salts and isomers thereof. In some embodiments, the compounds of the present invention include the salt forms thereof. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid. These salts may be prepared by methods known to those skilled in art. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain basic acidic functionalities that allow the compounds to be converted into base addition salts. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

Isomers include compounds having the same number and kind of atoms, and hence the same molecular weight, but differing in respect to the structural arrangement or configuration of the atoms.

It will be apparent to one skilled in the art that certain compounds of this invention may exist in tautomeric forms, all such tautomeric forms of the compounds being within the scope of the invention. Tautomer refers to one of two or more structural isomers which exist in equilibrium and which are readily converted from one isomeric form to another.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, the compounds of the present invention may also contain unnatural proportions of atomic isotopes at one or more of the atoms that constitute such compounds. For example, the compounds of the present invention may be radiolabeled with radioactive isotopes, such as for example deuterium ($^2$H), tritium ($^3$H), iodine-125 ($^{125}$I), carbon-13 ($^{13}$C), or carbon-14 ($^{14}$C). All isotopic variations of the compounds of the present invention, whether radioactive or not, are encompassed within the scope of the present invention.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see *Comprehensive Organic Transformations* Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention. Although some compounds described may indicate relative stereochemistry, the compounds may exist as a racemic mixture or as either enantiomer.

In general, some compounds of this invention can be synthesized by alkylation of amyloid beta-binding compounds with a spin-labeled nitroxide compound. The alkylation can be, for example, with commercially available 3-bromomethyl-2,5-dihdrydro-2,2,5,5-tetramethyl-1H-pyrrol-1-yloxy (RBr). The alkylation can be an N-alkylation in the presence of a base. In some embodiments, the base is triethylamine (TEA). The alkylation can be a reductive alkylation in the presence of a reducing agent. In some embodiments, the reducing agent is sodium triacetoborohydride.

V. Administration

The present invention provides diagnostic compositions for imaging amyloid. The compositions include a compound having the structure:

$$X-(Y)_n \qquad (I)$$

wherein X of formula I is an amyloid beta binding protein, Y is a nitroxide, and n is an integer from 1 to 3. The compounds and compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds and compositions of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds and compositions of the present invention can be co-administered with other agents. Co-administration includes administering the compound or composition of the present invention within 0.5, 1, 2, 4, 6, 8, 10, 12, 16, 20, or 24 hours of the other agent. Co-administration also includes administering simultaneously, approximately simultaneously (e.g., within about 1, 5, 10, 15, 20, or 30 minutes of each other), or sequentially in any order. Moreover, the compounds and compositions of the present invention can each be administered once a day, or two, three, or more times per day so as to provide the preferred dosage level per day.

In some embodiments, co-administration can be accomplished by co-formulation, i.e., preparing a single pharmaceutical composition including the compounds and compositions of the present invention and any other agent. Alternatively, the various components can be formulated separately.

The compounds and compositions of the present invention, and any other agents, can be present in any suitable amount, and can depend on various factors including, but not limited to, weight and age of the subject, disease state of the subject, etc. Suitable dosage ranges include from about 0.1 mg to about 10,000 mg, or about 1 mg to about 1000 mg, or about 10 mg to about 750 mg, or about 25 mg to about 500 mg, or about 50 mg to about 250 mg. Suitable dosages also include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

VI. Formulations

The compounds of the present invention can be prepared in a wide variety of oral, parenteral and topical dosage formulations. Oral preparations include tablets, pills, powder, dragees, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, intraperitoneally, intracerebrally, intrathecally, intraspinally, or intra-arterially. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi 1995 *J. Clin. Pharmacol.* 35:1187 and Tjwa 1995 *Ann. Allergy Asthma Immunol.* 75:107). Accordingly, the present invention also provides pharmaceutical compositions including a pharmaceutically acceptable carrier or excipient and a compound of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain the compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compounds of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto 1997 *J. Pharmacol. Exp. Ther.* 281:93. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao 1995 *Biomater Sci. Polym. Ed.* 7:623); as biodegradable and injectable gel formulations (see, e.g., Gao 1995 *Pharm. Res.* 12:857); or, as microspheres for oral administration (see, e.g., Eyles 19971 *J. Pharm. Pharmacol.* 49:669). Both transdermal and intradermal routes afford constant delivery for weeks or months.

In another embodiment, the compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed 1996 *J. Microencapsul.* 13:293; Chonn 1995 *Curr. Opin. Biotechnol.* 6:698; and Ostro 1989 *Am. J. Hosp. Pharm.* 46:1576).

Lipid-based drug delivery systems include lipid solutions, lipid emulsions, lipid dispersions, self-emulsifying drug delivery systems (SEDDS) and self-microemulsifying drug delivery systems (SMEDDS). In particular, SEDDS and SMEDDS are isotropic mixtures of lipids, surfactants and co-surfactants that can disperse spontaneously in aqueous media and form fine emulsions (SEDDS) or microemulsions (SMEDDS). Lipids useful in the formulations of the present invention include any natural or synthetic lipids including, but not limited to, sesame seed oil, olive oil, castor oil, peanut oil, fatty acid esters, glycerol esters, Labrafil®, Labrasol®, Cremophor®, Solutol®, Tween®, Capryol®, Capmul®, Captex®, and Peceol®.

In another embodiment, the formulations of the compositions of the present invention can be delivered by the use of nanoparticles. For example, the use of spin-labeled fluorophores is discussed in Li et al. (2012) *ACS Nano.* 6:9485. Nanoparticles have emerged as a major class of vehicles to deliver conventional anticancer drugs. Nanoparticle drug delivery systems offer several distinct advantages, such as controlled release and prolonged circulation time, as well as passive and active tumor targeting (Cabral et al. (2011) *Nat. Nanotechnol.* 6:815; Gref et al. (1994) *Science* 263:1600; Liu and Allen (2006) *Curr. Pharm.* 12:4685; and Li et al. (2009) *Nanotechnology* 20:065104). In some embodiments, the nitroxide spin-labeled compound is hydrophobic and can be easily loaded inside a nanomicelle. The nanomicelle can comprise non-crosslinked micellar nanoparticles (NCMN). The nanomicelle can comprise disulfide-crosslinked micellar nanoparticles (DCMN). In some embodiments, the surface of a nanoparticle is decorated with one or more copies of a brain-targeting molecule. The brain-targeting molecule can be, for example, apolipoprotein E (apoE).

In some embodiments, the formulations of the compositions of the present invention comprise solubility aids. The solubility aid can be, for example, a cyclodextrin. The use of cyclodextrins as solubility aids for highly water-insoluble steroids is discussed in U.S. Patent Application Publication Nos. US 2015/0018327 and US 2015/0313915. The cyclodextrin can be, for example, a β-cyclodextrin. In some embodiments, the cyclodextrin is a sulfo butyl ether β-cyclodextrin.

VII. Methods of Treating a Disorder

In some embodiments, the present invention provides a method of treating a disorder, the method including administering to a subject in need of such treatment, a therapeutically effective amount of a compound of the present invention, thereby treating the disorder. In some embodiments, a compound of the present invention is a nitroxide spin-labeled amyloid beta-binding compound useful for treating or ameliorating Alzheimer's disease. The agent can be given with an aim to prolong life or for the purpose of reducing symptoms. In some embodiments, treatment with an effective amount of a nitroxide spin-labeled amyloid beta-binding compound disrupts the aggregation of proteins to form amyloid. In some embodiments, the disruption prevents the formation of new oligomers, plaques, or fibrils. In some embodiments, the disruption alters the structure of existing oligomers plaques, or fibrils.

Examples of disorders or conditions suitable for use with the present invention include, but are not limited to, Alzheimer's disease, diabetes, Parkinson's disease, spongiform encephalopathy, Huntington's disease, thyroid carcinoma, atrial amyloidosis, atherosclerosis, arthritis, prolactinomas, polyneuropathy, corneal dystrophy, or cerebral amyloid angiopathy.

VIII. Examples

Example structures below are named according to standard IUPAC nomenclature using the CambridgeSoft ChemDraw naming package.

Example 1. SL-Res1. (E)-3-(4-hydroxystyryl)-5-((2,2,5,5-tetramethyl-1-oxyl-2,5-dihydro-1H-pyrrol-3-yl)methoxy)phenol Radical

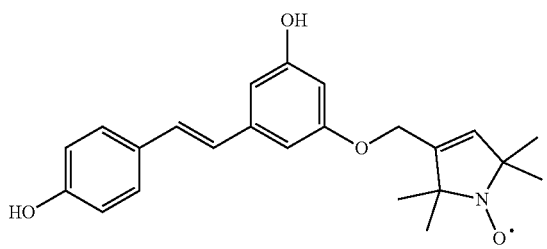

Synthesis was as shown in FIG. 1. To an 1.5 mL eppendorf tube was added resveratrol 3,4'-diacetate (Toronto Research Chemicals, Toronto, Canada, 8.3 mg, 0.0266 mmol), 3-hydroxymethyl-(1-oxy-2,2,5,5-tetramethylpyrroline) (5 mg, 0.0294 mmol), triphenylphosphine (PPh$_3$, 8.0 mg, 0.0305 mmol), and anhydrous tetrahydrofuran (THF, 0.2 mL). The reaction tube was then lowered into a 42-kHz sonication bath (Cole-Parmer) and sonicated for 2 min. While sonicating, diisopropyl azodicarboxylate (DIAD, 6.6 µL, 0.0335 mmol) was added to the reaction mixture. The reaction mixture was sonicated for 25 min. The reaction mixture was added to KOH solution (20 µL, 10% aqueous solution) and then stirred for 30 min at room temperature. The solution was neutralized with 0.05% trifluroacetic acid (TFA) in acetonitrile and then submitted for purification with preparative reversed-phase high performance liquid chromatography (HPLC). The eluent was collected and lyophilized to give powder SL-Res 1.

HPLC was performed on a System Gold 126NMP solvent module (Beckman) with a C18 column (Vydac, 10 µm, 2.2 cm i.d.×25 cm). A gradient elution of 25-100% B over 46 min was used at a flow rate of 5 mL/min (solvent A, H$_2$O/0.1% TFA; B, acetonitrile/0.1% TFA). The chemical identity was confirmed with Orbitrap ESI-MS, with a calculated mass for $C_{23}H_{26}NO_4$ of 380.19, and observed mass of 381.20 and 382.20.

Example 2. SL-Res2. (E)-2-(3-hydroxy-5-(4-hydroxystyryl)phenoxy)-N-(2,2,5,5-tetramethyl-1-oxylpyrrolidin-3-yl)acetamide Radical

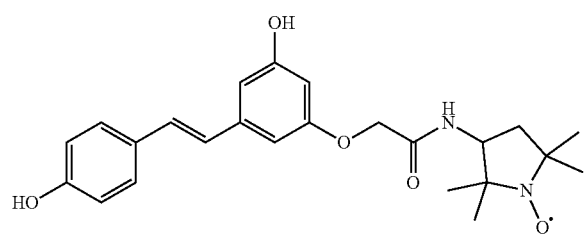

Figure 2:
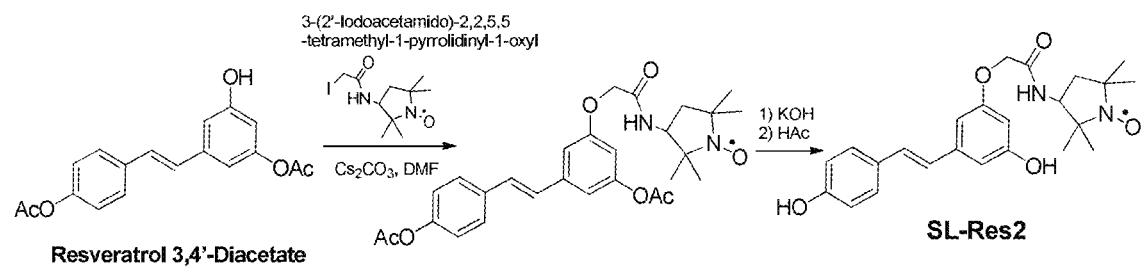
FIG. 2 shows a scheme for the synthesis of the nitroxide spin-labeled compound SL-Res2.

Synthesis was as shown in FIG. 2. Cs$_2$CO$_3$ (20 mg, 0.0624 mmol) was added to a solution of resveratrol 3,4'-diacetate (13 mg, 0.0416 mmol) in anhydrous dimethylformamide (DMF, 1 mL) and the reaction mixture was stirred at room temperature for 45 min. 3-(2'-Iodoacetamido)-2,2,5,5-tetramethyl-1-pyrrolidinyl-1-oxyl (13.5 mg, 0.0415 mmol) was then added to the solution and the resulting mixture was stirred at room temperature overnight. The reaction mixture was added to KOH solution (20 µL, 10% aqueous solution) and then stirred for 30 min at room temperature. The solution was neutralized with 0.05% TFA in acetonitrile and then submitted for HPLC purification using above-mentioned conditions. The eluent was lyophilized to give powder SL-Res2.

The chemical identity was confirmed with Orbitrap ESI-MS, with a calculated mass for $C_{24}H_{29}N_2O_5$ of 425.21, and observed mass of 426.22 and 427.22.

Example 3. SL-Res3. (E)-4-(3,5-dihydroxystyryl)phenyl 2,2,5,5-tetramethyl-1-oxyl-2,5-dihydro-1H-pyrrole-3-carboxylate Radical

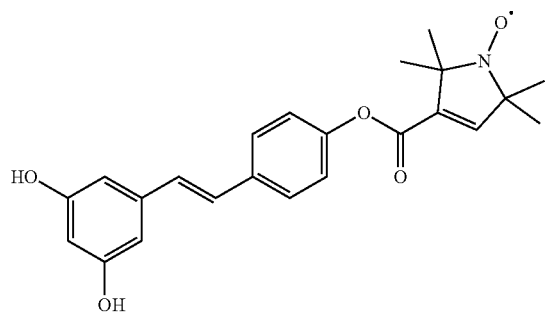

Figure 3:
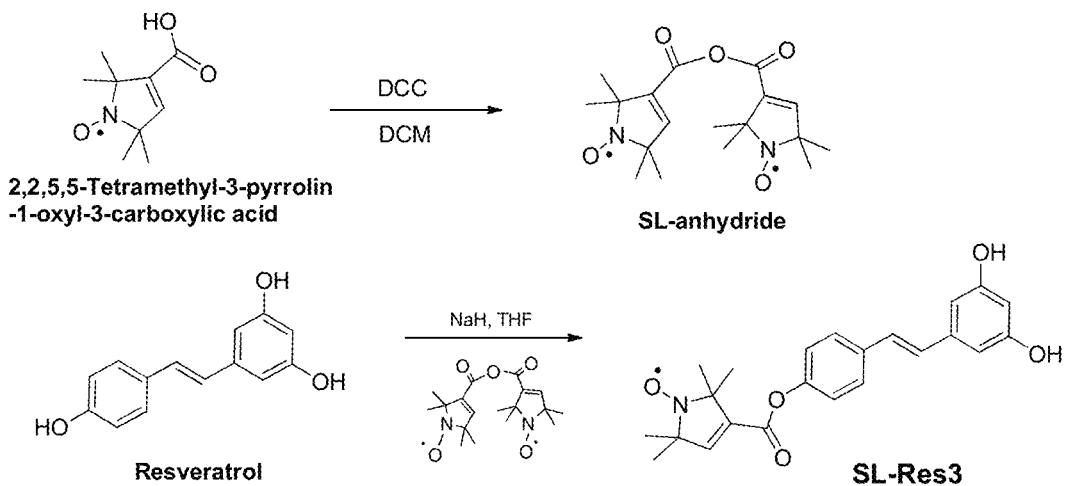
FIG. 3 shows a scheme for the synthesis of the nitroxide spin-labeled compound SL-Res3.

Synthesis was as shown in FIG. 3. 2,2,5,5-Tetramethyl-3-pyrrolin-1-oxyl-3-carboxylic acid anhydride free radical was first prepared by adding N,N'-dicyclohexylcarbodiimide (DCC, 56 mg, 0.271 mmol) to a solution of 2,2,5,5-tetramethyl-3-pyrrolin-1-oxyl-3-carboxylic acid, free radical (100 mg, 0.542 mmol) in anhydrous dichloromethane (3 mL). The mixture was stirred at room temperature for 1 h. The precipitate was filtered out and the clear solution was concentrated and dried over vacuum to the SL-anhydride.

To a solution of resveratrol (25.3 mg, 0.11 mmol) in 1 mL anhydrous dimethyl sulfoxide (DMSO) in round-bottomed flask was added sodium hydride (11 mg, 60% dispersion in mineral oil). The resulting mixture was stirred at room temperature for 20 min, followed by addition of spin-label anhydride (38.5 mg, 0.11 mmol). The reaction solution was stirred at room temperature for 2 h. The reaction was quenched with water (100 µL), then 5 mL of cold water (with 0.1% acetic acid) was added to the solution. The solid was separated by centrifuge and redissolved in 80% acetonitrile in water (with 0.05% TFA) and purified by HPLC as described above.

The chemical identity was confirmed with Orbitrap ESI-MS, with a calculated mass for $C_{23}H_{24}NO_5$ of 394.16, and observed mass of 395.18 and 396.18.

Example 4. SL-LRL1. 3-3-iodobenzyl)-8-methyl-6-oxo-2-((2-(2,2,5,5-tetramethyl-1-oxylpyrrolidine-3-carboxamido)ethyl)amino)-3,6-dihydrochromeno[6,7-d]imidazole-7-carboxamide Radical

Example 5. SL-LRL2. 3-(3-iodobenzyl)-8-methyl-6-oxo-2-(((2,2,5,5-tetramethyl-1-oxyl-2,5-dihydro-1H-pyrrol-3-yl)methyl)amino)-3,6-dihydrochromeno[6,7-d]imidazole-7-carboxamide Radical

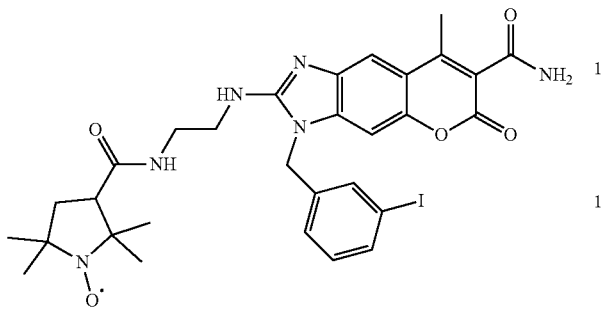

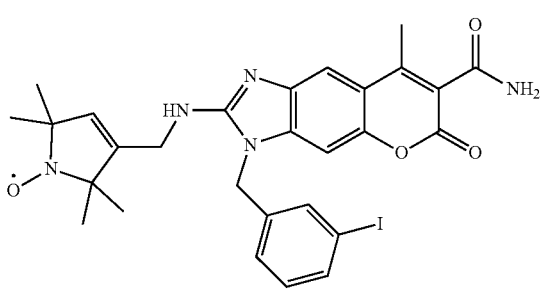

Figure 4:
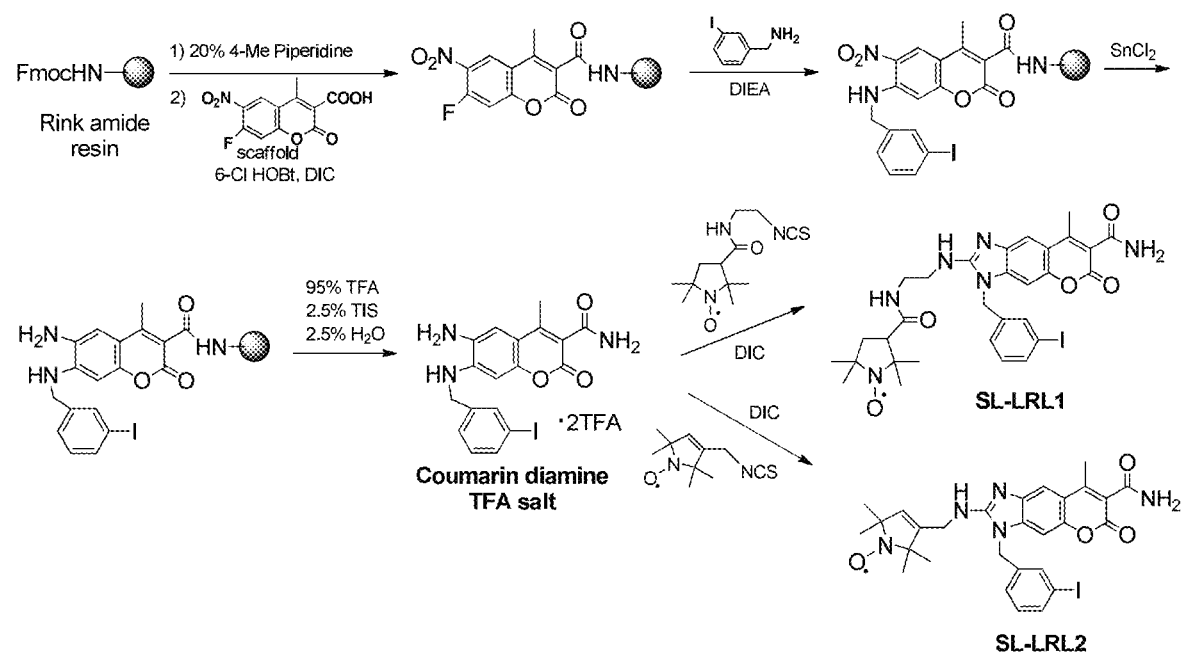
FIG. 4 shows a scheme for the synthesis of the nitroxide spin-labeled compounds SL-LRL1 and SL-LRL2.

Synthesis was as shown in FIG. 4. Synthesis of SL-LRL1 and SL-LRL2 were achieved by cyclization of coumarin diamine with spin label isothiocyanates. The coumarin diamine TFA salt was synthesized on Rink amide MBHA resin (0.503 mmol/g loading) and cleaved off with TFA. Briefly, Fmoc was removed from 0.2 g of Rink resin with 20% 4-methylpiperidine in DMF (5 min, then 15 min). After washing with DMF (×3), methanol (MeOH, ×3) and DMF (×3), 7-fluoro-4-methyl-6-nitro-2-oxo-2H-chromene-3-carboxylic acid (scaffold, 80.2 mg, 0.3 mmol) was coupled to Rink resin in presence of 6-Cl HOBt (50.9 mg, 0.3 mmol) and N,N'-diisopropylcarbodiimide (DIC, 46 µL, 0.3 mmol) in DMF. The reaction was rotated at room temperature until Kaiser test was negative. After filtration, the beads were washed with DMF (×3), MeOH (×3) and DMF (×3). 3-iodobenzylamine (53.6 µL, 0.4024 mmol) and diisopropylethylamine (DIEA, 140 µL, 0.8048 mmol) in DMF was added to the beads and rotated overnight. After washing, the $NO_2$ reduction was achieved with 5 mL of 2 M $SnCl_2 \cdot 2H_2O$ solution in DMF for 1-2 days, twice. After thorough washing with DMF, MeOH and dichloromethane, the beads were dried over vacuum before the coumarin diamine was cleaved by TFA (95%)/triisopropylsilane (TIS, 2.5%)/$H_2O$ (2.5%) for 2 h. The coumarin diamine TFA salt was precipitated with cold diethyl ether and washed twice with ether before being dried over vacuum.

To a solution of coumarin diamine TFA salt (20.0 mg, 0.0295 mmol) and DIEA (25.8 µL, 0.148 mmol) in anhydrous DMF (1.0 mL) was added 3-(2-isothiocyanato-ethyl carbamoyl-proxyl, free radical (15 mg, 0.0555 mmol) in anhydrous DMF (0.3 mL). The resulting mixture was stirred at room temperature for 5 min, before DIC (17 µL, 0.11 mmol) was added and stirred for 2 h. Additional DIC (34 µL, 0.22 mmol) was added and the reaction solution was stirred at room temperature overnight. Cold water was added to the solution. The precipitate was collected by centrifuge and the liquid was discarded. The solid was redissolved in 80% acetonitrile in water (with 0.05% TFA) and purified by HPLC as described above.

The chemical identity was confirmed with Orbitrap ESI-MS, with a calculated mass for $C_{30}H_{34}IN_6O_5$ of 685.16, and an observed mass of 686.17.

Synthesis was as shown in FIG. 4. To a solution of coumarin diamine TFA salt (21.5 mg, 0.0317 mmol) and DIEA (22 µL, 0.1268 mmol) in anhydrous DMF (1.2 mL) was added 3-(isothiocyanatomethyl)-2,2,5,5-tetramethyl-2,5-dihydro-1H-pyrrol-1-yloxyl radical (7.5.mg, 0.0355 mmol). The resulting solution was stirred for 5 min, before DIC (11 µL, 0.071 mmol) was added. The reaction solution was stirred at room temperature for 2 h.

Additional DIC (22 µL) was added and the resulting solution was stirred at room temperature overnight. Cold water was added to the solution. The precipitate was collected by centrifuge and the liquid was discarded. The solid was redissolved in 80% acetonitrile in water (with 0.05% TFA) and purified by HPLC as described above.

The chemical identity was confirmed with Orbitrap ESI-MS, with a calculated mass for $C_{28}H_{29}IN_5O_4$ of 626.12, and an observed mass of 627.13.

Example 6. Synthesis of SL-G8

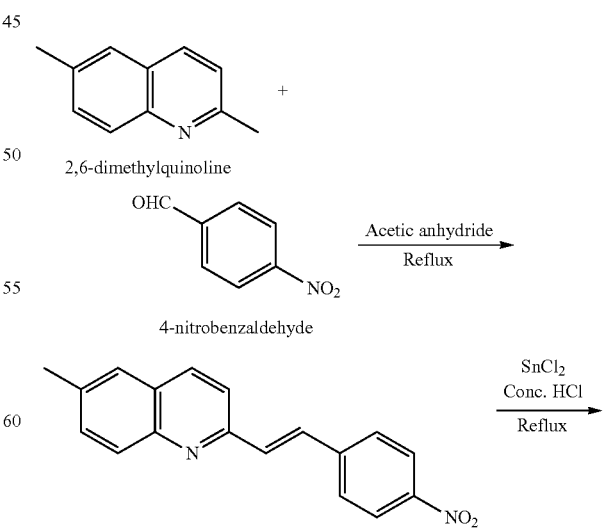

-continued

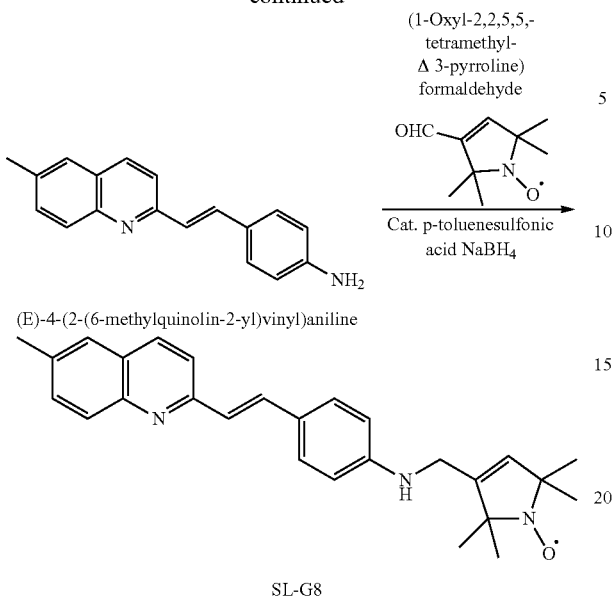

To a 100 mL of round-bottomed bottle was added 2,6-dimethylquinoline (628.8 mg, 4.0 mmol), 4-nitrobenzaldehyde (635 mg, 4.2 mmol), and acetic anhydride (50 mL). The mixture was refluxed for 24 hours. Allow the reaction mixture to cool to room temperature. Yellow crystal was filtered, washed with water followed by aqueous ethanol, and then dried over vacuum to give (E)-6-methyl-2-(4-nitrostyryl)quinolone, 750 mg, yield 64.4%. The chemical identity was confirmed with Orbitrap ESI-MS. Calcd. for $C_{18}H_{14}N_2O_2$: 290.11, found: 291.11.

Nitro reduction was achieved with stannous chloride. Stannous chloride (2.0 g, 10.54 mmol) was added to a solution of (E)-6-methyl-2-(4-nitrostyryOquinoline (612 mg, 2.108 mol) in ethanol (18 mL) followed by the addition of concentrated hydrochloric acid (1.0 mL). The solution was brought to reflux for 5 h and cooled to room temperature stirring overnight. Allow the reaction mixture to cool to room temperature. Dark red solid was collected by filtration and washed with dichloromethane followed by mixture of dichloromethane and ethanol (2:1). The red solid was re-suspended in ethanol (60 mL) and then $K_2CO_3$ aqueous solution was added until the red color disappeared and pH reached 9-10. Water (60 mL) was added to the suspension and mixed. After centrifuge, the solid was collected by filtration and washed with water, 70% ethanol in water and dried over vacuum to give (E)-4-(2-(6-methylquinolin-2-yl)vinyl)aniline as brownish solid, 495 mg, yield 90%. The chemical identity was confirmed with Orbitrap ESI-MS. Calcd. for $C_{18}H_{16}N_2$: 260.13, found: 261.14.

A suspension of (E)-4-(2-(6-methylquinolin-2-yl)vinyl)aniline (9.3 mg, 0.0357 mmol), (1-oxyl-2,2,5,5,-tetramethyl-Δ3-pyrroline)formaldehyde (6 mg, 0.0357 mmol) and p-toluenesulfonic acid (1 mg, 0.0058 mmol) in mixture of ethanol (1.5 mL) and anhydrous THF (0.8 mL) was sonicated for 5 min and then stirred at room temperature for additional 15 min. After the resulting solution was cooled down with ice-water bath, $NaBH_4$ (27 mg, 0.714 mmol) was added. After the mixture was stirred at room temperature overnight, water (20 mL) was added. The precipitate was collected after centrifuge and was redissolved in 80% acetonitrile in water (with 0.05% TFA) for HPLC purification using the gradient described in synthesis of SL-Res1. The eluent was collected and lyophilized to yield SL-G8 as dark red powder. The chemical identity was confirmed with Orbitrap ESI-MS. Calcd. for $C_{27}H_{30}N_3O$: 412.24, found: 413.25.

Example 7. Synthesis of SL-Sb1

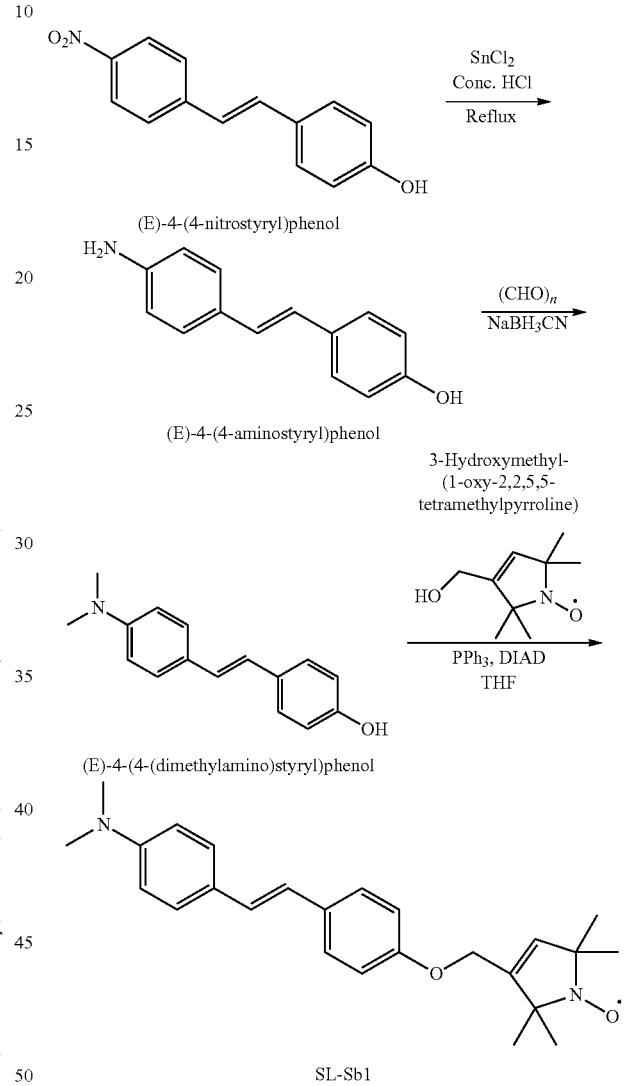

Stannous chloride (4.74 g, 25 mmol) was added to a solution of (E)-4-(4-nitrostyryl)phenol (1.2 g, 5 mmol) in ethanol (40 mL) followed by the addition of concentrated hydrochloric acid (2.0 mL). The solution was refluxed for 3 h and cooled to room temperature stirring overnight. Dark brown precipitate was collected by filtration and washed with small amount of ethanol to give (E)-4-(4-aminostyryl)phenol as HCl salt, light brown powder, 850 mg, yield 68.4%. Orbitrap ESI-MS for $C_{14}H_{13}NO$ 211.10, Found 212.10.

To a mixture of (E)-4-(4-aminostyryl)phenol HCl salt (495.4 mg, 2.0 mmol), paraformaldehyde (600 mg, 20 mmol) and sodium cyanoborohydride (378 mg, 6.0 mmol), acetic acid (20 mL) was added. The resulting mixture was heated until the solution became clear and stirred at room temperature overnight. 200 mL of water was added to the reaction solution. Sodium carbonate was added to adjust the pH to 8-9. After extraction with dichloromethane (3×40 mL), the combined dichloromethane layer was washed with water and brine and dried over anhydrous Na$_2$SO$_4$. The liquid was collected by filtration and concentrated via rotovap to give (E)-4-(4-(dimethylamino)styryl)phenol as a light grey solid, 144 mg, yield 30%. Orbitrap ESI-MS for C$_{16}$H$_{17}$NO 239.13, Found 240.14.

To an 1.5 mL eppendorf tube was added (E)-4-(4-(dimethylamino)styryl)phenol (7.7 mg, 0.032 mmol), 3-hydroxymethyl-(1-oxy-2,2,5,5-tetramethylpyrroline) (6.0 mg, 0.0352 mmol), triphenylphosphine (PPh$_3$, 9.7 mg, 0.0368 mmol), and anhydrous tetrahydrofuran (THF, 0.3 mL). The reaction tube was then lowered into a 42-kHz sonication bath (Cole-Parmer) and sonicated for 2 min. While sonicating, diisopropyl azodicarboxylate (DIAD, 7.9 µL, 0.04 mmol) was added to the reaction mixture. The reaction mixture was sonicated for 15 min, repeated three times, total 45 min. The reaction mixture was diluted with 2 mL of 50% acetonitrile/water (0.05% TFA) and then submitted for HPLC purification using the gradient described in synthesis of SL-Res1. The eluent was collected and lyophilized to yield SL-Sb1 as dark brown powder. Orbitrap ESI-MS for C$_{25}$H$_{31}$N$_2$O$_2$ 391.24 Found 392.25.

Example 8. Synthesis of SL-Sb2

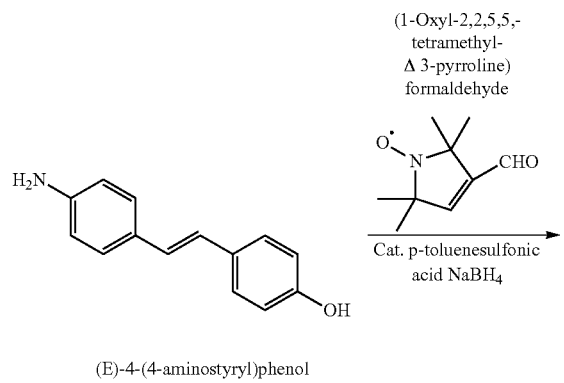

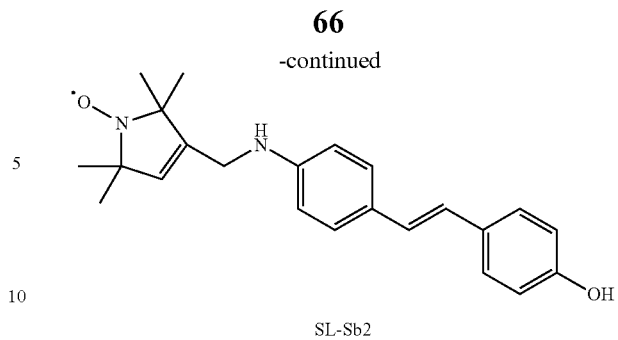

SL-Sb2

SL-Sb2 was synthesized from (E)-4-(4-aminostyryl)phenol. Its HCl salt (200 mg) was suspended in ethanol (25 mL) and then K$_2$CO$_3$ aqueous solution was added until pH 9. Water (25 mL) was added to the suspension and mixed. After centrifuge, the solid was collected by filtration and washed with water, 70% ethanol in water and dried over vacuum to give (E)-4-(4-aminostyryl)phenol as brownish solid. A suspension of (E)-4-(4-aminostyryl)phenol (7.6 mg, 0.0357 mmol), (1-oxyl-2,2,5,5,-tetramethyl-43-pyrroline)formaldehyde (6 mg, 0.0357 mmol) and p-toluenesulfonic acid (1 mg, 0.0058 mmol) in mixture of ethanol (1.5 mL) and anhydrous THF (0.8 mL) was sonicated for 5 min until the solution became clear and stirred at room temperature for additional 15 min. After the resulting solution was cooled down with ice-water bath, NaBH$_4$ (27 mg, 0.714 mmol) was added. After the mixture was stirred at room temperature overnight, water (20 mL) was added. The precipitate was collected after centrifuge and was redissolved in 80% acetonitrile in water (with 0.05% TFA) for HPLC purification using the gradient described in synthesis of SL-Res1. The eluent was collected and lyophilized to yield SL-G8 as dark brown powder. The chemical identity was confirmed with Orbitrap ESI-MS. Calcd. for C$_{23}$H$_{27}$N$_2$O$_2$: 363.21, found: 364.22, 365.22.

Example 9. Synthesis of SL-AV45

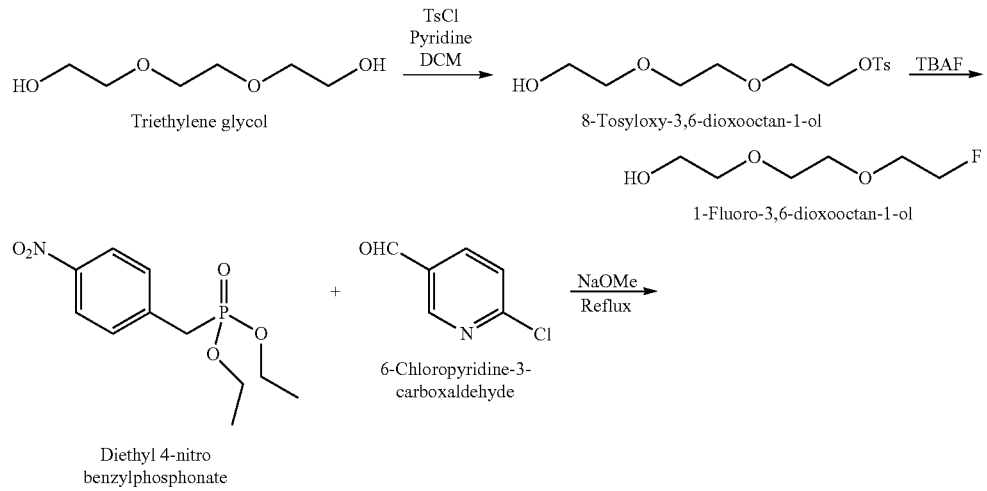

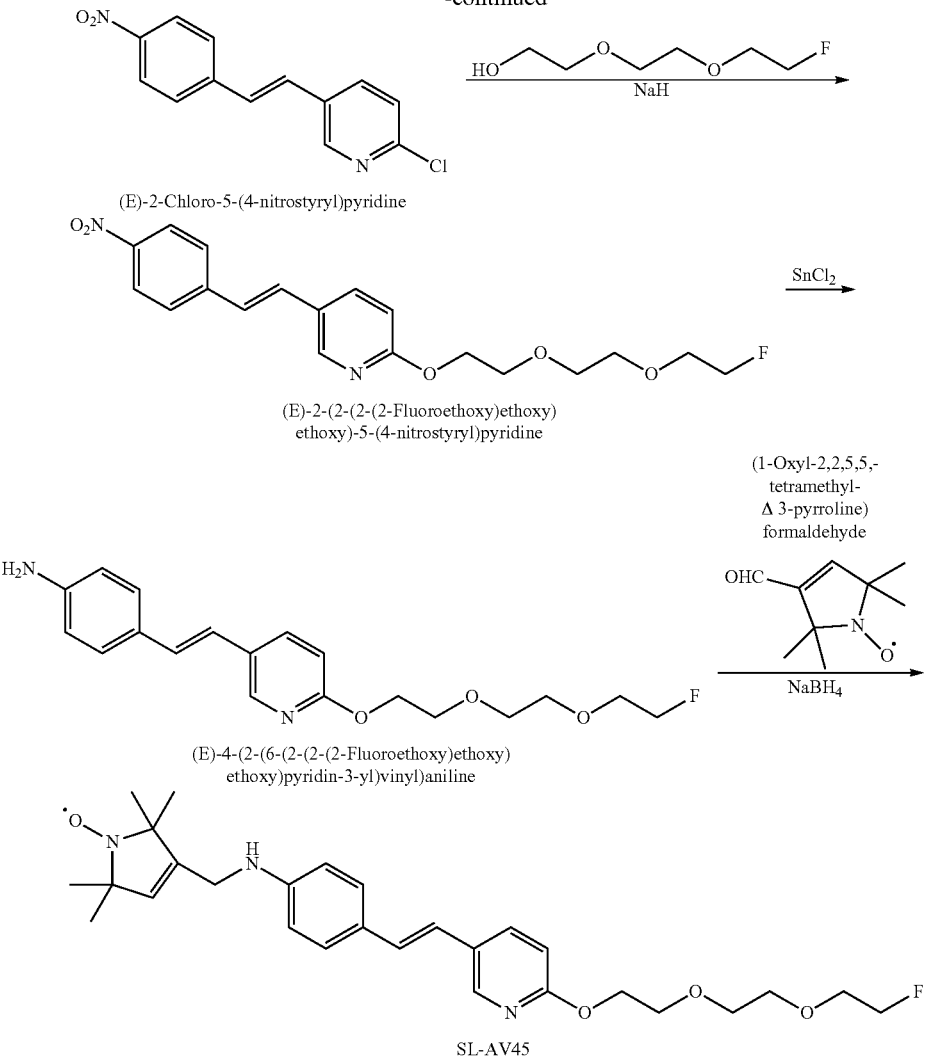

p-Toluenesulfonyl chloride (7.50 g, 40.0 mmol) was added to a solution of triethylene glycol (60.0 g, 40.0 mmol) in pyridine (6.5 mL) and dichloromethane (DCM, 400 mL) and under nitrogen. After stirring at room temperature for 18 h, the solvent was removed via rotovap. The residue was dissolved in ethyl acetate (200 mL) and washed with brine (3×100 mL). The ethyl acetate solution was dried over anhydrous $Na_2SO_4$. After filtration, the filtrate was evaporated to dryness to give crude product which was purified on a silica column to yield 8-tosyloxy-3,6-dioxooctan-1-ol as a clear oil (8.68 g, 71.3%). Orbitrap ESI-MS Calcd. for $C_{13}H_{20}O_6S$ 304.10 Found 305.11.

To a solution of 8-tosyloxy-3,6-dioxooctan-1-ol (8.5 g, 27.93 mmol) in anhydrous THF (28 mL) was added 1.0 M THF solution of tetrabutylammonium fluoride (TBAF, 32 mL, 32.0 mmol) dropwise under $N_2$. The reaction solution was stirred at room temperature overnight under N2. THF was removed by rotovap. The residue was distilled to give light brown liquid. After redistill, 1-fluoro-3,6-dioxooctan-1-ol was obtained as a colorless liquid, 2.55 g, yield 60%. Orbitrap ESI-MS Calcd. for $C_6H_{13}FO_3$ 152.08 Found 153.20.

Sodium methoxide (1M in methanol, 10.0 ml) was added slowly into a solution of diethyl 4-nitrobenzylphosphonate (1.092 g, 4.0 mmol) and 6-chloropyridine-3-carboxaldehyde (566 mg, 4.0 mmol) in methanol (10.0 mL). The reaction mixture was refluxed for 2 h, then cooled down to 0° C. Yellow precipitate was collected by filtration and washed with cold methanol and dried over vacuum to give (E)-2-chloro-5-(4-nitrostyryl)pyridine, 782 mg, yield 75%. Orbitrap ESI-MS Calcd. for $C_{13}H_9ClN_2O_2$ 260.04 Found 261.08.

1-Fluoro-3,6-dioxooctan-1-ol (600 mg, 3.92 mmol) was added into a mixture of sodium hydride (528 mg, 60% dispersion in mineral oil, 13.2 mmol) in anhydrous DMF (30 mL) at 0° C. The resulting mixture was stirred at room temperature for 0.5 h, then (E)-2-chloro-5-(4-nitrostyryl) pyridine (866 mg, 3.32 mmol) was added. The reaction mixture was stirred at 100° C. for 2 hours and cooled down. Ethyl acetate and water was added, the organic layer was separated, washed with brine, dried over anhydrous $Na_2SO_4$. After filtration, the filtrate was evaporated under rotovap. The residue was purified by on a silica column to give product (E)-2-(2-(2-(2-fluoroethoxy)ethoxy)ethoxy)-5-(4-nitrostyryl)pyridine, 480 mg, yield 38%. Orbitrap ESI-MS Calcd. for $C_{19}H_{21}FN_2O_5$ 376.14 Found 377.16.

Stannous chloride (1.13 g, 5.965 mmol) was added to a solution of (E)-2-(2-(2-(2-fluoroethoxy)ethoxy)ethoxy)-5-

(4-nitrostyryl)pyridine (450 mg, 1.193 mmol) in ethanol (12 mL) followed by the addition of concentrated hydrochloric acid (1.13 mL). The solution was refluxed for 3 h and then stirred at room temperature overnight. Precipitate was collected by filtration and re-suspended in ethanol and then neutralized with $K_2CO_3$ aqueous solution until ~pH 9. Cold water was added to precipitate. After centrifuge, the solid was collected by filtration and washed with water and dried over vacuum to give (E)-4-(2-(6-(2-(2-(2-fluoroethoxy)ethoxy)ethoxy) pyridin-3-yl)vinyl)aniline, 352 mg, yield 85%. Orbitrap ESI-MS Calcd. for $C_{19}H_{23}FN_2O_3$ 346.17 Found 347.17.

To a mixture of (E)-4-(2-(6-(2-(2-(2-fluoroethoxy)ethoxy)ethoxy) pyridin-3-yl)vinyl)aniline (11.3 mg, 0.0325 mmol) and (1-oxyl-2,2,5,5,-tetramethyl-43-pyrroline)formaldehyde (6 mg, 0.0357 mmol) in ethanol (1.5 mL) and anhydrous THF (0.8 mL) was added p-toluenesulfonic acid (1 mg, 0.0058 mmol) (0.8 mL). The resulting mixture was sonicated for 5 min and stirred at room temperature for additional 30 min. $NaBH_4$ (27 mg, 0.714 mmol) was added at 0° C. After the mixture was stirred at room temperature overnight, water (20 mL) was added. The precipitate was collected after centrifuge and was redissolved in 80% acetonitrile in water (with 0.05% TFA) for HPLC purification using the gradient described in synthesis of SL-Res1. The eluent was collected and lyophilized to yield SL-AV45. The chemical identity was confirmed with Orbitrap ESI-MS. Calcd. for $C_{28}H_{37}FN_3O_4$: 498.28, found: 499.30.

Example 10. HO-4160 Labeling Facilitates In Vitro Detection of Amyloid Plaque in Brain Specimen from an AD Transgenic Mouse Model MR images of coronal brain slices (400 μm thick) were obtained from a transgenic AD mouse model (5xFAD) with and without exposure to HO-4160 nitroxide spin-labeled fluorine (SLF), where the SLF-negative sample was treated with DMSO vehicle equal to the SLF-exposed sample. Following the labeling period with either SLF or the DMSO vehicle control, the brain slices were imbedded into agarose and imaged by MRI. Measurements were made in three separate experiments, using slices from unique AD and wild type (WT) mice in each experiment. SLF does not provide observable contrast in the Tl-weighted image intensities. However, both T2 and T2*-weighted imaging show negative contrast in the SLF-treated specimen (FIG. 5).

5xFAD brain slices treated with SLF decrease in intensity to a mean value of $1.6\pm0.1\times10^5$, compared to the T2-weighted images of the untreated samples, with a mean value of $2.6\pm0.1\times10^5$. Evaluation of the two sets by the unpaired t-test supports a significant difference among these groups (p<0.01). With respect to T2*, there also is a significant (p<0.02) intensity difference between the two groups of 5xFAD specimens, with a mean intensity of $1.4\pm0.2\times10^5$ for the SLF-treated samples, and a mean intensity of $2.3\pm0.1\times10^5$ for the untreated samples. In addition, T2 and T2*-weighted imaging of corresponding slices from WT mice show no difference between the SLF-treated and SLF-negative (not shown) specimens. Thus the SLF-induced negative contrast is specific to the AD model mouse specimens that contain a high AB load.

Figure 6:
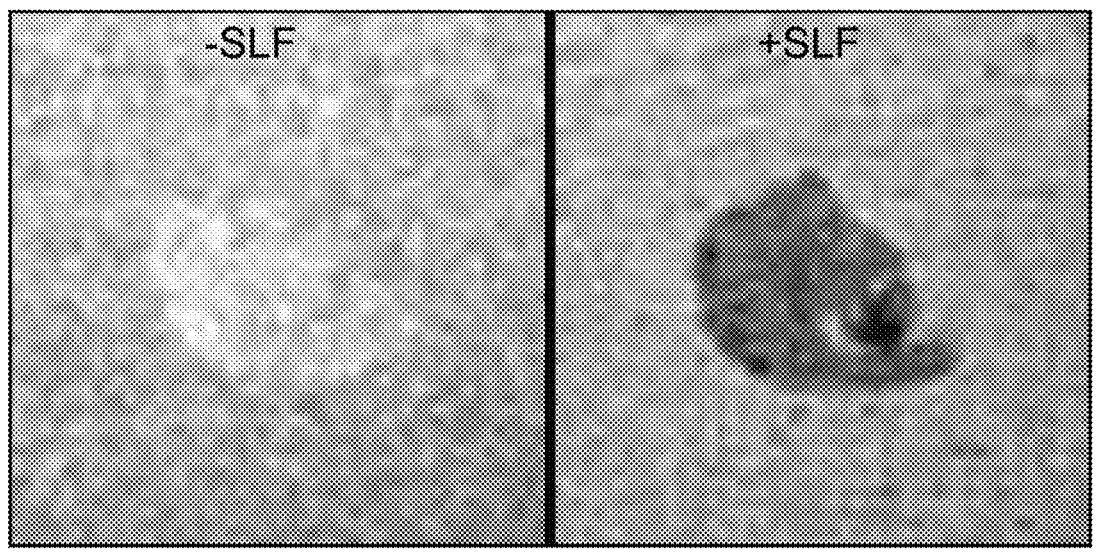
FIG. 6 shows magnetic resonance images of APP-PS1 mouse brain specimens after administration of SLF. The T2*-weighted images of APP-PS1 mouse coronal hemispheric brain slices show marked loss of intensity in the SLF-labeled specimen depicted in the right panel relative to the SLF-free specimen depicted in the left panel.

In addition, T2 and T2*-weighted imaging of corresponding slices from WT mice show no difference between the SLF-treated and SLF-negative specimens (FIG. 6). Thus the SLF-induced negative contrast is particular to specimens that contain a high AB load. A similar qualitative result is obtained when using brain specimens from the PS/APP mouse model, where SLF-treatment of the sample results in a substantial negative contrast in the T2*-weighted MRI image (FIG. 6).

Figure 7:
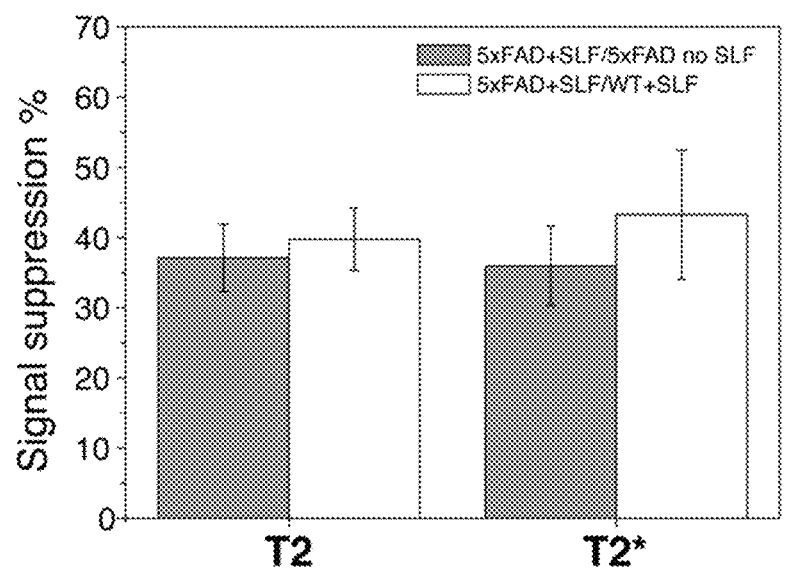
FIG. 7 shows the magnitude of signal suppression by SLF in a 5xFAD mouse slice compared to a control of either vehicle-treated 5xFAD or SLF-treated WT. Error bars represent the standard error among values from three different experiments.

Example 11. Quantification of Negative Contrast from SLF Labeled Amyloid Plaques Detected by MRI Both T2 and T2* signal suppression was calculated in each of the three experiments. The average suppression values were calculated according to the equation:

$$SS\% = [(SI_{ref} - SI)/SI_{ref}] * 100$$

where SI is the average signal intensity of the 5xFAD SLF+ section and $SI_{ref}$ is the average signal intensity of the 5xFAD SLF− or WT SLF+ section. Calculation results are plotted in FIG. 7, where both the gray and white bars represent the suppression of MRI intensity found in the 5xFAD specimen following SLF treatment. The gray bars show signal suppression relative to the untreated 5xFAD brain, while the white bars compare the suppression relative to the SLF-treated specimens from WT mice. Relative to both controls, SLF generates ~40% signal suppression for samples carrying a high amyloid-beta load. In the absence of SLF, the average intensity of the 5xFAD brain sections have a slightly lower T2/T2* MRI intensity than specimens from WT mice. This can be attributed to iron bound to deposits of AB, which has been previously observed in the MRI analyses of AD model mice (Vanhoutte et al. (2005); Jack et al. (2007); and Wadghiri et al. (2012)). Thus, the relative suppression is slightly higher when comparing the +SLF AD sample to the +SLF WT sample. This finding clearly demonstrates the ability of SLF to specifically label amyloid plaques and generate negative contrast on MR images.

Figure 8:
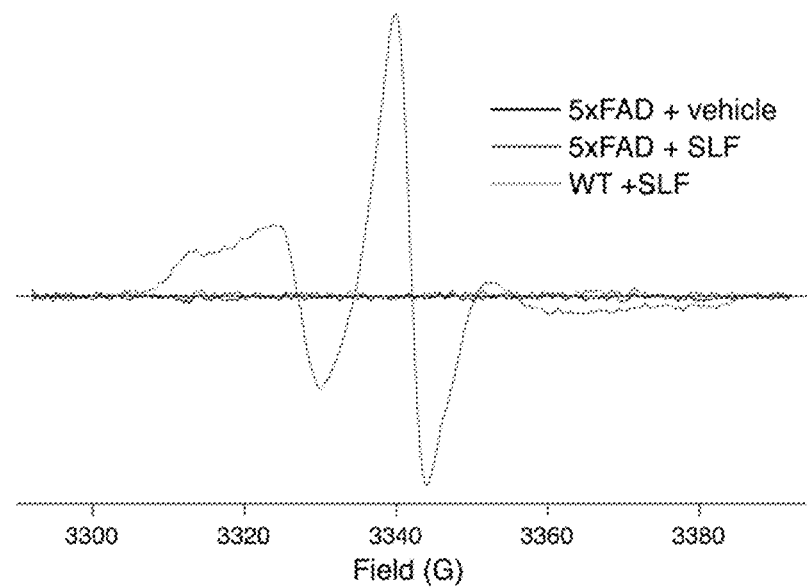
FIG. 8 shows results of electron paramagnetic resonance (EPR) examination of 5xFAD mouse brain specimens after administration of SLF. Specific binding of SLF to AB is indicated by the presence of an immobilized nitroxide spectrum from the 5xFAD SLF+ mouse coronal brain slice. There is a lack of signal in the 5xFAD SLF− sample and the WT SLF+ sample.

Example 12. High SLF Binding with Specificity to the Presence of Amyloid is Supported by EPR Analyses Samples were loaded into a quartz cell and examined by electron paramagnetic resonance (EPR) spectroscopy. As shown in FIG. 8, an intense EPR signal was obtained from the SLF-treated 5xFAD brain tissue, however no signal was obtained from similarly treated WT brain tissue. Thus, in agreement with results from the MRI measurements, the lack of EPR signal from the WT+SLF brain section excludes non-specific binding of SLF in these tissue samples. As expected, the 5xFAD sample lacking SLF treatment showed no EPR signal. The broad EPR spectrum from the +SLF 5xFAD reflects a strongly immobilized spin probe, consistent with high affinity binding to a solidified matrix. This highly immobilized state of SLF is not observed in soluble AB, where the molecule displays a high degree of motional averaging due to the fast rotational diffusion within this species (Altman et al. (2015)).

Figure 9:
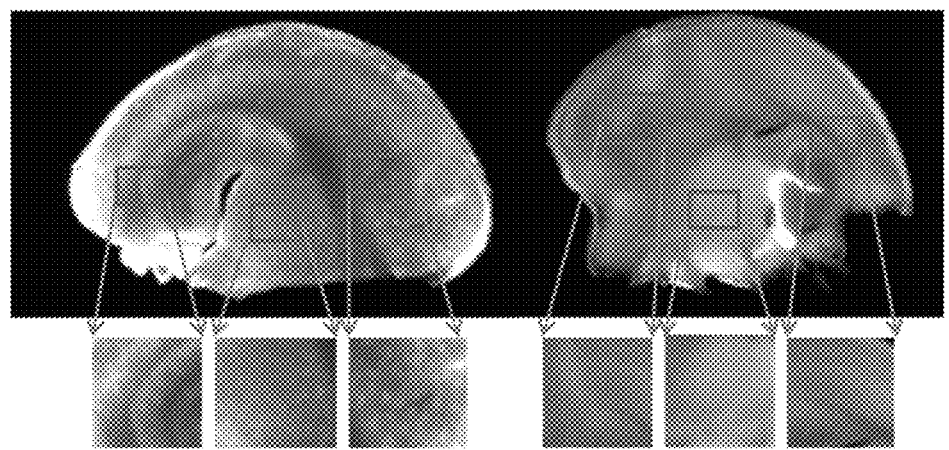
FIG. 9 shows near-infrared fluorescence images of antibody directed against the AB peptide in 5xFAD SLF+ (left panel) and WT (right panel) mouse brain coronal sections. The coronal sections include the hippocampus and cortex. Diffuse distribution of AB is seen as white dots throughout the surface area of the 5xFAD mouse model, correlating with the relatively uniform distribution of negative contrast generated in T2*-weighted MRI images of 5xFAD specimens treated with SLF. Such features are absent in the control mouse. Zoomed views in the boxes below provide greater detail of selected areas.

Example 13. Anti AB Immunohistochemistry Correlates Distribution of Amyloid Plaques Detected by MRI Brain slices from 5xFAD transgenic mice that were administered SLF were immunostained with the Anti-beta-Amyloid, 17-24 (4G8) monoclonal antibody. Results shown in FIG. 9 indicate the presence of amyloid plaque through antibody fluorescence appearing as dark region with a pattern of white dots. This antibody fluorescence correlates with the diffuse dark pattern (loss of intensity) seen throughout the 5xFAD+SLF mouse brain slice in T2*—weighted MRI images.

Example 14. Assessment of SLF Blood-Brain Distribution

Table 1 below reports the plasma and brain levels of the SLF compound following intraperitoneal injection of three mice at a dose of 10 mg/kg. Total SLF plasma concentrations were measured from each mouse at 20, 40 and 60 minutes after administration. The mice were euthanized 60 min after injection, and their brains were removed and stored at −80° C. UPLC-MS/MS analysis of the SLF in the samples found brain concentrations at roughly 50% of plasma concentrations corresponding to a brain/plasma ratio of 0.5. Taken together, these data demonstrate that SLF is sufficiently brain penetrant to be useful as an imaging probe.

TABLE 1

Post-injection levels of SLF in mouse brain and plasma.
Uncertainty of mean is given as Standard Error.

| Tissue (time) | [SLF] (nM) | | |
|---|---|---|---|
| | Mouse-1 | Mouse-2 | Mouse-3 |
| Plasma (20 Min) | 396 | 397 | 663 |
| Plasma (40 Min) | 321 | 431 | 424 |
| Plasma (60 Min) | 492 | 530 | 432 |
| Brain (60 Min) | 185 | 268 | 229 |
| B:P (60 min) | 0.38 | 0.51 | 0.53 |
| Mean P:B (60 min) | 0.47 ± 0.05 | | |

Example 15. Demonstration of SLF In Vivo Paramagnetism and Accumulation

Figure 10:
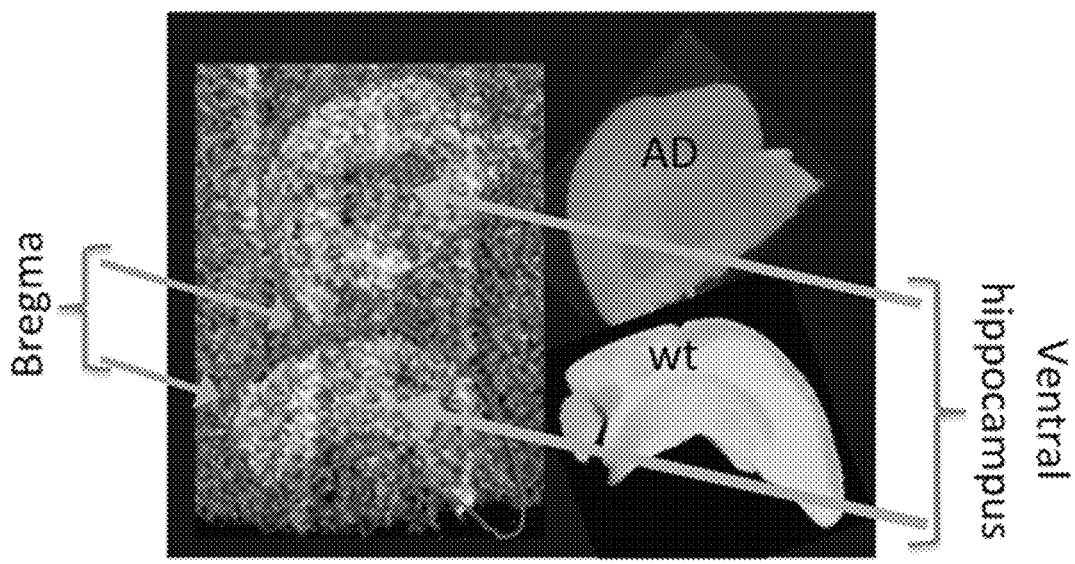
FIG. 10 shows the T2*-weighted MR image of 400-μm, ex-vivo hemi-coronal brain sections from a 5 month-old 5xFAD transgenic mouse (top left) and a wild type mouse (bottom right) following intravenous injection of SLF at a concentration of approximately 3 mg/kg. The 5xFAD sample shows a marked loss of intensity in the hippocampus area versus the wild type specimen. Photos of each slice are shown to the right.

SLF was injected (i.v., ~3 mg/kg) via tail vein into one 5xFAD mouse and one WT mouse for ex vivo analysis of SLF in brain tissue. After 24 hrs, the mice were euthanized and their brains were removed and fixed in 4% paraformaldehyde overnight at 4-8° C. From these brain samples, 400 μm coronal slices were prepared and imbedded in agarose. FIG. 10 provides MR images of hemicoronal slices (at bregma −2.12) of both 5xFAD and WT mice. The T2*-weighted images of the 5xFAD brain tissue show a slight negative contrast for the 5xFAD mouse coronal slice at the area corresponding to the ventral hippocampus and thalamus. This negative contrast was absent in the specimens from the WT mouse.

Example 16. Verification of Preferential Retention of Paramagnetic SLF

Figure 11:
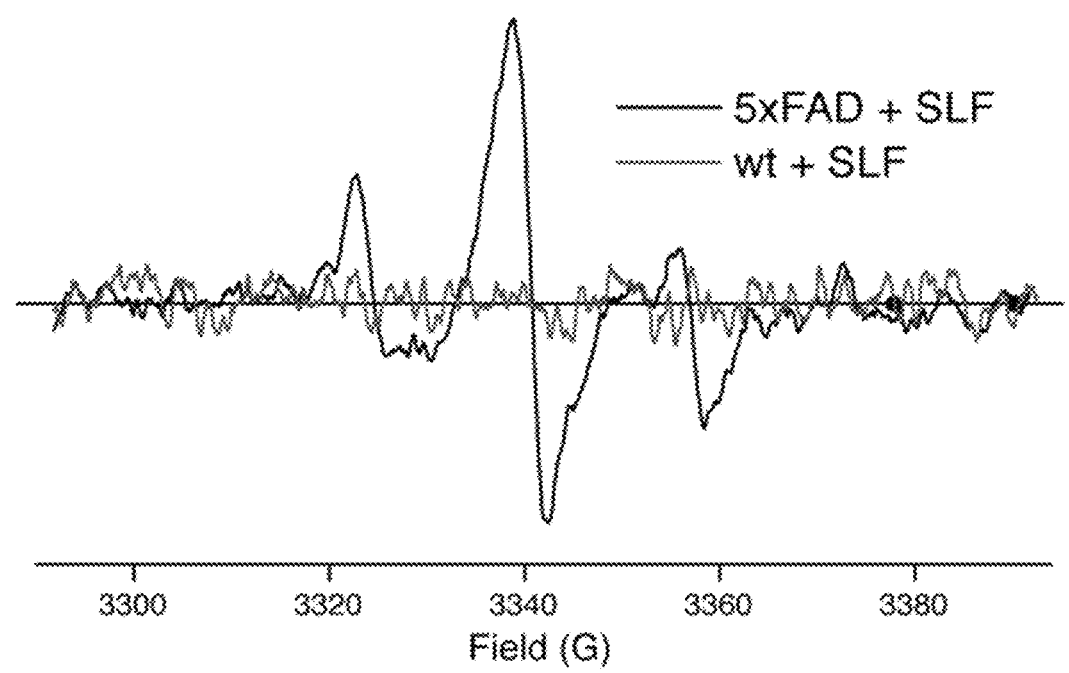
FIG. 11 shows how the binding of SLF within the brain of a 5xFAD mouse intravenously injected with the compound can be revealed by EPR examination of the ex vivo brain specimen. Shown are the 100 G X-band EPR spectra of brain slices harvested 24-hr post injection from a 5xFAD mouse and a wild type mouse. Both mice were injected with approximately 3 mg/kg SLF.

The brain specimens collected from SLF-injected mice and described in the above Example were removed from the agarose slab and analyzed for their nitroxide EPR signal (FIG. 11). Consistent with our results from in vitro SLF labeling of brain slices, the WT mouse brain specimen shows no EPR signal, eliminating the non-specific binding of SLF in the tissue samples examined, while the brain slice isolated from the SLF-injected 5xFAD mouse produced a clear EPR signal. Compared to the signal obtained by in vitro SLF labeling (FIG. 8), the 5xFAD+SLF sample in FIG. 11 generates a weaker EPR signal. However, the sample in FIG. 8 was fully bathed in SLF, whereas the SLF labeling of the tissue in FIG. 11 is dependent on accessibility to cerebrospinal fluid (CSF).

Example 17. Confirmation of SL-LRL1 Binding to Brain Tissue

Figure 12:
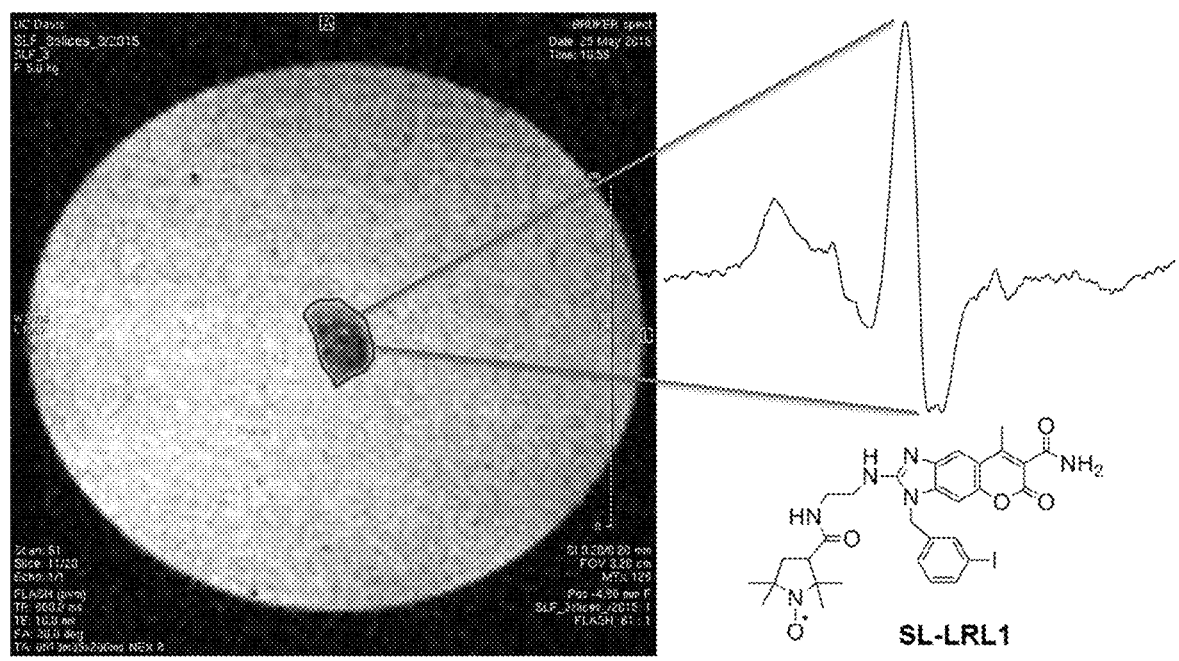
FIG. 12 shows an MRI image and EPR spectrum for a mouse brain specimen treated with SL-LRL1.

The nitroxide spin-labeled compound, LRL1 was synthesized and incubated with the 5xFAD mouse brain specimens In the left panel of FIG. 12, it is clear that LRL1 generates a strong negative contrast in the T2*-weighted MRI image for 5xFAD specimen. The right panel of FIG. 12 shows the EPR spectrum of the sample after MRI analysis, confirming the binding of the LRL1 compound to the brain tissue.

Figure 13:
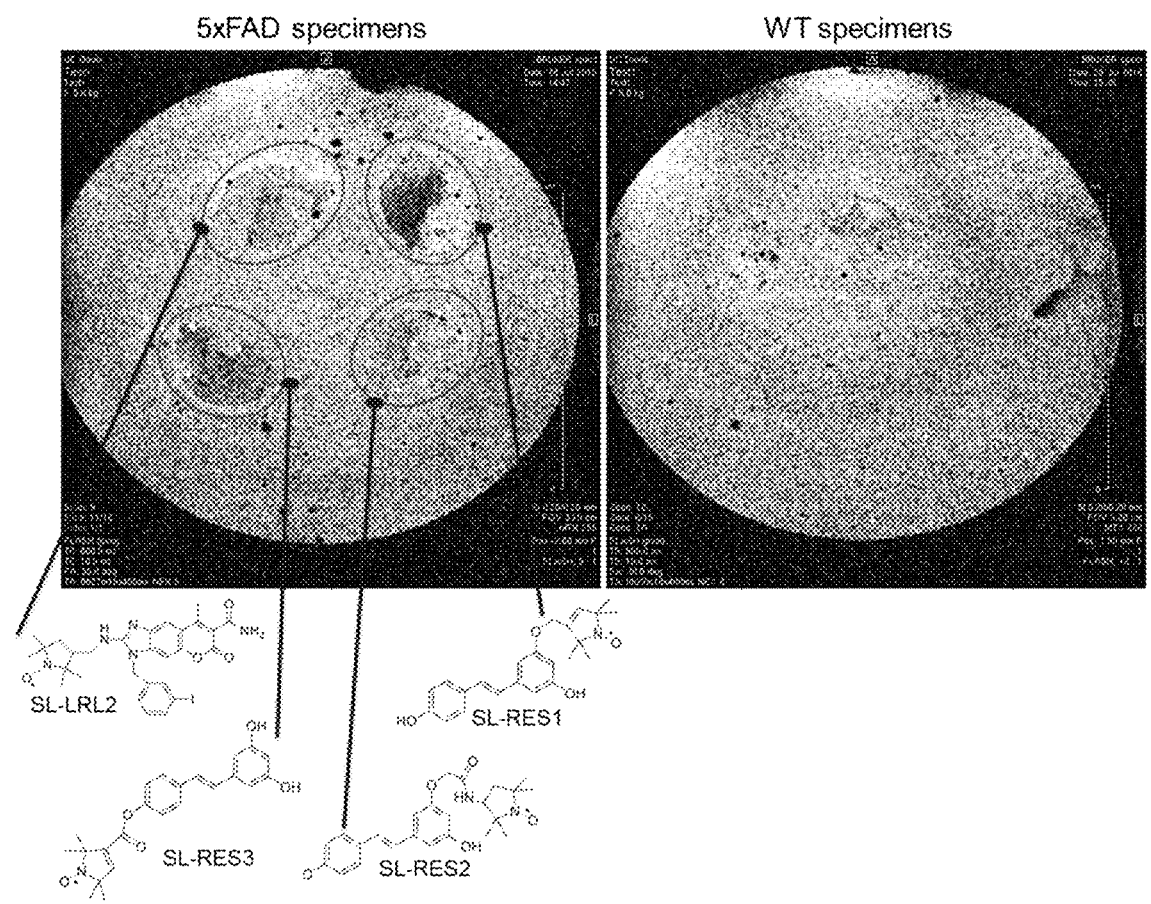
FIG. 13 shows MRI images of 5xFAD and WT mouse brain specimens treated with SL-LRL2, SL-Res1, SL-Res2, and SL-Res3.

Example 18. Confirmation of SL-LRL2, SL-Res1, SL-Res2, and SL-Res3 Binding to Brain Tissue The nitroxide spin-labeled compounds, LRL2, SL-Res1, SL-Res2, and SL-Res3 were synthesized and incubated with the 5xFAD mouse brain specimens FIG. 13 shows that each of these four compounds has the ability to generate negative contrast in T2*-weighted MRI images of brain specimens isolated from 5xFAD mice (left panel), but not WT (normal) mice (right panel).

Example 19. Evidence for Therapeutic Effects of SL-LRL1, SL-LRL2, SL-Res1, SL-Res2, and SL-Res3

The ability of agents to protect against AB toxicity can be measured according to their effect on the survivability of MC65 neuroblastoma cell (Maezawa et al. (2008) *J. Neurochem.* 104:457). In the MC65 model system, expression of the C-terminal region (C99) of the amyloid precursor protein (APP) is turned on in the absence of the transgene suppressor, tetracycline (TC). Upon APP-C99 induction (TC-), AB is generated after proteolysis by cellular γ-secretase containing conditional expression. In the absence of protection, death of MC65 neuroblastoma cells results due to the intracellular accumulation of oligomeric AB (ABO). As an example, we showed in Petrlova et al. (2012) that SLF provides protection against AB toxicity with a potency nearly an order of magnitude greater than the non-spin labeled parent fluorene K01-162. In Table 2 below, we report the ability of the SL-LRL1, SL-LRL2, SL-Res1, SL-Res2, and SL-Res3 compounds to protect against AB toxicity in the MC65 assay.

TABLE 2

Potency of new spin-labeled amyloid agents in protection against
AB toxicity as determined by the MC65 assay. EC50 represents the
concentration of compound that achieves 50% of the maximal effect, where
the maximal effect for all compounds is 100% cell viability.

| Compound | $EC_{50}$ (μM) |
|---|---|
| SL-LRL1 | 4.5 |
| SL-LRL2 | 3.5 |
| SL-Res1 | 0.45 |
| SL-Res2 | 0.68 |
| SL-Res3 | 0.41 |

The cell culture model used for these studies was the human neuroblastoma cell line (MC65) equipped with conditional expression of the carboxyl-terminal 99 residues of the amyloid-beta precursor protein (APP-C99). AB is generated from APP-C99 after proteolysis by cellular γ-secretase. To induce cellular AB production, the transgene suppressor, tetracycline (TC), was removed from the media, as described previously (Maezawa et al. (2008)). Intracellular ABO starts to accumulate as early as 4 hours after TC removal. The compounds were added immediately after TC removal, and the cells were maintained for 3 days without media change before measuring cell viability. The cytotoxicity was determined on day 3 using a colorimetric MTT [3-(4,5-dimethylthiazol-2yl)-2,5-diphenyltetrazolium bromide] cell viability assay.

Example 20. AB Pathogenicity

Figure 14:
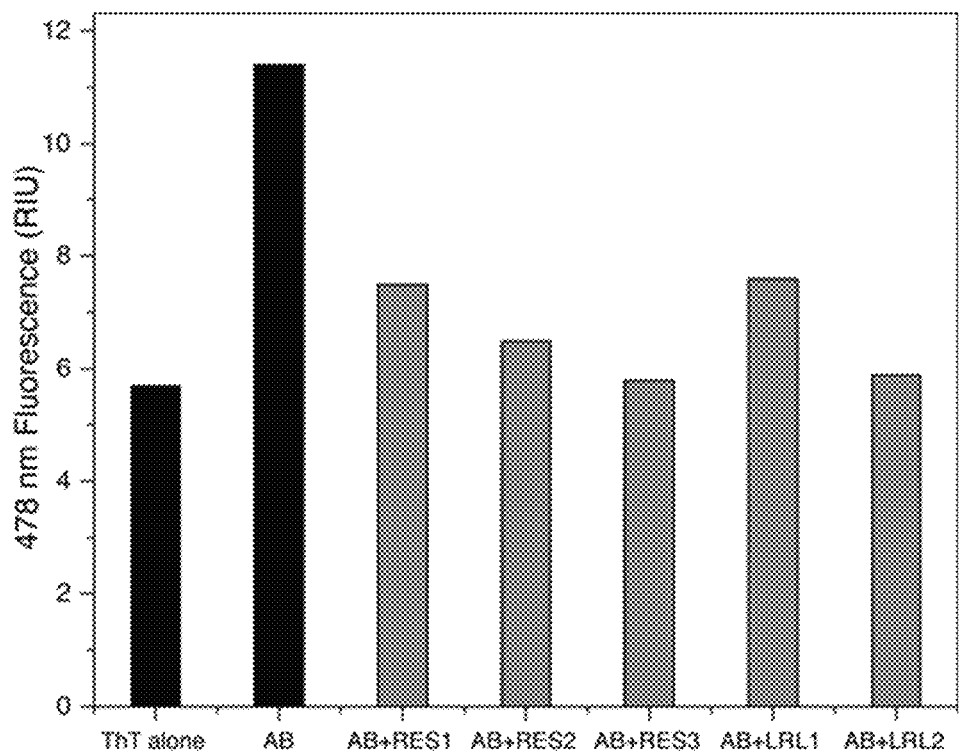
FIG. 14 shows fluorescence emission of ThT alone, in combination with oligomeric AB, or in combination with RES/LRL compounds. Compared to AB alone, ThT binding (as indicated by emission at 478 nm) is decreased by RES1-3 and LRL1-2.
Figure 14:
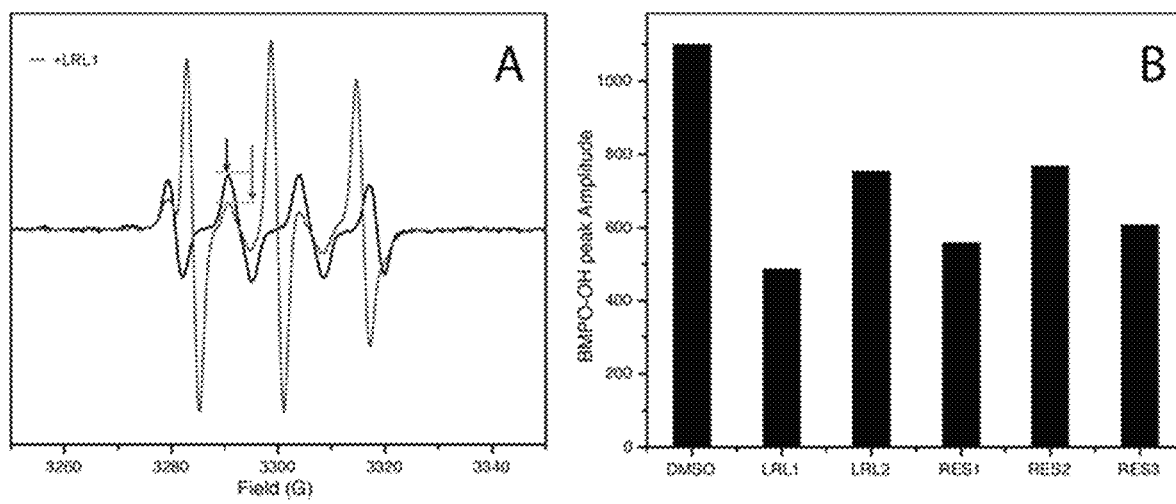

The pathogenicity of AB can be related to a toxic conformation particular to the soluble, oligomeric state of the peptide. To test the ability of our agents to reverse the toxic conformation of AB, we measured the effect of LRL1-2 and RES1-3 on the binding of amyloid dye Thioflavin-T (ThT) to oligomeric AB, which serves as a general indicator of AB aggregation and fibril formation, providing a simple method to identify agents that remodel AB into non-toxic comformers. Since the fluorescence of ThT at 478 nm increases as AB forms toxic aggregates, we tested the effect of RES1-3 and LRL1-2 on the ThT fluorescence in the presence of oligomeric AB. As indicated in FIG. 14, the addition of RES1-3 and LRL1-2 suppresses the 478 nm emission signal of the AB and ThT mixture relative to the sample without addition. This indicates each compound directly engages AB and alters its amyloidogenic and toxicity profile.

Although AB is known to disrupt multiple cellular functions, oxidative damage to proteins and lipids is a general feature of its pathogenic mechanism. Because nitroxides have a unique antioxidant activity, our compounds have a strong potential to counteract oxidative stress. Our compounds engage AB directly, and therefore these agents are designed to be especially effective in scavenging reactive oxygen (ROS) and nitrogen species (NOS) by localizing antioxidant functionality at AB. FIGS. 15A & B shows that LRL1-2 and RES1-3 are effective scavengers of ROS, as measured by spin trapping.

Although the foregoing invention has been described in some detail by way of illustration and Example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

Where a conflict exists between the instant application and a reference provided herein, the instant application shall dominate.

What is claimed is:

1. A method of imaging amyloid, comprising:
administering to a subject an effective amount of a compound, wherein the compound is selected from the group consisting of:

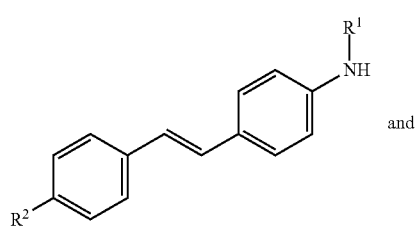

and

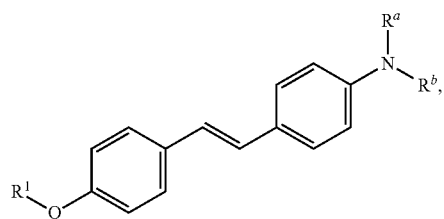

wherein:

$R^1$ is selected from the group consisting of:

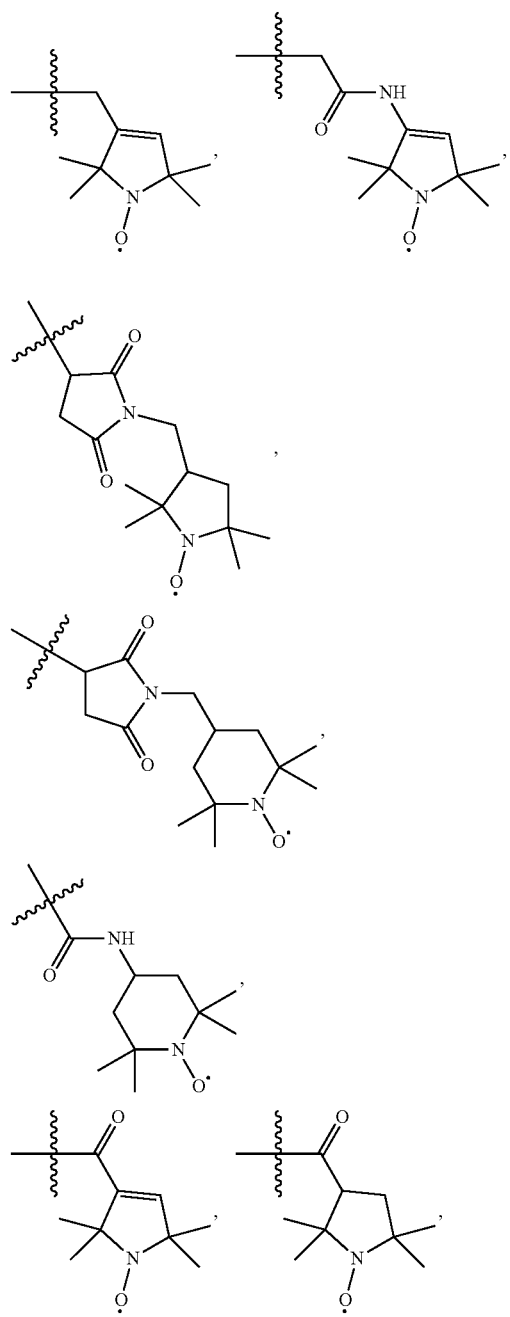

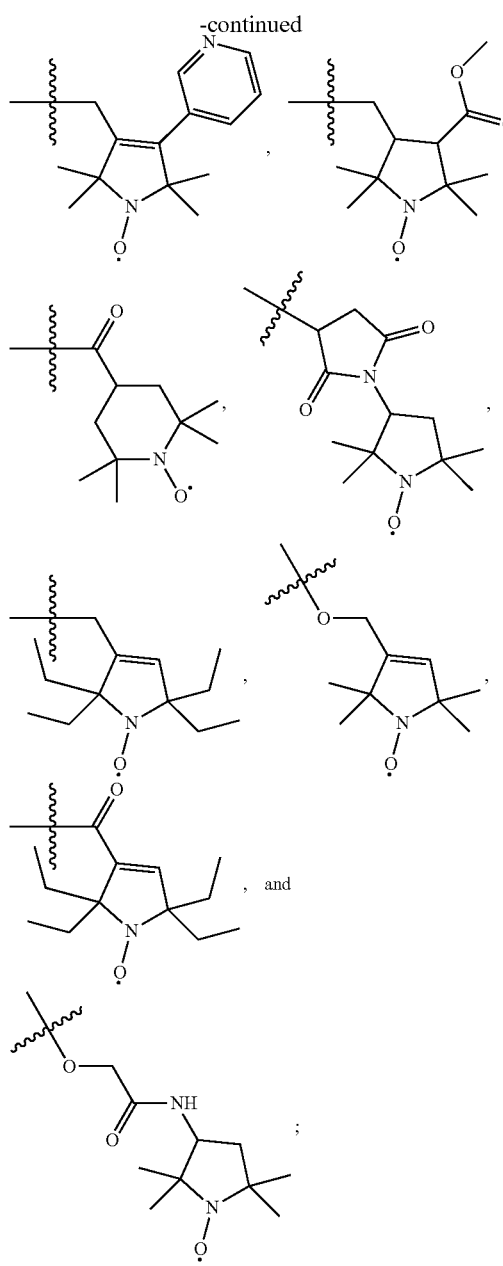

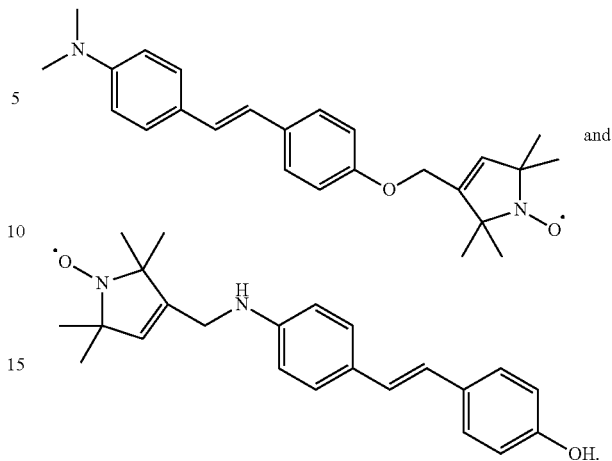

6. The method of claim 1, wherein the subject is not receiving the compound for therapeutic purposes.

7. A diagnostic composition for imaging amyloid, comprising a compound, wherein the compound is selected from the group consisting of:

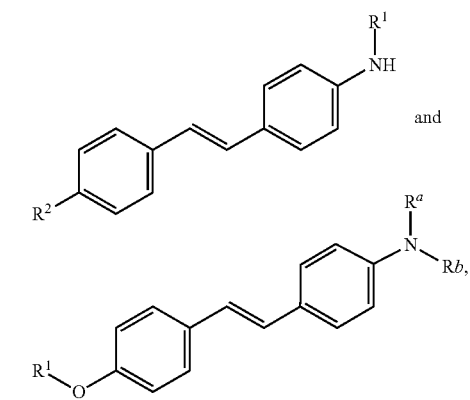

wherein:

$R^1$ is selected from the group consisting of:

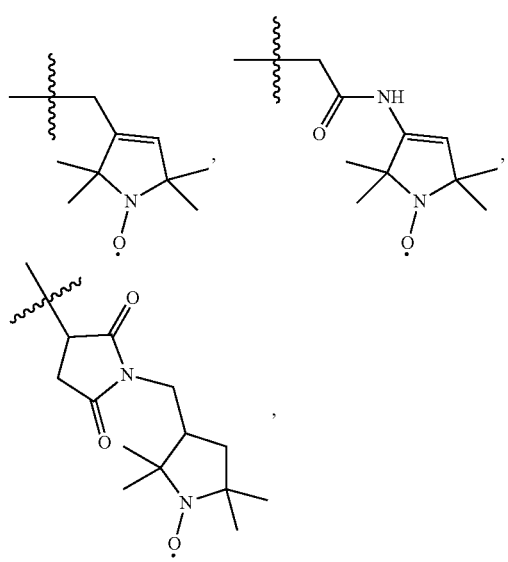

$R^2$ is selected from the group consisting of OH, $OCH_3$, $OCH_2CH_3$, $OCH_2CH_2F$, $CH_3$, and $(OCH_2CH_2)_3F$; and $R^a$ and $R^b$ are each independently H or $C_{1-4}$ alkyl and detecting the compound bound to the amyloid, thereby imaging the amyloid.

2. The method of claim 1, wherein the detecting occurs at least 60 minutes subsequent to the administering.

3. The method of claim 1, wherein the detecting comprises at least one of magnetic resonance imaging (MRI), electron paramagnetic resonance (EPR), positron emission tomography (PET), or electron spin resonance microscopy (ESRM).

4. The method of claim 1, wherein the amyloid comprises amyloid beta aggregates.

5. The method of claim 1, wherein the compound is selected from the group consisting of:

-continued

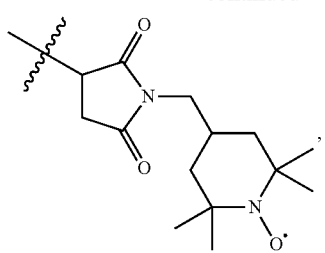,

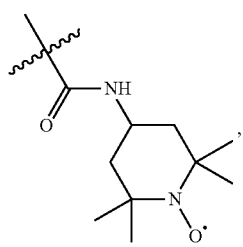,

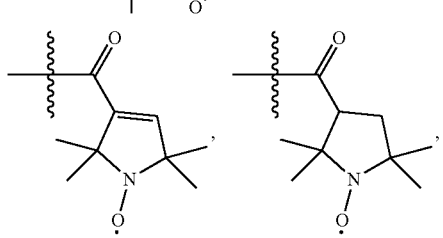,

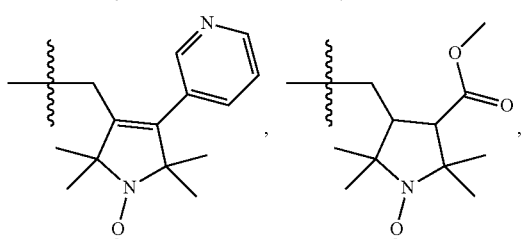,

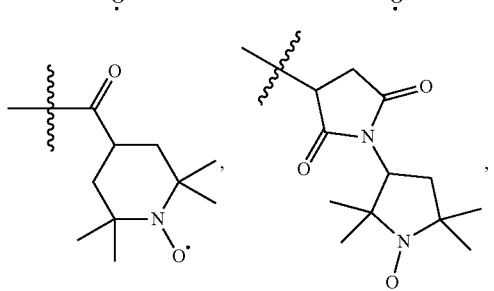,

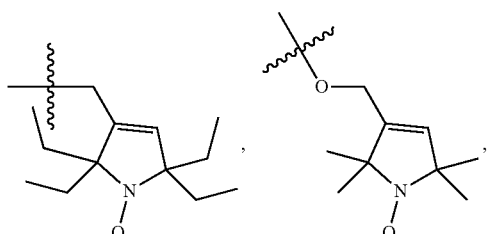,

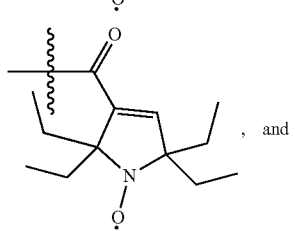, and

-continued

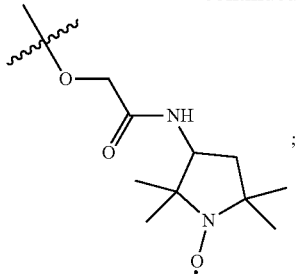;

$R^2$ is selected from the group consisting of OH, OCH$_3$, OCH$_2$CH$_3$, OCH$_2$CH$_2$F, CH$_3$, and (OCH$_2$CH$_2$)$_3$F; and $R^a$ and $R^b$ are each independently H or C$_{1-4}$ alkyl.

8. A method of treating a disorder, the method comprising administering to a subject in need thereof, a therapeutically effective amount of a compound, wherein the compound is selected from the group consisting of:

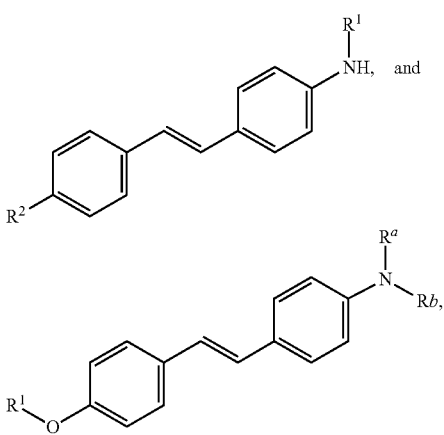

wherein:

$R^1$ is selected from the group consisting of:

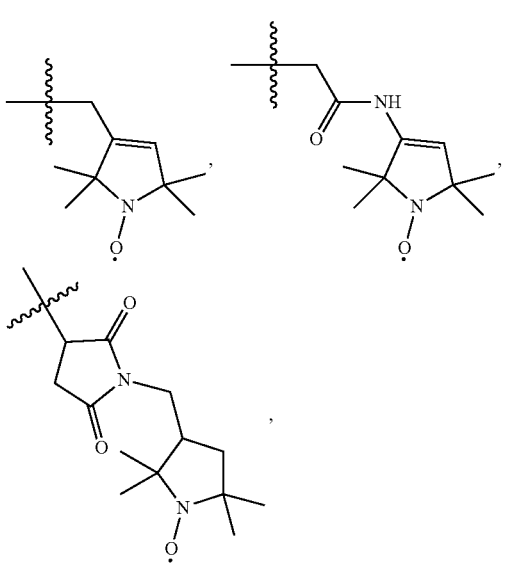

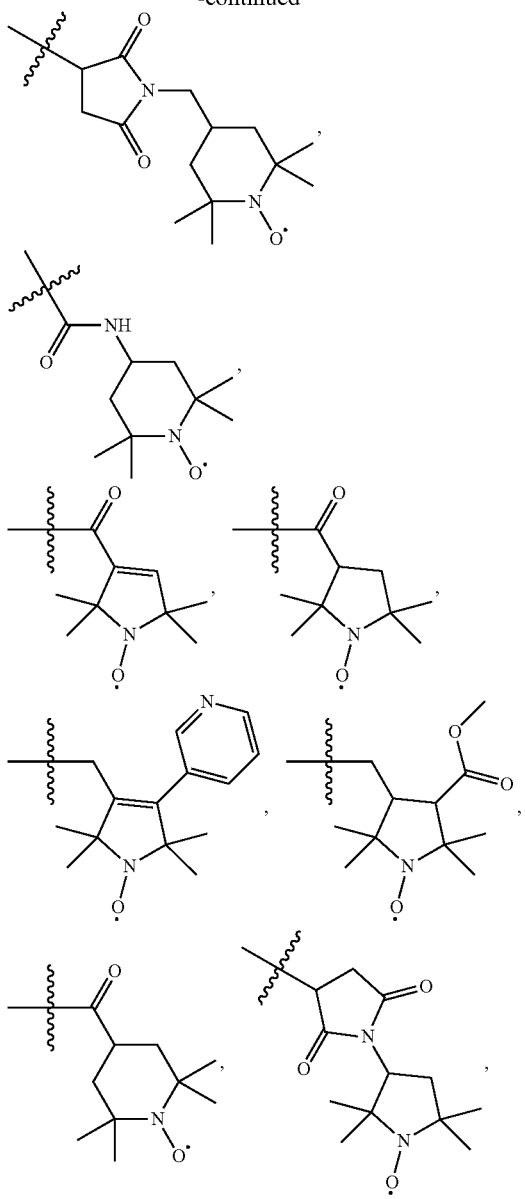
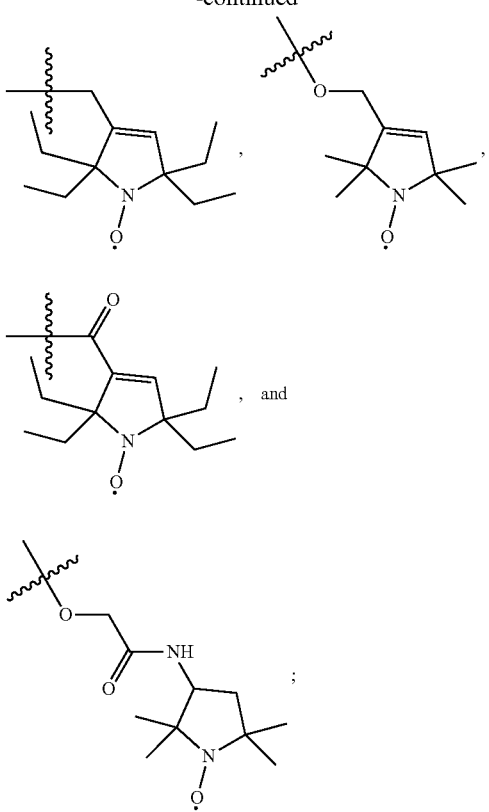

$R^2$ is selected from the group consisting of OH, $OCH_3$, $OCH_2CH_3$, $OCH_2CH_2F$, $CH_3$, and $(OCH_2CH_2)_3F$; and $R^a$ and $R^b$ are each independently H or $C_{1-4}$ alkyl; and wherein the disorder is selected from the group consisting of Alzheimer's disease, diabetes Parkinson's disease, spongiform encephalopathy, Huntington's disease, thyroid carcinoma, atrial amyloidosis, atherosclerosis, arthritis, prolactinomas, polyneuropathy, corneal dystrophy, and cerebral amyloid angiopathy.

* * * * *